(12) United States Patent
Disney et al.

(10) Patent No.: US 9,795,687 B2
(45) Date of Patent: Oct. 24, 2017

(54) MODULARLY ASSEMBLED SMALL MOLECULES FOR THE TREATMENT OF MYOTONIC DYSTROPHY TYPE 1

(71) Applicant: The Scripps Research Institute, La Jolla, CA (US)

(72) Inventors: Matthew D. Disney, Jupiter, FL (US); Suzanne Rzuczek, Jupiter, FL (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 14/915,439

(22) PCT Filed: Aug. 29, 2014

(86) PCT No.: PCT/US2014/053520
§ 371 (c)(1),
(2) Date: Feb. 29, 2016

(87) PCT Pub. No.: WO2015/031819
PCT Pub. Date: Mar. 5, 2015

(65) Prior Publication Data
US 2016/0206753 A1    Jul. 21, 2016

Related U.S. Application Data

(60) Provisional application No. 61/871,483, filed on Aug. 29, 2013.

(51) Int. Cl.
*A61K 47/48* (2006.01)
*C07D 233/22* (2006.01)
*A61K 31/496* (2006.01)
*A61K 38/00* (2006.01)

(52) U.S. Cl.
CPC ...... *A61K 47/48338* (2013.01); *A61K 31/496* (2013.01); *A61K 47/481* (2013.01); *A61K 47/48038* (2013.01); *C07D 233/22* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 9,150,612 B2* | 10/2015 | Disney | C07K 14/001 |
| 2008/0227213 A1* | 9/2008 | Disney | C07K 14/001 |
| | | | 436/94 |
| 2016/0257669 A1* | 9/2016 | Disney | C07D 519/00 |

FOREIGN PATENT DOCUMENTS

WO   WO-2015/031819 A1   3/2015

OTHER PUBLICATIONS

Lee, Melissa M. et al, "Controlling the specificity of modularly assembled small molecules for rna via ligand module spacing: targeting the rnas that cause myotonic muscular dystropy." J. Am. Chem. Soc. (2009) 131 p. 17464-17472.*
The webpage from SigmaAldrich describing bifunctional linkers, https://web.archive.org/web/20081027212623/http://www.sigmaaldrich.com/chemistry/chemistryproducts.html?TablePage=16250332, available online Oct. 27, 2008.*
"International Application Serial No. PCT/US2014/053520, International Preliminary Report on Patentability dated Mar. 10, 2016", 6 pgs.
"International Application Serial No. PCT/US2014/053520, International Search Report dated Dec. 4, 2014", 4 pgs.
"International Application Serial No. PCT/US2014/053520, Written Opinion dated Dec. 4, 2014", 4 pgs.
Gao, et al., "Synthesis and Screening of Stereochemically Diverse Combinatorial Libraries of Peptide Tertiary Amides", Chemistry & Biology 20, (Mar. 21, 2013), 360.
Tanada, et al., "Design of New Bidentate Ligands Constructed of Two Hoechst 33258 Units for Discrimination of the Length of Two A3T3 Binding Motifs", J Org Chem 2006, 71(1),, (2006), 125-134.

* cited by examiner

*Primary Examiner* — Fred Reynolds
(74) *Attorney, Agent, or Firm* — Thomas Fitting; Hugh Wang

(57) ABSTRACT

To study RNA function using small molecules, we designed bioactive, modularly assembled small molecules that target the noncoding expanded RNA repeat that causes myotonic dystrophy type 1 (Dm1), r(CUG)exp. Different modular assembly scaffolds were investigated including polyamines, alpha-peptides, beta-peptides, and peptide tertiary amides (PT As). Based on activity as assessed by improvement of DM1-associated defects, stability against proteases, cellular permeability, and toxicity, we discovered that constrained backbones, namely PT As, are optimal.

1 Claim, 33 Drawing Sheets

2H-K4NMe Biotin

K4NMe Biotin

Hoechst 33258 Control Cells

10 μM

1 μM

2H-3G

10 μM

1 μM

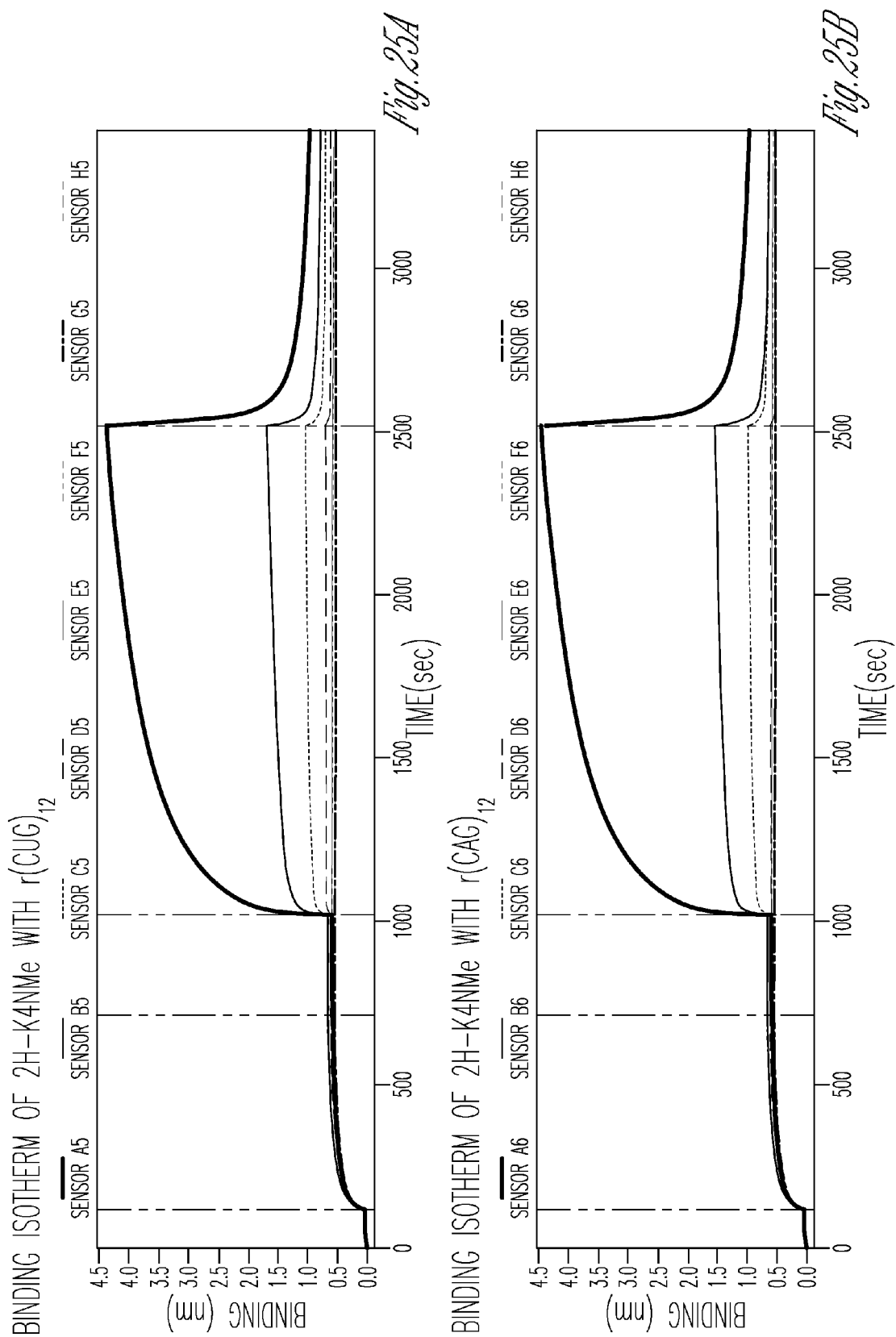

SEQUENCE LISTING

<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: A synthetic primer

<400> SEQUENCE: 1
gttcacaacc atctaaagca agatg                                         25

<210> SEQ ID NO 2
<211> LENGTH: 19
<212> TYPE: DNA
<213> ORGANISM: Artificial Sequence
<220> FEATURE:
<223> OTHER INFORMATION: A synthetic primer

<400> SEQUENCE: 2
gttgcatggc tggtgcagg                                                19

<210> SEQ ID NO 3
<211> LENGTH: 30
<212> TYPE: DNA
<213> ORGANISM: Artificial Sequence
<220> FEATURE:
<223> OTHER INFORMATION: A synthetic primer

<400> SEQUENCE: 3
cggggtacca aatgctgcag ttgactctcc                                    30

<210> SEQ ID NO 4
<211> LENGTH: 29
<212> TYPE: DNA
<213> ORGANISM: Artificial Sequence
<220> FEATURE:
<223> OTHER INFORMATION: A synthetic primer

<400> SEQUENCE: 4
ccgctcgagc cattcatgaa gtgcacagg                                     29

<210> SEQ ID NO 5
<211> LENGTH: 24
<212> TYPE: DNA
<213> ORGANISM: Artificial Sequence
<220> FEATURE:
<223> OTHER INFORMATION: A synthetic primer

<400> SEQUENCE: 5
tgaaggaata cctcacactc aagg                                          24

<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6
cacggaacac aaaggcactg                                            20

<210> SEQ ID NO 7
<211> LENGTH: 22
<212> TYPE: DNA
<213> ORGANISM: Artificial Sequence
<220> FEATURE:
<223> OTHER INFORMATION: A synthetic primer

<400> SEQUENCE: 7
ctcatggtcc tcaagatctc ac                                         22

<210> SEQ ID NO 8
<211> LENGTH: 20
<212> TYPE: DNA
<213> ORGANISM: Artificial Sequence
<220> FEATURE:
<223> OTHER INFORMATION: A synthetic primer

<400> SEQUENCE: 8
gggtcagtgc ctcagctttg                                            20

<210> SEQ ID NO 9
<211> LENGTH: 36
<212> TYPE: RNA
<213> ORGANISM: Artificial Sequence
<220> FEATURE:
<223> OTHER INFORMATION: A synthetic RNA sequence

<400> SEQUENCE: 9
cugcugcugc ugcugcugcu gcugcugcug cugcug                          36

<210> SEQ ID NO 10
<211> LENGTH: 36
<212> TYPE: RNA
<213> ORGANISM: Artificial Sequence
<220> FEATURE:
<223> OTHER INFORMATION: A synthetic RNA sequence

<400> SEQUENCE: 10
gcgcugcugc ugcugcugcu gcugcugcug cugcgc                          36

<210> SEQ ID NO 11
<211> LENGTH: 36
<212> TYPE: RNA
<213> ORGANISM: Artificial Sequence
<220> FEATURE:
<223> OTHER INFORMATION: A synthetic RNA sequence

<400> SEQUENCE: 11
gcgcagcagc agcagcagca gcagcagcag cagcgc                          36

<210> SEQ ID NO 12
<211> LENGTH: 28
<212> TYPE: RNA
<213> ORGANISM: Artificial Sequence
<220> FEATURE:

```
<223> OTHER INFORMATION: A synthetic RNA sequence

<400> SEQUENCE: 12
auauauauau augaaaauau auauauau                                          28

<210> SEQ ID NO 13
<211> LENGTH: 20
<212> TYPE: RNA
<213> ORGANISM: Artificial Sequence
<220> FEATURE:
<223> OTHER INFORMATION: A synthetic RNA sequence

<400> SEQUENCE: 13
gcgcgcgcga aagcgcgcgc                                                   20

<210> SEQ ID NO 14
<211> LENGTH: 36
<212> TYPE: RNA
<213> ORGANISM: Artificial Sequence
<220> FEATURE:
<223> OTHER INFORMATION: A synthetic RNA sequence

<400> SEQUENCE: 14
cugcugcugc ugcugcugcu gcugcugcug cugcug                                 36
```

MODULARLY ASSEMBLED SMALL MOLECULES FOR THE TREATMENT OF MYOTONIC DYSTROPHY TYPE 1

CROSS REFERENCE TO RELATED APPLICATIONS

This application is a U.S. national stage application filed under 35 U.S.C. §371 from International Application Ser. No. PCT/US2014/053520, which was filed Aug. 29, 2014, and published as WO 2015/031819 on Mar. 5, 2015, and which application claims the priority of U.S. provisional application Ser. No. 61/871,483, filed Aug. 29, 2013, which applications and publication are incorporated by reference as if reproduced herein and made a part hereof in their entirety, and the benefit of priority of each of which is claimed herein.

BACKGROUND

RNA is an important target for small molecule probes of function or lead therapeutics. Yet, very few RNAs have been exploited as such. Validated targets include ribosomal RNA,[1, 2] which constitutes 80-90% of total cellular RNA,[3-5] and riboswitches, that have known metabolite binders that can be mimicked to aid inhibitor design.[6, 7] Compounds targeting the ribosome and riboswitches have been extremely useful probes to help understand RNA function. One major challenge in RNA chemical biology is how to exploit other RNAs in the transcriptome similarly. This is a considerable challenge given the low cellular abundance of these RNAs [8] and the lack of lead small molecules.[9]

In an effort to exploit other potential RNA targets in the transcriptome with small molecules, we have developed a "bottom-up" strategy to design small molecules that bind an RNA of interest. That is, we define the small, discrete RNA secondary structural elements that are privileged for binding small molecules;[10,14] the interactions are then deposited into a database. The secondary structural elements in our selection studies are kept intentionally small such that they are likely components of larger cellular RNAs. The secondary structure of an RNA target is compared to our database of interactions, providing lead compounds. Leads can be optimized using various strategies including chemical similarity searching[15, 16] and/or modular assembly.[13, 17-22] One application of this strategy has been the rational design of bioactive small molecules that target the RNA that causes myotonic dystrophy-type 1 (DM1).[15, 17, 18]

DM1 is a presently incurable neuromuscular disease caused by a r(CUG) expansion, r(CUG)$^{exp}$, in the 3' untranslated region (UTR) of the dystrophia myotonica protein kinase (DMPK) mRNA.[23, 24] The RNA folds into a hairpin structure that displays regularly repeating 1×1 nucleotide internal loops (5'CUG/3'GUC motifs; FIG. 1)[25, 26] that are conformationally flexible.[8, 22] The loops are high affinity binding sites for muscleblind-like 1 protein (MBNL1), and sequestration of MBNL1 causes its inactivation and subsequent dysregulation of alternative pre-mRNA splicing.[28-31] Formation of the r(CUG)$^{exp}$-MBNL1 complex causes various disease-associated defects including (FIG. 1): (i) pre-mRNA splicing defects;[28, 32-34] (ii) formation of nuclear foci that consist of r(CUG)$^{exp}$-protein complexes;[35-37]; and, (iii) translational defects of DMPK mRNA due to poor nucleo-cytoplasmic transport.[38-40]

Since the root cause of DM1 is r(CUG)$^{exp}$, a variety of strategies have been employed to disrupt r(CUG)$^{exp}$-MBNL1 complexes, thus releasing MBNL1 and restoring regulation of alternative splicing. Oligonucleotides that target r(CUG)$^{exp}$ improve DM1-associated defects upon injection into DM1 mouse models.[33, 41, 42] Small molecules have also been developed that target r(CUG)$^{exp}$ including pentamidine, bis-benzimidazoles, naphthyl pyridines, and triazines.[13, 15, 17-19, 43-46] The most potent are modularly assembled compounds that target the repeating nature of r(CUG)$^{exp}$, binding multiple 5'CUG/3'GUC motifs simultaneously.[13, 17-19] These compounds are composed of a modular assembly scaffold that displays multiple copies of an RNA-binding module on a single chain.[13, 17-19]

SUMMARY

Transcriptomes provide a myriad of potential RNAs that could be the targets of therapeutics or chemical genetic probes of function. Cell permeable small molecules, however, generally do not exploit these targets, owing to the difficulty in the design of high affinity, specific small molecules targeting RNA. As part of a general program to study RNA function using small molecules, we designed bioactive, modularly assembled small molecules that target the non-coding expanded RNA repeat that causes myotonic dystrophy type 1 (DM1), r(CUG)$^{exp}$. Herein, we present a rigorous study to elucidate features in modularly assembled compounds that afford bioactivity.

Different modular assembly scaffolds were investigated including polyamines, α-peptides, β-peptides, and peptide tertiary amides (PTAs). Based on activity as assessed by improvement of DM1-associated defects, stability against proteases, cellular permeability, and toxicity, we discovered that constrained backbones, namely PTAs, are optimal. Notably, we determined that r(CUG)$^{exp}$ is the target of the optimal PTA in cellular models and that the optimal PTA improves DM1-associated defects in a mouse model. Biophysical analyses were employed to investigate potential sources of bioactivity. These investigations show that modularly assembled compounds have increased residence times on their targets and faster on rates than the RNA-binding modules from which they were derived; and faster on rates than the protein that binds r(CUG)$^{exp}$, the inactivation of which gives rise to DM1-associated defects. These studies provide information about features of small molecules that are programmable for targeting RNA, allowing for the facile optimization of therapeutics or chemical probes against other cellular RNA targets.

Herein, we describe detailed studies aimed at understanding features in modular assembly scaffolds that provide bioactivity. It is shown that the nature of the scaffold significantly affects potency and bioactivity. By studying different scaffolds including polyamines, α-peptides, β-peptides, and peptide-tertiary amides (PTAs), we determined that the PTA scaffold is optimal based on bioactivity in two different cellular assays, stability against proteases, cellular permeability, and toxicity. These studies define features that can be programmed into small molecules to afford bioactivity and can be applied to other potential RNA targets in the transcriptome.

In various embodiments, the invention provides a dimeric r(CUG)$^{exp}$ binding compound of formula (I)

wherein H is a group of formula

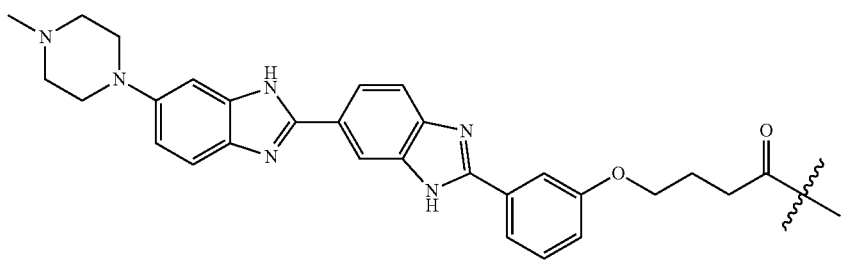

(H)

wherein a wavy line indicates a position of bonding, and wherein Y is a bifunctional linker comprising at least two primary or secondary amino groups, and optional further comprising additional amino, carboxamido, or peptidyl groups; or a pharmaceutically suitable salt thereof. More specifically, linker Y can be a 1,ω-diaminoalkane, optional further comprising additional amino, carboxamido, or peptidyl groups; for example Y can further comprise one or more α-peptidyl segment, β-peptidyl segment, polyamino segment, peptidyl tertiary amide segments, or any combination thereof.

The invention also can provide a method of disrupting the r(CUG)$_{12}$-MBNL1 complex, comprising administering an effective amount of a compound of the invention to a living mammalian cell. The living mammalian cell is in the body tissue of a human patient.

The invention also can provide a method of treatment of myotonic dystrophy type 1 in a human patient, comprising administering an effective amount of a compound of the invention to the patient.

BRIEF DESCRIPTION OF THE FIGURES

FIGS. 25(A)-(D) show the binding isotherms from surface plasmon resonance experiments for 2H-K4NMe with r(CUG)$_{12}$, r(CAG)$_{12}$, r(AU)$_{12}$, and r(CG)$_8$ RNA sequences, respectively.

DETAILED DESCRIPTION

The invention provides, in various embodiments, a dimeric r(CUG)$^{exp}$ binding compound of formula (1)

$$H\text{---}Y\text{---}H \tag{1}$$

wherein H is a group of formula

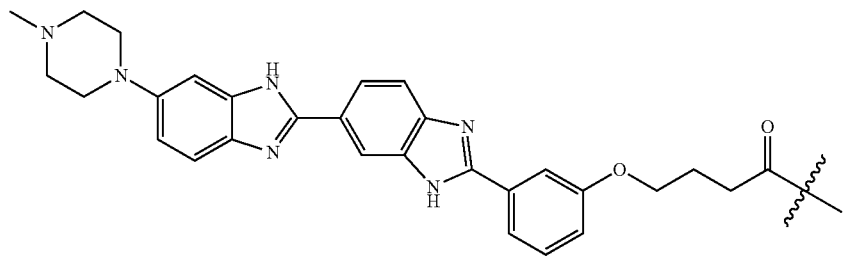

(H)

wherein a wavy line indicates a position of bonding, and wherein Y is a bifunctional linker comprising at least two primary or secondary amino groups, and optional further comprising additional amino, carboxamido, or peptidyl groups;
or a pharmaceutically suitable salt thereof. The bifunctional linker comprising the two reactive amino groups forms amide bonds with the respective carbonyl groups of the 2H units of formula 1.

More specifically, linker Y can be a 1,ω-diaminoalkane, optional further comprising additional amino, carboxamido, or peptidyl groups; for example Y can further comprise one or more α-peptidyl segment, β-peptidyl segment, polyamino segment, peptidyl tertiary amide segments, or any combination thereof.

By a 1,ω-diaminoalkane is meant an alkane bearing primary or secondary amino groups at both termini of a linear or branched alkane segment. When one or more additional amino group is present in the alkane, the linker Y is a polyamine. One or more carboxamido group, i.e., a group of formula C(=O)NR, wherein R is H or alkyl, e.g., (C1-C6)alkyl, can be present in the alkane segment. The term α-peptidyl segment as used herein refers to a residue or an oligomer of α-aminoacid residues, and the term β-peptidyl segment as used herein refers to a residue or an oligomer of β-aminoacid residues. A peptidyl tertiary amide segment refers to a residue or an oligomer of peptides bearing non-hydrogen substituents on their peptidyl amino groups.

More specifically, Y is selected from the group consisting of

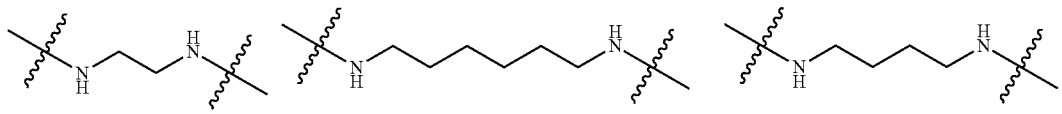

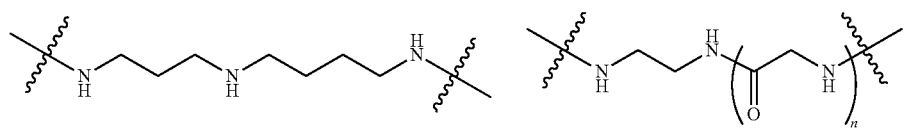

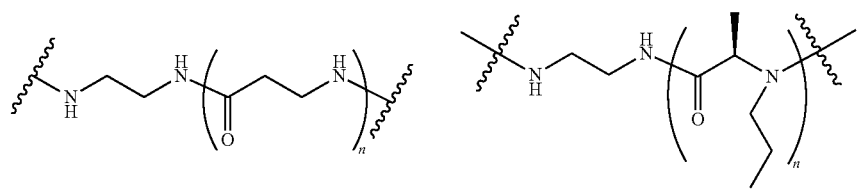

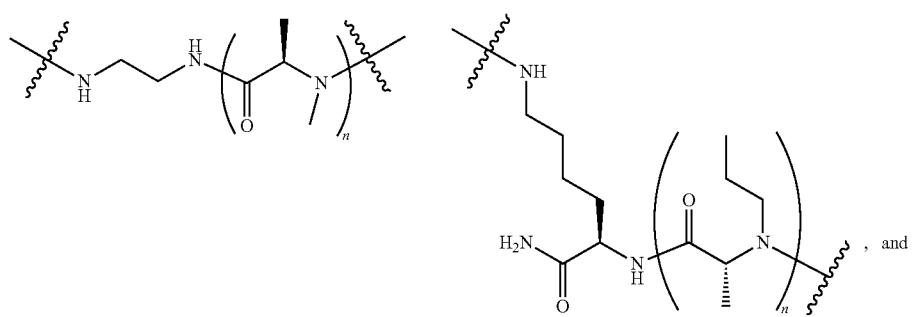

, and

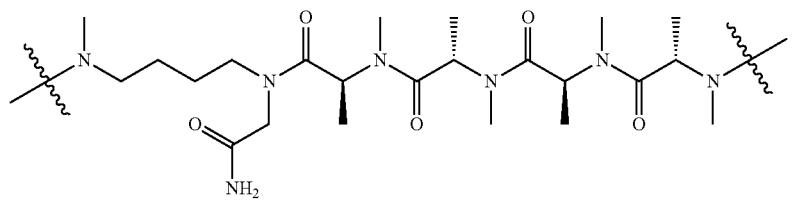

wherein wavy lines each indicate a point of bonding to a respective group H, and n is a whole number ranging from 1 to about 20.

For instance, the compound can be of formula

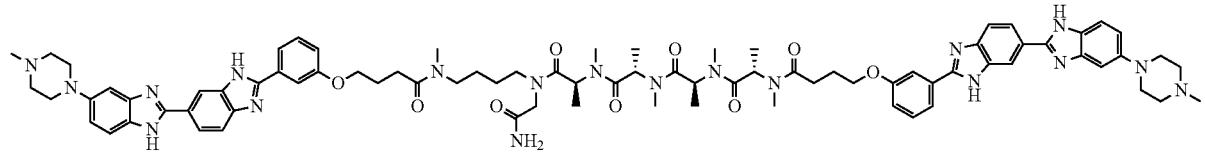

In various embodiments, the invention provides a method of disrupting the r(CUG)$_{12}$-MBNL1 complex, comprising administering an effective amount of a compound of the invention to a living mammalian cell. For example, the living mammalian cell can be in the body tissue of a human patient.

In various embodiments, the invention provides a method of treatment of myotonic dystrophy type 1 in a human patient, comprising administering an effective amount of a compound of the invention to the patient.

Design of Modularly Assembled Compounds.

Figure 1:
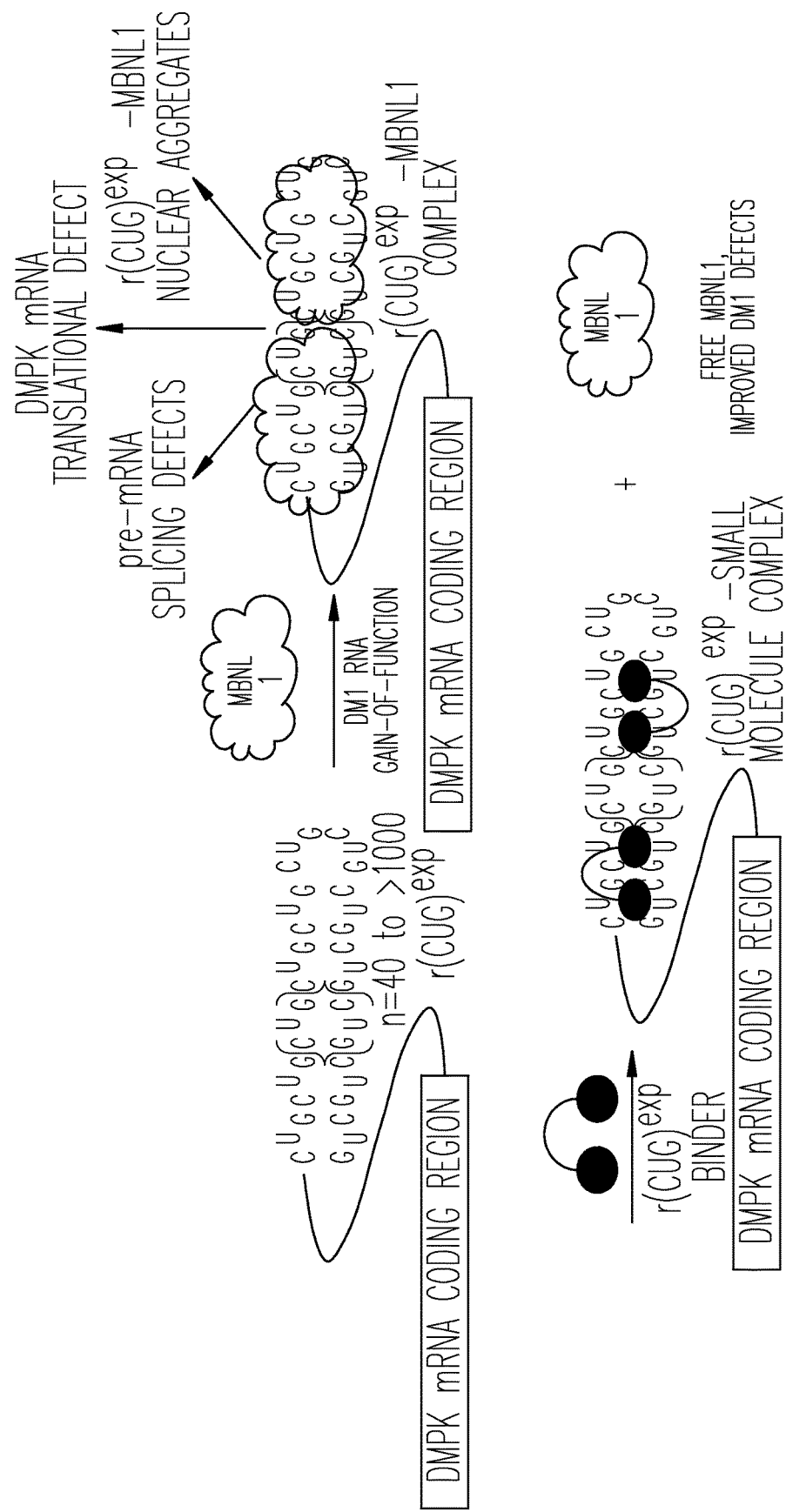
FIG. 1. Schematic for the disease pathology of DM1. An expansion of r(CUG) repeats (r(CUG)$^{exp}$; SEQ ID NO:9) located in the 3' UTR of the DMPK mRNA folds into a hairpin structure that binds and sequesters muscleblind-like 1 protein (MBNL1), a pre-mRNA splicing regulator. This decrease in functional MBNL1 results in dysregulation of alternative splicing of pre-mRNAs controlled by MBNL1. Other DM1-associated defects include decreased translation of the DMPK pre-mRNA and the formation of nuclear foci. Modularly assembled small molecules that target r(CUG)$^{exp}$ have the potential of improving defects by displacing MBNL1.
Figure 2:
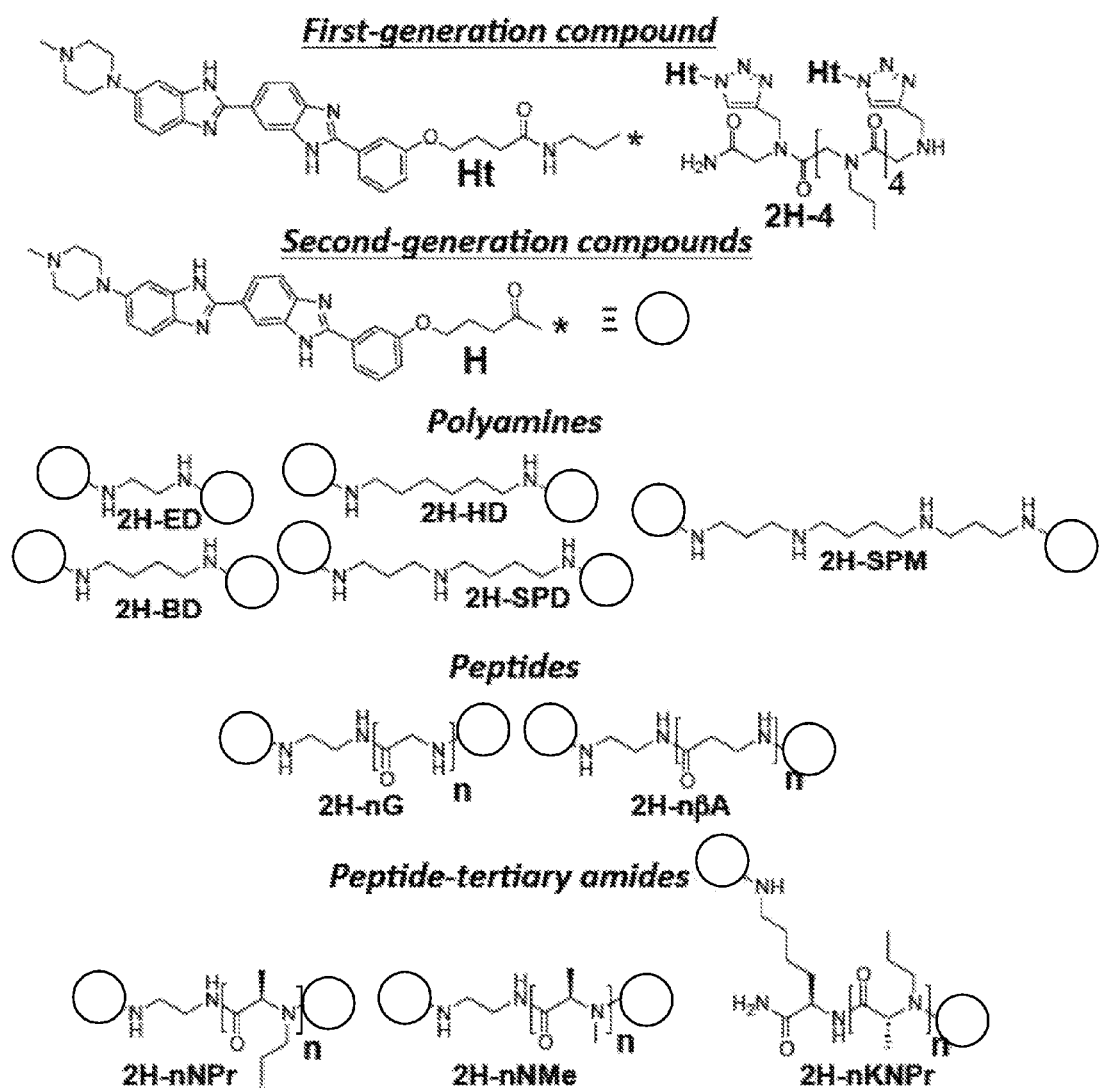
FIG. 2. Structures of first and second generation modularly assembled compounds that bind r(CUG)$^{exp}$. First generation compound 2H-4 contains a peptoid assembly scaffold. Classes of second generation compounds consist of polyamines, α-peptides, β-peptides, and peptide tertiary amides (PTAs).

We previously reported the design of modularly assembled compounds that inhibit the r(CUG)$^{exp}$-MBNL1 complex in vitro[13] and in vivo[18]. The compounds are comprised of a peptoid backbone that displays multiple copies of the bis-benzimidazole Ht separated by four spacing modules, or nH-4 compounds (FIG. 2). The 2H-4 compound is the most efficacious in DM1 cell culture models, improving various DM1-associated defects (FIG. 1).[18] In an effort to understand features in modularly assembled compounds that afford high affinity binding to r(CUG)$^{exp}$ and bioactivity, we designed and synthesized a series of second-generation compounds in which the assembly scaffold was varied. In particular, we studied polyamines, α-peptide, β-peptide, peptoid, and peptide tertiary amide (PTA) assembly scaffolds (FIG. 2). These scaffolds allowed us to study of the effect of (i) forming favorable interactions with a negatively charged phosphodiester backbone (polyamines); (ii) amide bond spacing (α- and β-peptides); (iii) N-alkylation (α- and β-peptides, peptoids, and PTAs); and, (iv) chirality of the C-α carbon atom (PTAs and peptoids).

PTAs are conformationally restricted, which could pre-organize them for recognition of an RNA target (FIG. 2). Since the most potent first generation compound was a dimer (2H-4),[18] we focused on dimers of each assembly scaffold. Compounds were synthesized on solid-phase resin and coupled to an Ht derivative that contains a carboxylate. (Ht binds 5'CUG/3'GUC, and thus is the RNA-binding module.[13]) it should be noted that all second-generation compounds are soluble in water at ≥10 mM concentration and ≥100 μM concentration in cell culture medium.

Second generation compounds are named 2H-X where 2H indicates two H RNA-binding modules and X is specific for each scaffold. The nomenclature for each scaffold is: (i) polyamines: 2H—P where P indicates the particular polyamine (ED is ethylenediamine; BD is butanediamine; HD is hexanediamine; SPD is spermidine; SPM is spermine); (ii) α-peptides: 2H-nG where n indicates the number of glycine residues; (iii) β-peptides: 2H-nβA where nβA indicates the number of β-alanine residues; and (iv) PTAs: 2H-nNX where NX indicates the particular N-alkylated spacing module and n indicates the number of modules.

Effect of the Assembly Scaffold on In Vitro Potency.

Figure 3:
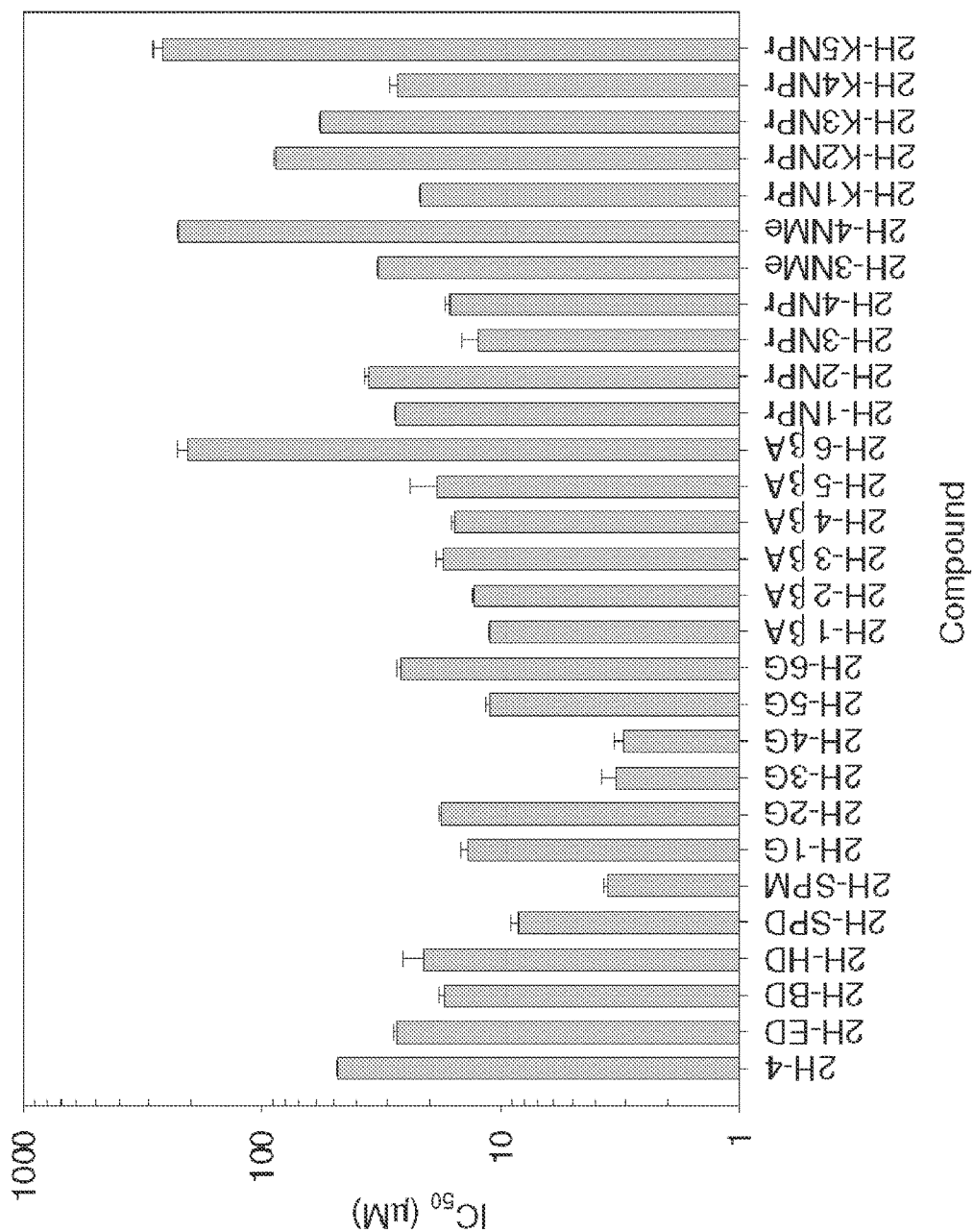
FIG. 3. IC$_{50}$'s of second generation modularly assembled compounds for disrupting the r(CUG)$_{12}$-MBNL1 complex. Potencies were determined using a TR-FRET assay.[15, 47] The most potent compounds from each class are: 2H-SPM, 2H-3G≈2H-4G, and 2H-3NPr, 2H-3NMe, and 2H-K4NPr (≈2H-K1NPr).

As mentioned above, DM1 is caused by sequestration of MBNL1 by r(CUG)$^{exp}$.[28, 32-37] Therefore, in vitro potency was determined by measuring displacement of MBNL1 from a r(CUG)$_{12}$-MBNL1 complex using a time-resolved FRET (TR-FRET) assay.[15, 47] Each dimeric compound disrupts the r(CUG)$_{12}$-MBNL1 complex with IC$_{50}$'s between ~3 and ~300 μM (FIG. 3). The most potent compounds are: 2H-SPM, 2H-3G, and 2H-4G. Polyamines and α-peptides (polyglycines) are on average more potent than PTAs and peptoids. This may be due to the presence of imino protons that can favorably interact with the phosphodiester backbone of RNA (FIG. 2).

The spacing between H RNA-binding modules affects in vitro potency by more than an order of magnitude in almost all scaffold classes (FIG. 3), as previously observed.[13, 19, 21] For example, 2H-SPM has an IC$_{50}$ of ~3 μM while 2H-ED has an IC$_{50}$ of ~30 μM. The most potent α-peptides are 2H-3G and 2H-4G (IC$_{50}$≈3 μM) while 2H-6G is the least potent (IC$_{50}$≈30 μM). Similar differences are observed for 2H-nβA, 2H-nNMe, and 2H-KnNPr. In summary, the most potent compound in each assembly scaffold class is: polyamines, 2H-SPM; peptides, 2H-3G≈2H-4G (only 2H-3G was further investigated); PTAs, 2H-3NPr, 2H-3NMe, and 2H-K4NPr.

Effect of the Assembly Scaffold on Proteolytic Stability.

We investigated the proteolytic stability of the most potent compound in each class by measuring its susceptibility to pronase digestion at pH 7.8 and pH 9.0 for 18 h.[48] The most proteolytically stable compound is 2H-SPM (no observed degradation) while 2H-3NMe is the least stable (completely degraded). Intermediate stability against pronase digestion was observed for the remaining compounds, see Table 1, below.

Proteolytic stability of second and third generation compounds was assessed using pronase as previously described.[3] Pronase is a group of ≥10 proteases isolated from Streptomyces griseus K-1. As such, proteolytic degradation was measured at two pH's, 7.8 and 9.0. Briefly, promise (1 unit) was added to the compound of interest (400 μM in 40 μL) in 1X Digestion Buffer (50 mM Tris-HCl, pH 7.8 or 9.0, and 10 mM CaCl$_2$), and the reaction was incubated at 37° C. for 18 h. Reactions were quenched by addition of 4 μL of 25% acetic acid, and the products of the pronase digestion were analyzed by HPLC. A linear gradient of 0-100% methanol in H$_2$O with 0.1% (v/v) TFA and a flow rate of 1 mL/min were employed. Results are summarized in Table 1.

TABLE 1

Proteolytic Activity of Selected Compounds With Respect to Pronase

| Compound | Pronase Degradation (pH 7.8) | Pronase Degradation (pH 9) |
|---|---|---|
| 2H-4 | ++ | ++ |
| 2H-SPM | + | + |
| 2H-3G | ++ | ++ |
| 2H-3NPr | ++ | ++ |

TABLE 1-continued

Proteolytic Activity of Selected Compounds With Respect to Pronase

| Compound | Pronase Degradation (pH 7.8) | Pronase Degradation (pH 9) |
|---|---|---|
| 2H-3NMe | +++ | +++ |
| 2H-K4NPr | ++ | ++ |
| 2H-K4NMe | ++ | ++ |
| 2H-K4H | +++ | +++ |
| 2H-K4iBu | +++ | +++ |
| 2H-K4 | ++ | ++ |

+ Pronase stable,
++ Intermediate Pronase stability,
+++ Pronase unstable

Effect of the Assembly Scaffold on Bioactivity.

Figure 4A:
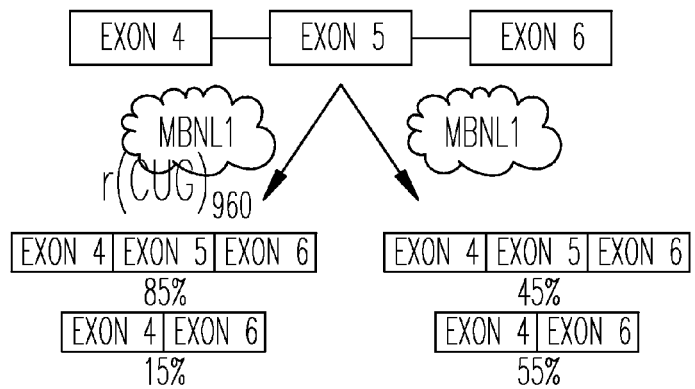
FIG. 4. Effect of the modular assembly scaffold on improving DM1-associated pre-mRNA splicing and translational defects. (A) Representation of the pre-mRNA splicing pattern observed for the cTNT mini-gene in the presence and absence of the DM1 mini-gene. Cells were treated post-transfection with 10 μM compound in growth medium. Alternative splicing was assessed by RT-PCR. (B) Quantification of RT-PCR analysis. Second generation compounds were compared to the parent compound, 2H-4. The most active compound in this assay is 2H-K4NPr, which has a PTA assembly scaffold (p=0.03; indicated by "8"). (C) Schematic of the cell model used to study translational defects. A stably transfected C2C12 cell line expresses firefly luciferase mRNA with r(CUG)$_{800}$ in the 3' UTR. r(CUG)$_{800}$ causes the transcript to be mostly retained in the nucleus and thus not efficiently translated. If a small molecule binds to r(CUG)$_{800}$ and displaces or inhibits MBNL1 binding, then the transcript is more efficiently exported from the nucleus and translated in the cytoplasm. (D) Quantification of the effect of second generation compounds on the DM1 translational defect as measured by luciferase activity. Compounds were tested at 10 μM and compared to the parent compound, 2H-4. Enhancement in luciferase activity is relative to untreated cells. (No change in luciferase activity is equal to 0%.) Second generation compounds were less effective than 2H-4 at improving translational defects. All second generation compounds have similar activities.
Figure 4B:
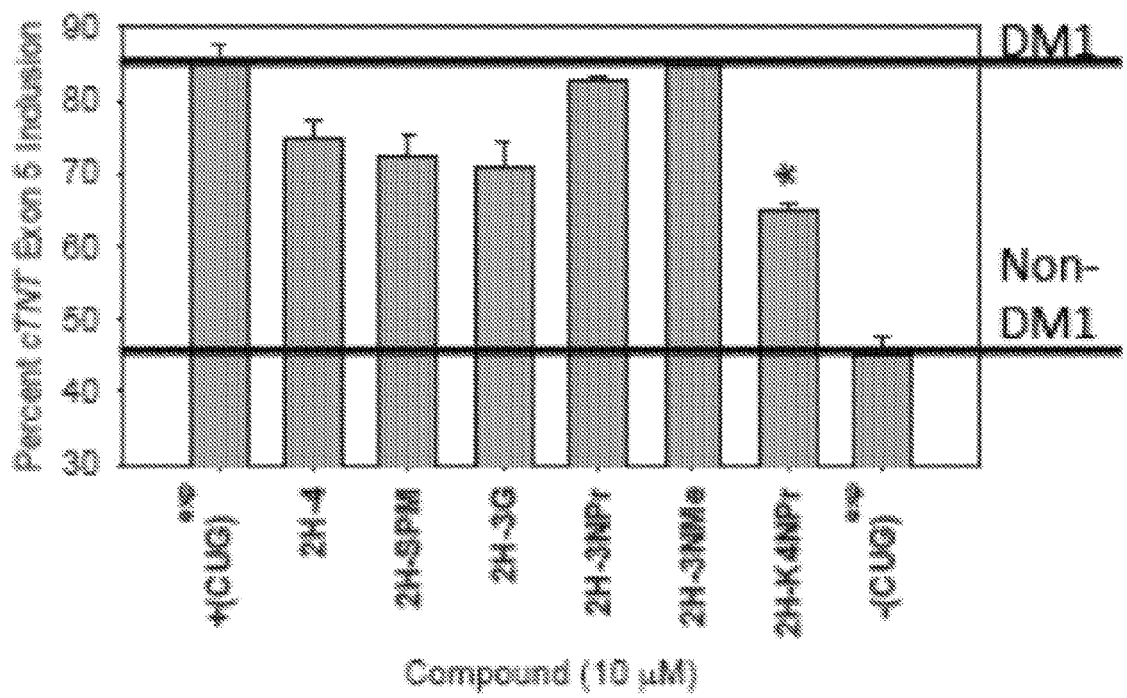

The best compound from each scaffold class was studied for improving DM1-associated defects in two DM1 cellular models (FIG. 4A & C and 8). As mentioned above, sequestration of MBNL1 by $r(CUG)^{exp}$ causes alternative pre-mRNA splicing defects.[28, 32-34] Therefore, we studied the MBNL-regulated alternative splicing of exon 5 of cardiac troponin T (cTNT) pre-mRNA.[49, 50] HeLa cells were transiently transfected with a DM1 mini-gene that encodes $r(CUG)^{exp}$ and a cTNT mini-gene[45, 51] followed by treatment with 10 μM compound. In the absence of $r(CUG)^{exp}$, the exon 5 inclusion rate is ~45% while in the presence of $r(CUG)^{exp}$, the exon 5 inclusion rate is ~85% (FIG. 4A & B). Interestingly, not all of the compounds tested improve the cTNT pre-mRNA splicing defect (FIG. 4B). There is some correlation between in vitro potency and improvement of splicing defects (FIGS. 3 & 4B). Based on in vitro potency, one would predict the following in vivo potencies: 2H-3G≈2H-SPM>2H-3NPr>2H-3NMe≈2H-K4NPr. Although these trends are generally observed, 2H-K4NPr is an outlier as it is actually the most potent in vivo for improving the cTNT-splicing defect.

Figure 4C:
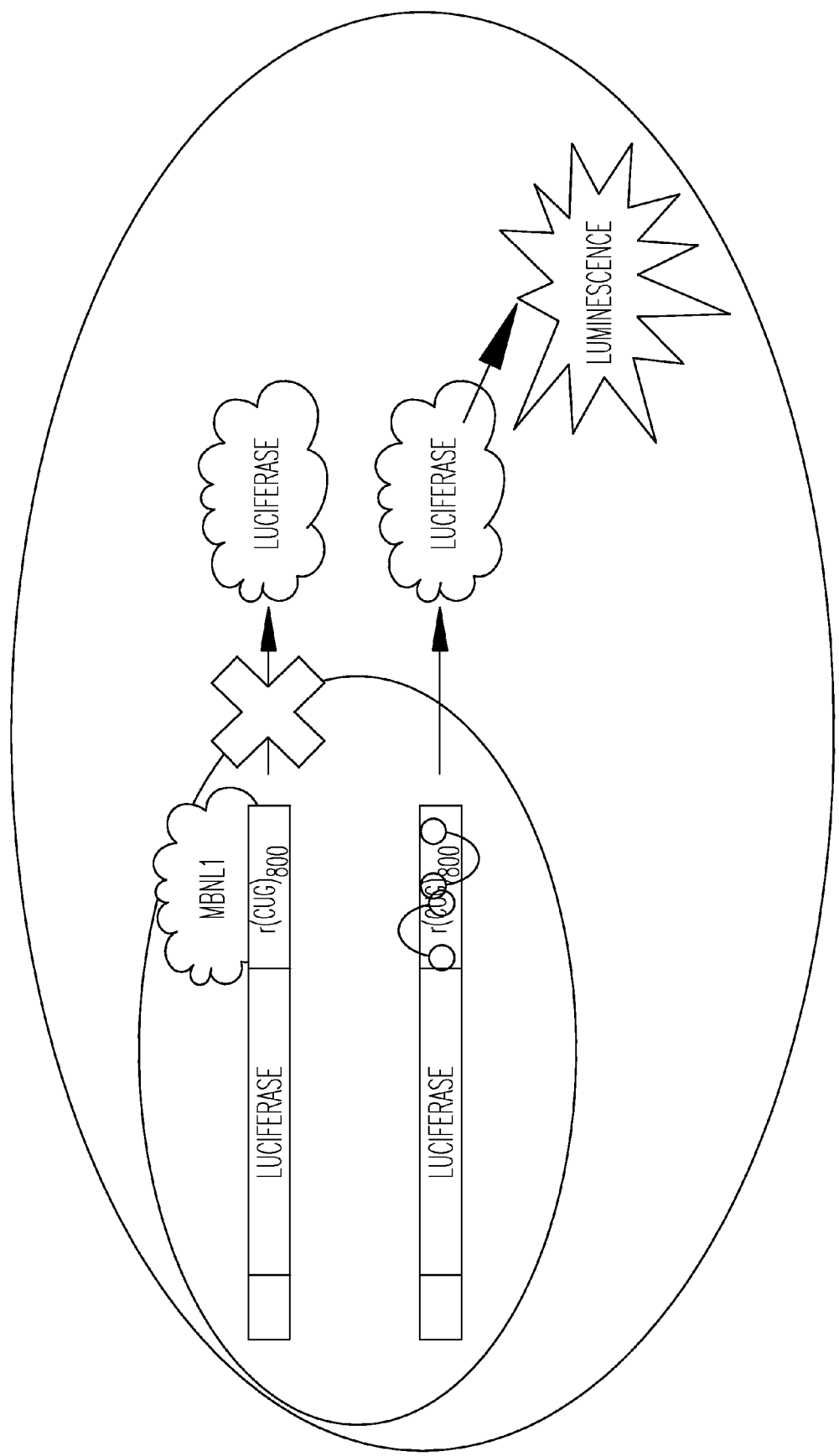
Figure 4D:
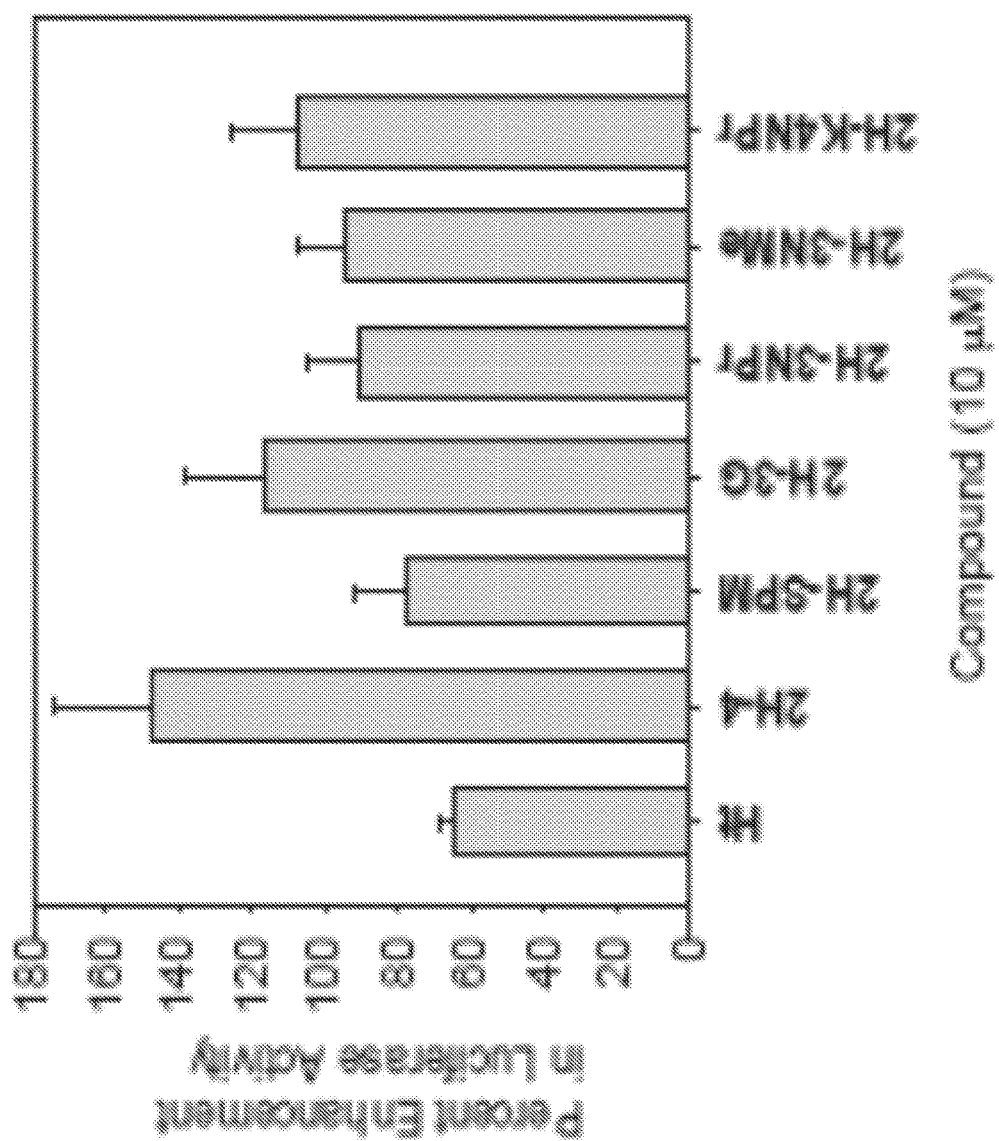

Next, compounds were studied for improving translational defects associated with DM1 (due to poor nucleocytoplasmic transport of $r(CUG)^{exp}$-containing transcripts).[33-40] In particular, a cellular model system was employed in which the C2C12 cell line stably expresses $r(CUG)_{800}$ embedded in the 3' UTR of firefly luciferase.[18] Akin to DMPK mRNA in DM1-affected cells, the expanded repeat impairs nucleocytoplasmic transport of luciferase mRNA and thus decreases luciferase expression. Compounds that bind $r(CUG)^{exp}$ and disrupt the $r(CUG)^{exp}$-MBNL1 complex may stimulate cytoplasmic transport of the luciferase mRNA and thus translation of luciferase (FIG. 4C). A significant increase in luciferase activity (and hence improvement of the DM1-associated translational defect) is observed for all compounds (FIG. 4D). There is little difference between the potencies of the compounds, with 2H-SPM having less improvement than the others. Importantly, the compounds do not affect luciferase activity of cells that stably express firefly luciferase mRNA without $r(CUG)_{800}$ (10 μM compound).

Effect of the Assembly Scaffold on Cellular Permeability and Toxicity.

Figure 9:
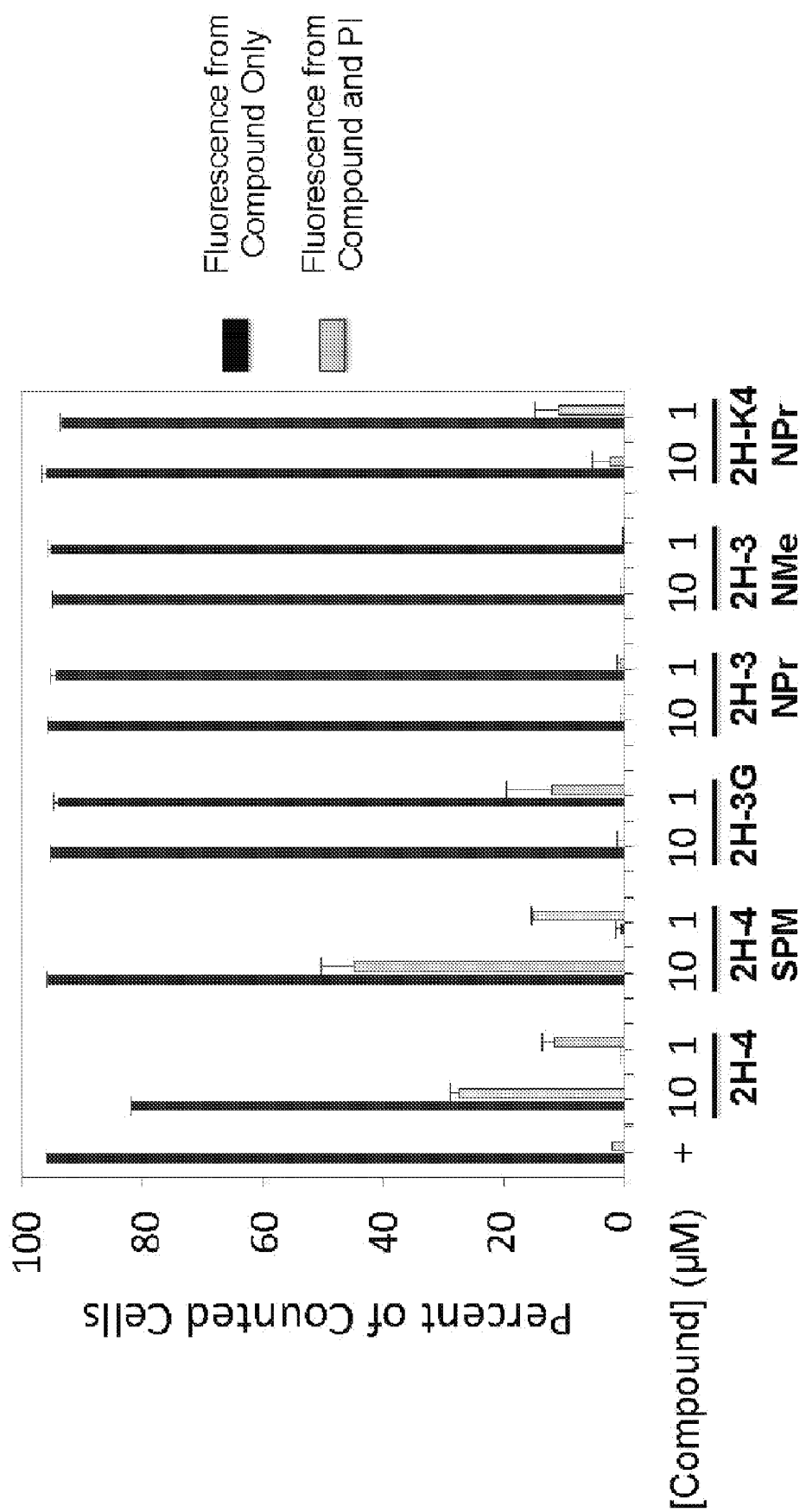
FIG. 9. Effect of assembly scaffold composition on cellular permeability and toxicity. HeLa cells were treated with 10 μM and 1 μM compound for 24 h. Toxicity was assessed by staining with propidium iodide (PI). All second generation compounds have improved permeability compared to the parent compound 2H-4. Compounds with peptide and PTA scaffolds had the greatest cell uptake with little toxicity. Gates for positive staining were created in relation to untreated, unstained cells; untreated, PI stained cells; and Hoechst 33258 (indicated by "+" in the plot) treated cells.

Next, we studied the effect of the assembly scaffold on cellular permeability and toxicity by flow cytometry (FIG. 9). Permeability was monitored by using the intrinsic fluorescence of the H module while toxicity was measured by propidium iodide (PI) staining. Cells were treated with 1 or 10 μM compound for 24 h and then analyzed. There is little difference in the cellular permeability or toxicity of second-generation compounds when dosed with 10 μM compound (FIG. 9), with the exception of 2H-SPM, which shows significant toxicity. Cellular permeability does not change at 1 μM dosage, except for 2H-SPM, which is reduced by 50%. Taken together, permeability and toxicity data suggest that polyamines may be sub-optimal modular assembly scaffolds. With the exception of 2H-SPM, all compounds are more cell permeable and less toxic than the parent compound, 2H-4, when cells are treated with 1 μM compound (FIG. 9). It has been shown that N-alkylated glycines such as peptoids and PTAs enter cells in greater amounts than peptides[52, 53] and that structurally constrained peptides are more cell permeable than their unstructured counterparts.[54-57]

Effect of N-alkyl Side Chains in PTAs.

Figure 5A:
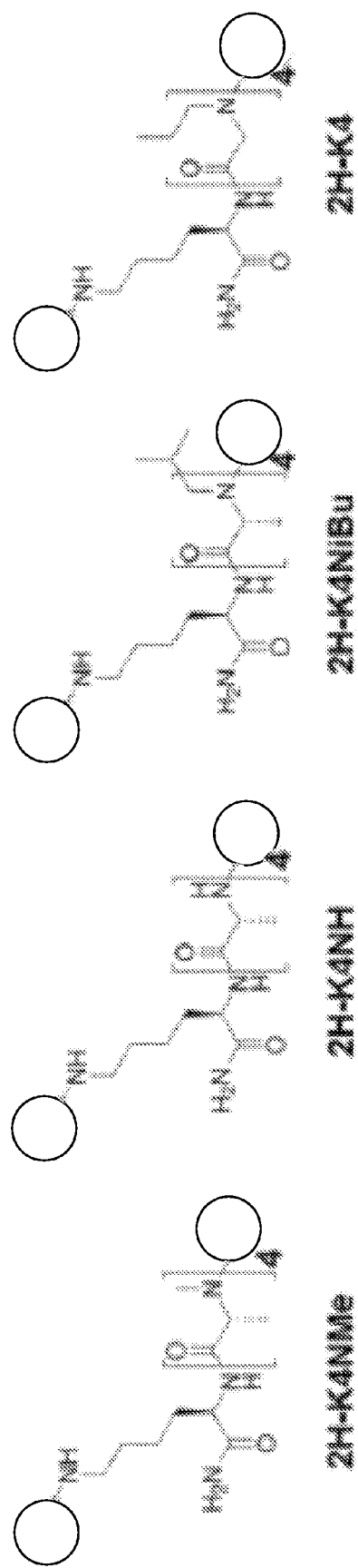
FIG. 5. Bioactivity of modularly assembled third generation compounds. Derivatives of the most bioactive second generation compound, 2H-K4NPr, were designed to investigate the effect of the substituents on the tertiary amide. (A) Structures of third generation compounds. Derivatives of 2H-K4NPr were prepared consisting of peptide, PTA and peptoid scaffolds. (B) IC$_{50}$'s of third generation modularly assembled compounds for disrupting the r(CUG)$_{12}$-MBNL1 complex. 2H-K4NMe, which has an N-methyl PTA scaffold, is the most potent. "*" indicates p<0.05 as determined by a two-tailed Student t-test. (C) Quantification of the improvement of DM1-associated alternative pre-mRNA splicing defects by third generation compounds. 2H-K4NPr improves dysregulation of the cTNT pre-mRNA splicing defect to the greatest extent. (D) Quantification of the improvement of DM1-associated translational defects by third generation compounds. Compounds demonstrated comparable activity to the parent compound, 2H-4. (E) Cellular permeability and toxicity of third generation modularly assembled compounds. "+" indicates Hoechst 33258, which was employed as a positive control for gating.

Considering all in vivo data, the optimal compound is 2H-K4NPr (FIGS. 3, 4, and 9). It most effectively improves splicing defects (FIG. 4B), has comparable activity for improving translational defects (FIG. 4D), is highly cell permeable and has low toxicity (FIG. 9), and is proteolytically (and likely metabolically[48]) stable. Therefore, we investigated the impact of the spacing module in 2H-K4NPr on bioactivity. Specifically, the influences of N-alkylation and α-carbon substitution were studied (FIG. 5A). Previous studies have shown that the spacing module affects affinity, potency, cellular permeability, and localization.[20]

Figure 5B:
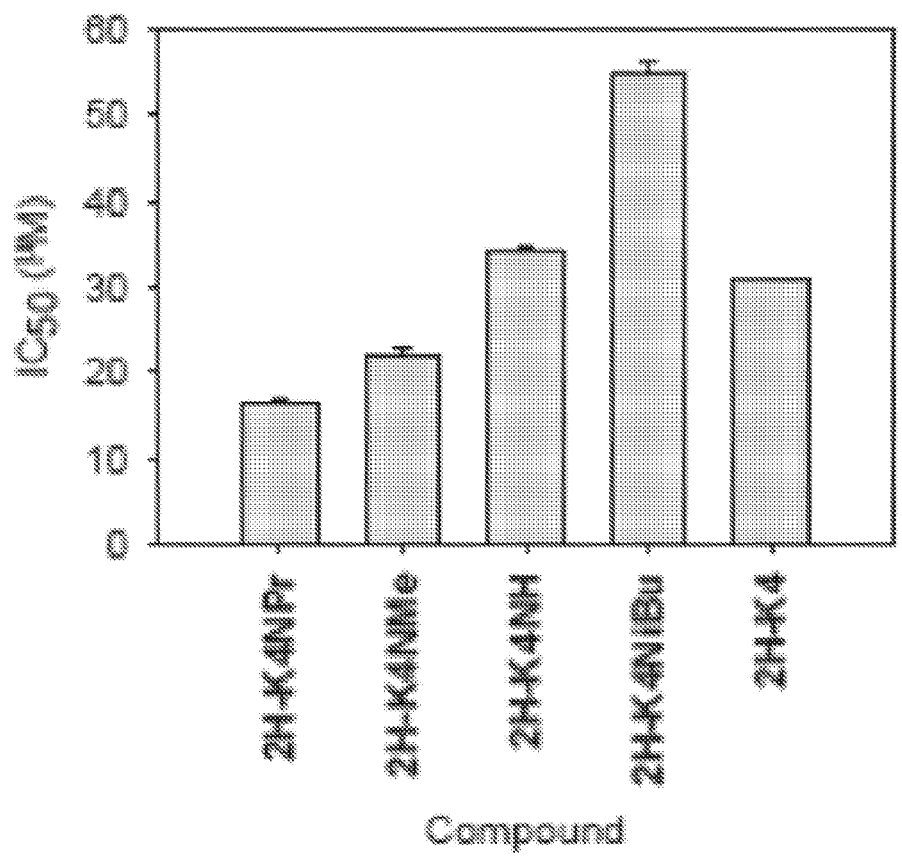

In vitro potencies were determined using the TR-FRET assay described above. $IC_{50}$ values ranged from 20 to 55 μM. The N-methyl PTA, 2H-K4NMe, is most potent while 2H-K4NiBu is least potent (FIG. 5B). This suggests that bulky substituents may hinder tight association between $r(CUG)_{12}$ and the small molecule. Interestingly, 2H-K4NH and 2H4NiBu are proteolytically unstable (Table 1).

Figure 5C:
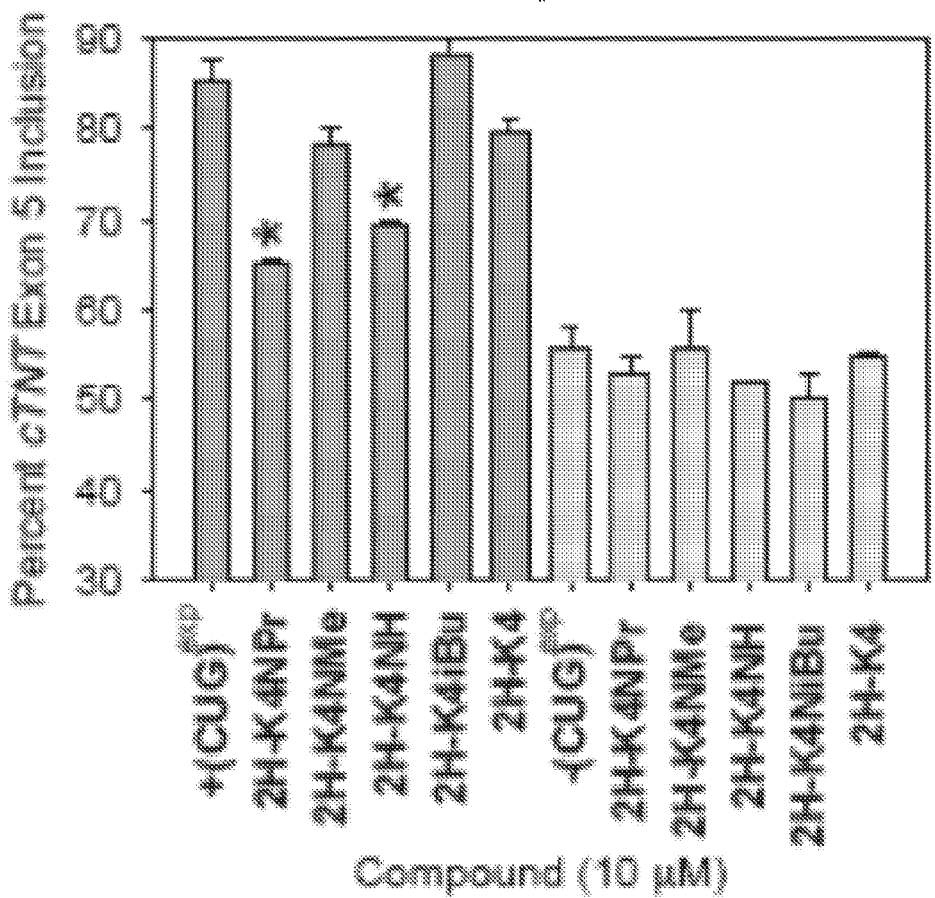
Figure 5D:
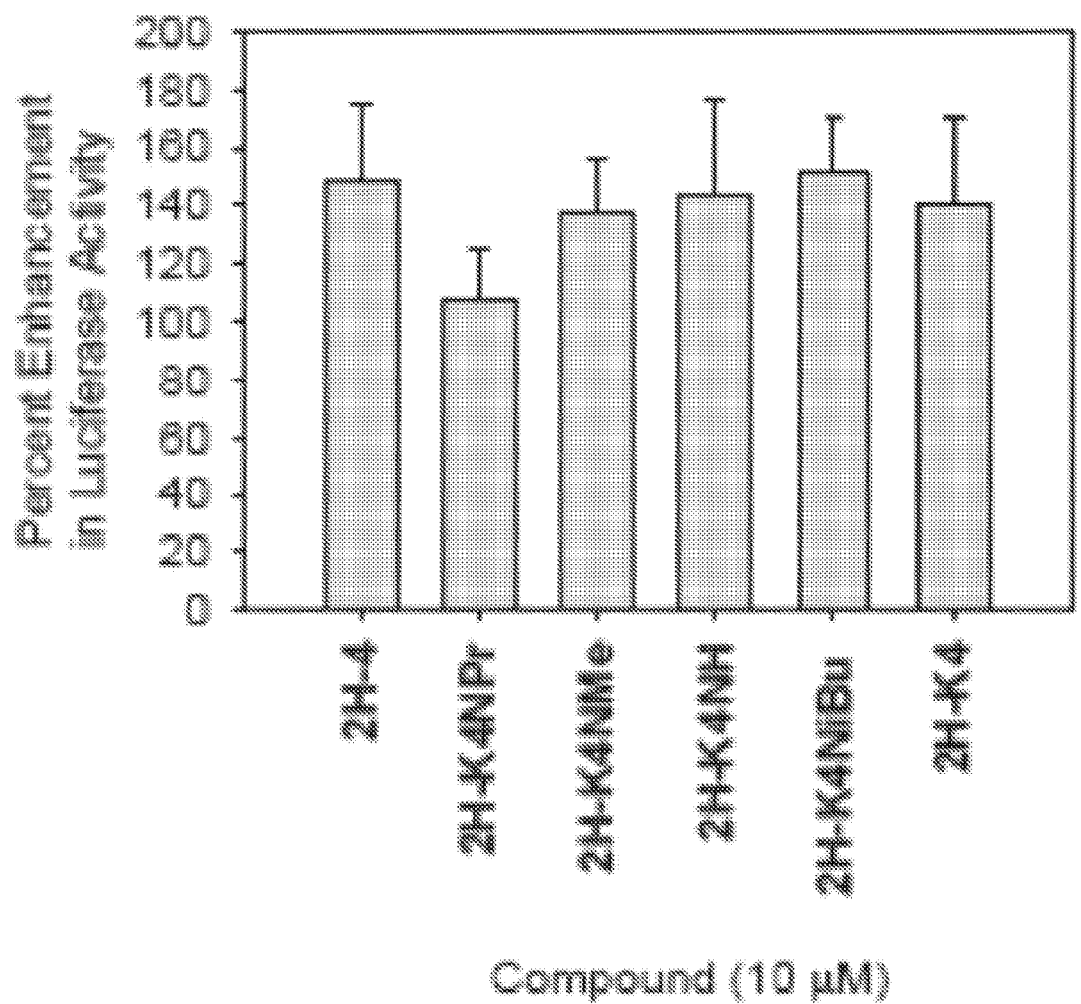
Figure 5E:
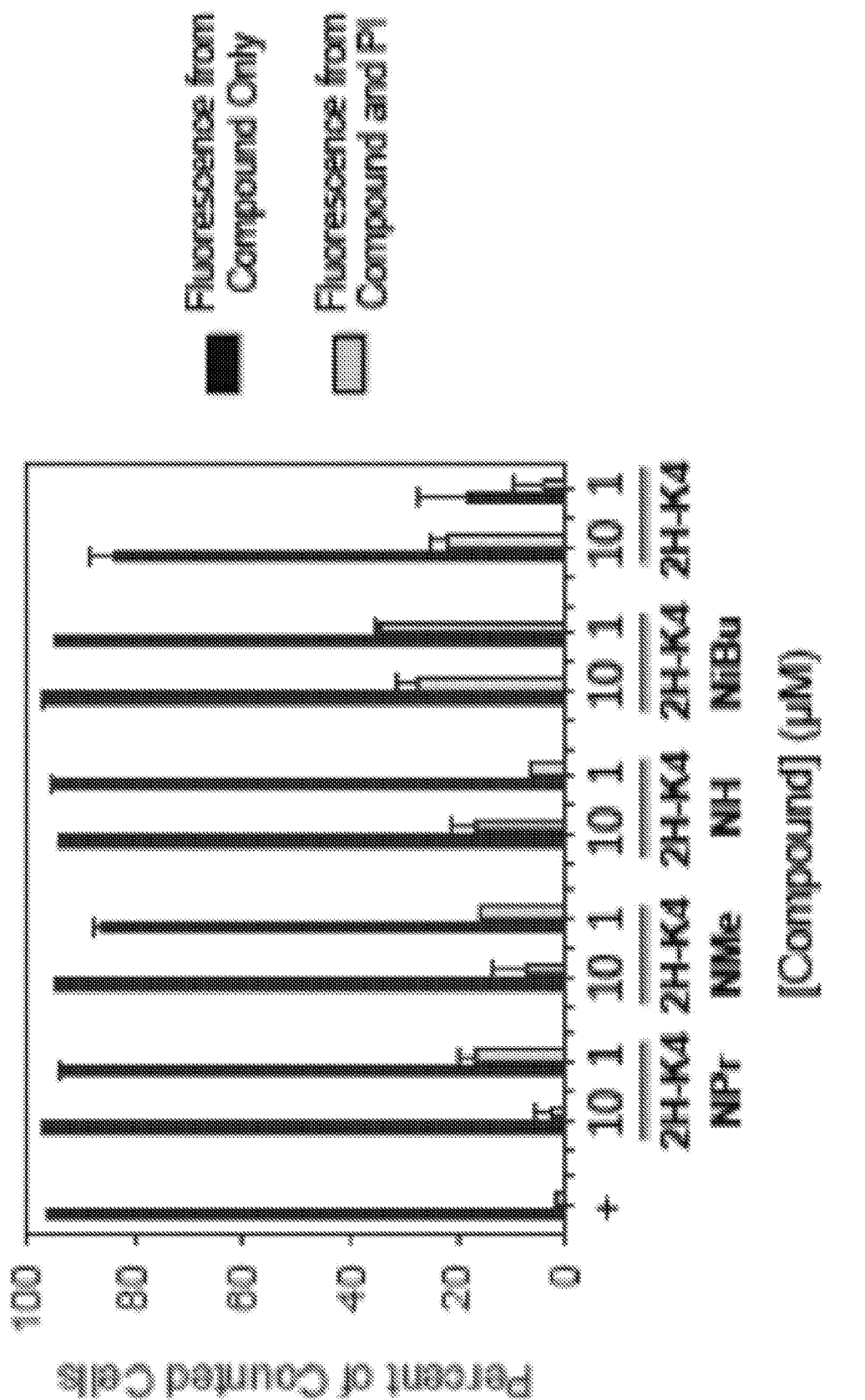

The compounds were assessed for improving DM1-associated pre-mRNA splicing defects when cells are dosed at 10 μM. The most efficacious compounds are the parent 2H-K4NPr and 2H-K4NH (no tertiary amide) followed by 2H-K4NMe and 2H-K4 (no substituent on the α-C); 2H-K4iBu is inactive. The 2H-K4NPr derivatives were also evaluated for improving translational defects using the luciferase reporter system. All derivatives significantly increase luciferase expression to a similar extent when cells are treated with 10 μM compound. Next, the cellular permeability and toxicity of each 2H-K4NPr derivative were determined via flow cytometry (FIG. 5E). As observed for second-generation compounds, there is little difference in permeability when cells are dosed with 10 μM compound with the exception of 2H-K4, a peptoid. A marked difference is observed for 2H-K4 and third generation compounds at the 1 μM dosage as the other derivatives (peptides and PTAs) are ~4 times more permeable. In general, little toxicity is observed for 2H-K4NPr derivatives with the exception of 2H-K4NiBu, which has significant toxicity at both 1 and 10 μM, and 2H-K4, which shows some toxicity when cells are treated with 10 μM compound. (FIG. 5E).

In summary, iBu substitution is disadvantageous for bioactivity, rendering the compound inactive in both cellular assays (FIG. 5C & D) and increasing cellular toxicity (FIG. 5E). Substitution of Pr with H or Me is better tolerated, although Me substitution decreases improvement of splicing defects (FIG. 5C). In contrast, 2H-K4NH has comparable activity as 2H-K4NPr as assessed by restoring pre-mRNA splicing patterns. Cellular permeability and toxicity are similar for 2H-K4NPr, 2H-K4NMe, and 2H-K4NH. Removal of the methyl group on the α-carbon, affording 2H-K4, negatively affects cellular permeability (FIG. 5E).

Further Analysis of 2H-K4NPr and 2H-K4NMe.

Figure 26:
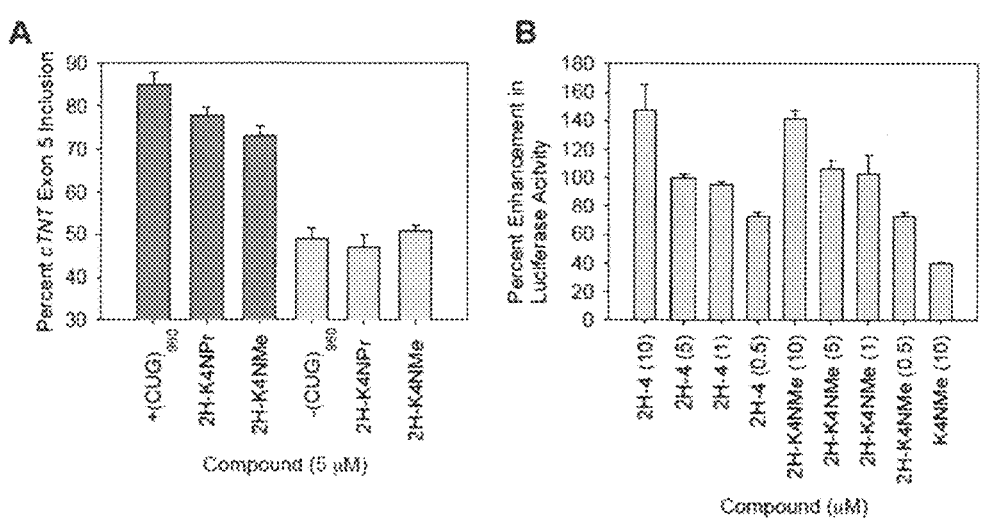
FIG. 26 shows a graphic comparison of the bioactivity of the bioactivity of 2H-K4NMe and 2H-K4NPr. (A) Quantification of RT-PCR analysis comparing second and third generation compounds for improving DM1-associated pre-mRNA splicing defects. There is little difference between second generation compound 2H-K4NPr and the third generation compound 2H-K4NMe at 5 μM. (B) Plot comparing luciferase activity related to improvement in DM1-associated translational defects between 2H-4 and 2H-K4NMe. K4NMe is the unconjugated scaffold (no RNA-binding modules).

We further investigated 2H-K4NPr and 2H-K4NMe based on their abilities to improve DM1-associated defects and because of their greater cell permeabilities (FIG. 5E) and proteolytic/metabolic stabilities (Table 1) than 2H-K4NH and 2H-K4. First, a dose response for improvement of pre-mRNA splicing defects was measured. Both compounds improve the cTNT splicing defect at 5 μM but not at 1 μM. Interestingly, 2H-K4NMe is slightly better than 2H-K4NPr at this concentration (FIG. 26). Neither compound affects cTNT splicing in cells that do not express $r(CUG)^{exp}$.

A dose response for improving translational defects was also completed for 2H-K4NMe. Significant activity was observed when cells were treated with as little as 1 μM compound (FIG. 26). Both 2H-K4NPr and 2H-K4NMe appear to improve alternative pre-mRNA splicing and translational defects at concentrations somewhat less than their in vitro $IC_{50}s$. These observations could be due to: (i) in vitro and in vivo assays measure very different phenomena: inhibition of the r(CUG)-MBNL1 interaction (in vitro) as compared to the activity of free MBNL1 (in vivo); (ii) a small effect on the translational defect is also observed for the PTA backbone (K4NMe; FIG. 26); and (iii) a recent study by Jog et al. reported that once a critical threshold of MBNL1 concentration is achieved, relatively small changes in the amount of active MBNL1 significantly affects the number and severity of splicing defects.[53] For example, when MBNL1 levels are unaffected, the percentage of cTNT exon 5 inclusion is 49.5%. When MBNL1 levels are decreased by 79%, 87%, 97%, and 98% via siRNA knockdown, the percentages of exon inclusion are 48.2% (no change as compared to cells treated with a scrambled siRNA), 54.3%, 81.5%, and 88.4%.[58] It should be noted that these effects are unique for each pre-mRNA substrate.[58] Taking together activity, stability, toxicity, and ease of synthesis, 2H-K4NMe is more ideal than 2H-K4NPr.

Additional control experiments were completed with 2H-K4NMe. To ensure that alternative splicing of pre-mRNAs not regulated by MBNL1 are unaffected, we studied the alternative splicing of pleckstrin homology domain containing, family H member 2 (PLEKHH2) using a minigene construct.[45] Splicing of PLEKHH2 was not affected at 10 μM, demonstrating 2H-K4NMe's selectivity for $r(CUG)^{exp}$ and alternative pre-mRNA splice events regulated by MBNL1. Moreover, the unconjugated PTA backbone, K4NMe, shows little activity in the translational assay (FIG. 26).

The binding of 2H-K4NMe to various RNAs including $r(CUG)_{12}$, $r(CAG)_{12}$, $r(AU)_{12}$ and $r(GC)_8$ was studied by surface plasmon resonance (SPR) spectrometry. The effect of assembly scaffold composition on cellular permeability and toxicity was examined. HeLa cells were treated with 10 μM and 1 μM compound for 24 h. Toxicity was assessed by staining with propidium iodide (PI). All second generation compounds have improved permeability compared to the parent compound 2H-4. Compounds with peptide and PTA scaffolds had the greatest cell uptake with little toxicity. Gates for positive staining were created in relation to untreated, unstained cells; untreated, PI stained cells; and Hoechst 33258 treated cells. In summary, 2H-K4NMe is selective for $r(CUG)_{12}$ by ~30-100-fold over the other RNAs studied (Table 2). In general, it has a faster association rate ($k_{on}$) and a slower dissociation rate ($k_{off}$) when binding to $r(CUG)_{12}$ compared to the other RNAs.

The kinetic parameters for 2H-K4NMe binding to $r(CUG)_{12}$ show that this compound has advantages over the monomeric RNA binding module and MBNL1 (Table 2).

TABLE 2

Characterization of the ligands binding to various RNAs as assessed by SPR.[a]

| RNA | $k_{off}(1)$ ($s^{-1}$) | $k_{off}(2)$ ($s^{-1}$) | $k_{on}(1)$ ($M^{-1} s^{-1}$) | $k_{on}(2)$ ($M^{-1} s^{-1}$) | $K_{obs}(1)$ (M) | Selectivity for $r(CUG)_{12}$ |
|---|---|---|---|---|---|---|
| 2H—K4NMe | | | | | | |
| $r(CUG)_{12}$[b] | $3.43 \times 10^{-3}$ | $5.00 \times 10^{-2}$ | $2.61 \times 10^5$ | $1.87 \times 10^3$ | $1.31 \times 10^{-8}$ | — |
| $r(CAG)_{12}$[b] | $6.95 \times 10^{-2}$ | $8.47 \times 10^{-2}$ | $8.38 \times 10^4$ | $1.63 \times 10^3$ | $8.29 \times 10^{-7}$ | 63 |
| $r(AU)_{12}$[b] | $1.65 \times 10^{-2}$ | $3.59 \times 10^{-1}$ | $4.13 \times 10^4$ | $1.98 \times 10^4$ | $4.00 \times 10^{-7}$ | 30 |
| $r(GC)_8$[b] | $8.22 \times 10^{-2}$ | $1.05 \times 10^{-1}$ | $5.86 \times 10^4$ | $2.48 \times 10^4$ | $1.40 \times 10^{-6}$ | 107 |
| 2H—K4NMeS | | | | | | |
| $r(CUG)_{12}$[b] | $6.00 \times 10^{-2}$ | $4.20 \times 10^{-2}$ | $2.73 \times 10^4$ | $1.44 \times 10^5$ | $2.2 \times 10^{-6}$ | — |
| H monomer | | | | | | |
| $r(CUG)_{12}$[c] | $3.69 \times 10^{-2}$ | — | $1.76 \times 10^4$ | — | $2.10 \times 10^{-6}$ | — |
| MBNL1 | | | | | | |
| $r(CUG)_{12}$[c] | $2.03 \times 10^{-3}$ | — | $3.28 \times 10^3$ | — | $6.19 \times 10^{-7}$ | — |

[a] The standard deviations for each of the measurements is ≤±10% and the secondary structures of the RNAs are provided in FIG. S-5.
[b] Data were fit best to a two component binding isotherm.
[c] Data were fit best to a one component binding isotherm.

For example, H binds $r(CUG)_{12}$ with a $K_d$ of 2000 nM, or 15-fold weaker than 2H-K4NMe. Previous studies show that 2H-4 only had an affinity bonus of 1.5-fold compared to monomer.[13] The increased affinity of 2H-K4NMe could be due to improved interactions of the PTA scaffold with the RNA or to the more pre-organized nature of the PTA backbone. PTAs have limited flexibility due to 1,3-allylic strain introduced by the substituents on both the α-carbon and the imino nitrogen and thus sample less conformational space when finding the optimal binding mode for $r(CUG)_{12}$.

Figure 10:
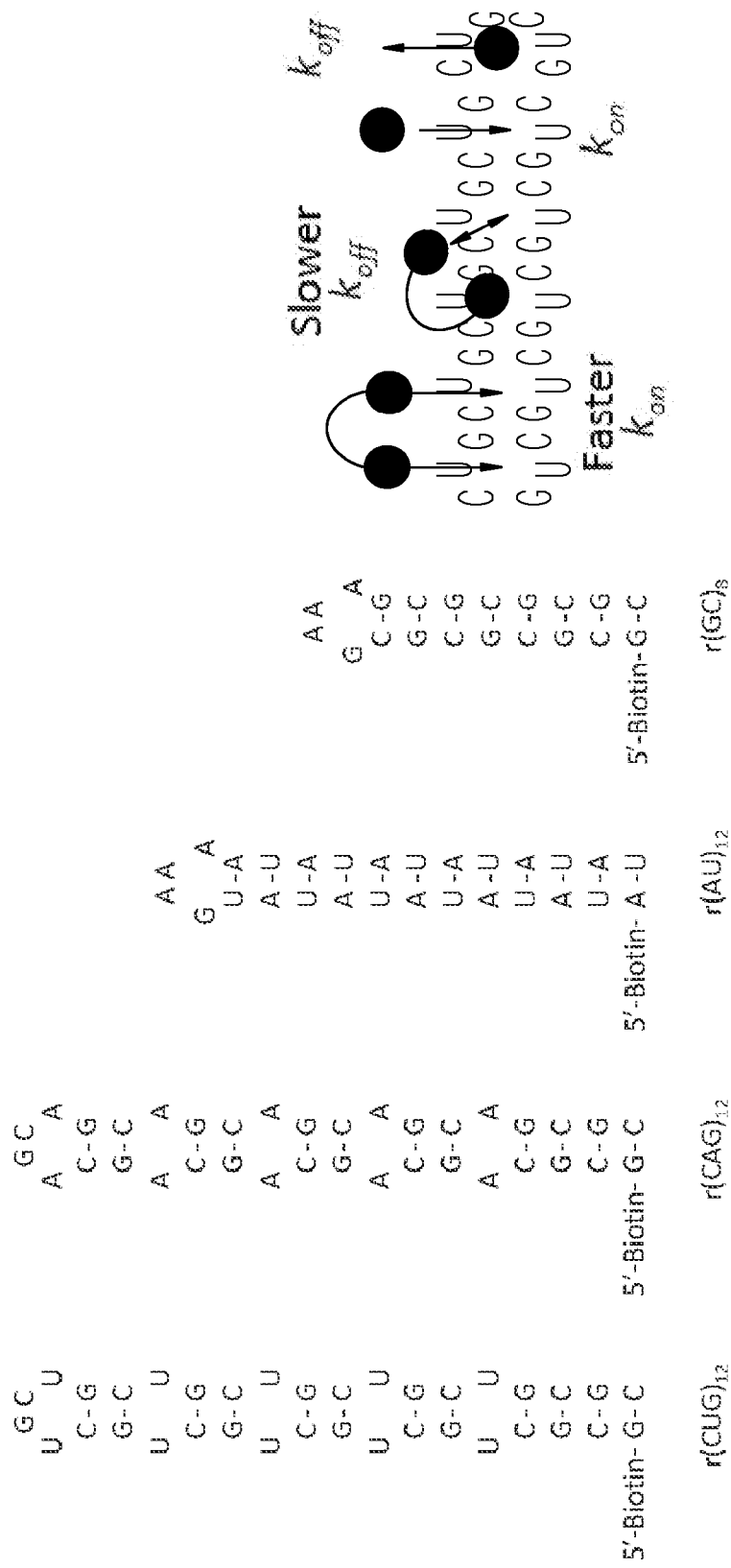
FIG. 10. Studying the kinetics of small molecule binding to RNA targets. Top, the secondary structures of the RNAs that were used in the SPR experiments to study the binding of small molecules to RNA target (SEQ ID Nos: 10-14). Bottom, a model for the increased $k_{on}$ and slower $k_{off}$ observed for modularly assembled small molecules due to a hinge effect.

The secondary structures of the RNAs used in these studies are given in FIG. 10. Additionally, the $k_{on}$ and $k_{off}$ rates are 10-fold faster and 10-fold slower for 2H-K4NMe than H, suggesting a hinge effect (FIG. 10) provides benefits for both the rates of complex formation and complex dissociation for modularly assembled compounds. 2H-K4NMe binds 5-fold more tightly to $r(CUG)_{12}$ than MBNL1 does. High affinity binding is advantageous for compounds that target $r(CUG)^{exp}$ as lower concentrations of compound are likely to be required for bioactivity, thus minimizing potential non-specific effects at efficacious doses. 2H-K4NMe also has kinetic advantages for binding r(CUG)$_{12}$ over MBNL1 as its on rate is 79-fold faster than MBNL1's (Table 2).

These binding kinetic observations may be due to the nature in which the small molecule and MBNL1 bind to RNA targets. As a regulator of alternative splicing, MBNL1 must interact specifically with RNA and does so via four zinc finger (ZnF) domains. A crystal structure of the ZnF3/4 domain complexed with two copies of single stranded r(CGCUGU) was recently reported.[59] Both zinc fingers interact with one molecule of RNA with ZnF3 forming contacts to the 5'GC step and ZnF4 forming contacts to 5'GCU. The RNA molecules are oriented antiparallel to each other. These results suggest that MBNL1 binding induces a chain-reversal trajectory and unzipping of the bound RNA. It is likely that MBNL1 opens the r(CUG) hairpin stem to afford two single stranded regions, which is supported by the fact that MBNL1 binds weakly to fully base-paired RNAs.[60] The increased on rate for the designer small molecule onto r(CUG)$^{exp}$ may be a consequence of such molecular recognition. That is, the small molecule binds the native hairpin structure of r(CUG)$^{exp}$ and stabilizes it whereas MBNL1 initially interacts with r(CUG)$^{exp}$, then disrupts or remodels the hairpin structure to afford the final bound conformation.

Identifying the Cellular Targets of 2H-K4NMe.

Figure 6:
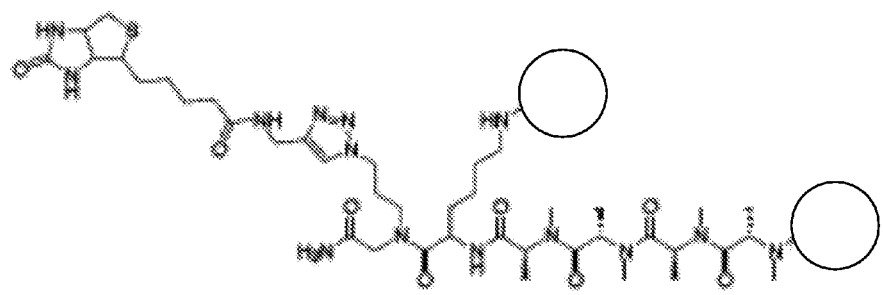
FIG. 6: Pull down experiments to identify the cellular RNA targets of designer small molecule 2H-K4NMe-Biotin. Top, structure of the compound that was anchored onto streptavidin functionalized agarose beads to provide an affinity matrix. Bottom, left, SYBR gold stained denaturing agarose gel. Bottom right, Northern blot of the SYBR gold stained gel with a probe for r(CUG)$^{exp}$. Lane 1, 1 Kb ladder; the top four bands (from top to bottom) are; 3 Kb, 2 Kb, 1.5 Kb, and 1 Kb; Lane 2, total RNA harvested from cells; Lane 3, empty; Lane 4, pull down by using 5'-Biotin d(CAG)$_{10}$; Lane 5, K4NMe-Biotin bound fraction (control small molecule that should not bind r(CUG)$^{exp}$); Lane 6, 2H-K4NMe-Biotin bound fraction; Lane 7, final wash from resin prior to elution of the bound RNA froth lane 6.
Figure 6:
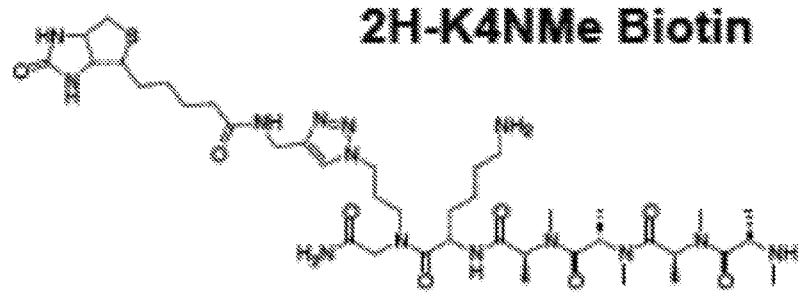
Figure 6:
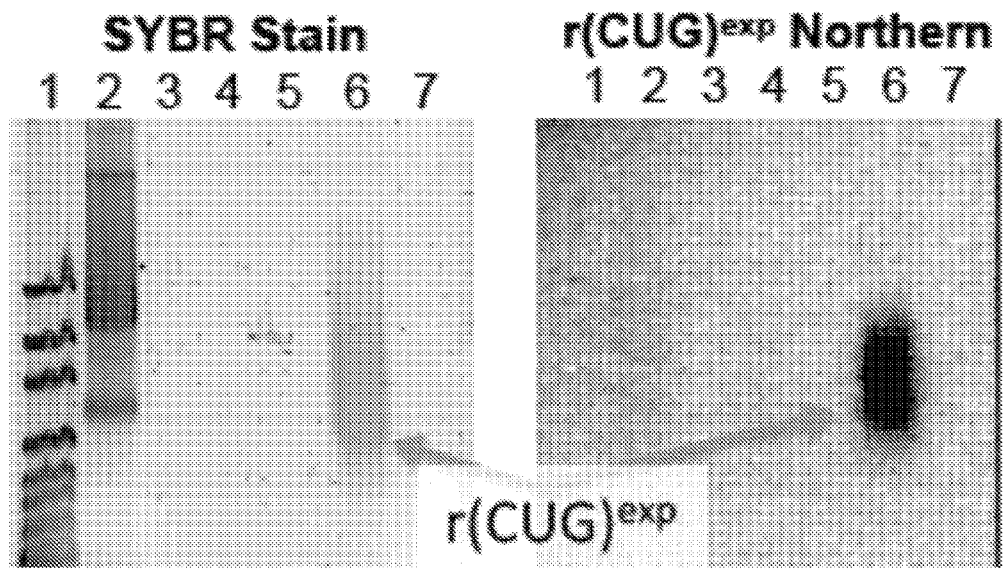

The cellular targets of the optimal r(CUG)$^{exp}$-targeting compound were identified using a modified version of a pull down experiment (FIG. 6). Briefly, a biotinylated 2H-K4NMe derivative (2H-K4NMe-Biotin) was synthesized and anchored onto streptavidin resin to afford an affinity purification matrix. Total RNA was extracted from a DM1 cellular model and incubated with the affinity matrix. After extensive washing, northern blotting revealed that r(CUG)$^{exp}$ is highly enriched in the eluted RNA bound by 2H-K4NMe-Biotin (FIG. 6). Interestingly, r(CUG)$^{exp}$ was not pulled down by streptavidin beads that display an oligonucleotide complementary to r(CUG)$^{exp}$, 5'-biotin-d(CAG)$_{12}$. This is likely due to the highly structured nature of the r(CUG)$^{exp}$ target.[8, 25, 27, 60-67] Since oligonucleotides recognize sequence, formation of a duplex between r(CUG)$^{exp}$ and a complementary oligonucleotide can only occur after the intramolecular structure is unfolded, a significant barrier for complex formation. Small molecules that recognize structure would not have this barrier for binding to highly structured RNA targets.

2H-K4NMe Improves Splicing Defects in a Mouse Model of DM1.

Figure 7A:
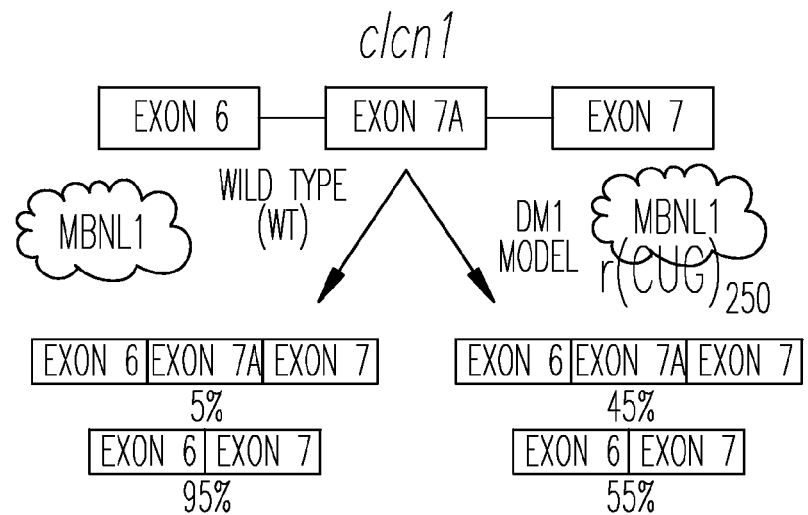
FIG. 7. 2H-K4NMe improves DM1-associated alternative pre-mRNA splicing defects in a DM1 mouse model. The DM1 mouse model expresses the human skeletal actin (HSA) transgene containing 250 CTG repeats (HSA$^{LR}$; where LR indicates long repeats). Wild type (WT) refers to FVB mice. (A) Top, schematic of Clcn1 alternative splicing in WT and DM1 mice. Bottom, analysis of Clcn1 alternative splicing by RT-PCR when mice are treated for each day for 7 days with 100 mg/kg of 2H-K4NMe. (B) Top, schematic of Serca1 (Atp2a1) alternative splicing in WT and DM1 mice. Bottom, analysis of Serca1 alternative splicing by RT-PCR when mice are treated with 100 mg/kg/d of 2H-K4NMe "**" indicates p<0.01 as determined by a two-tailed Student t-test.
Figure 7A:
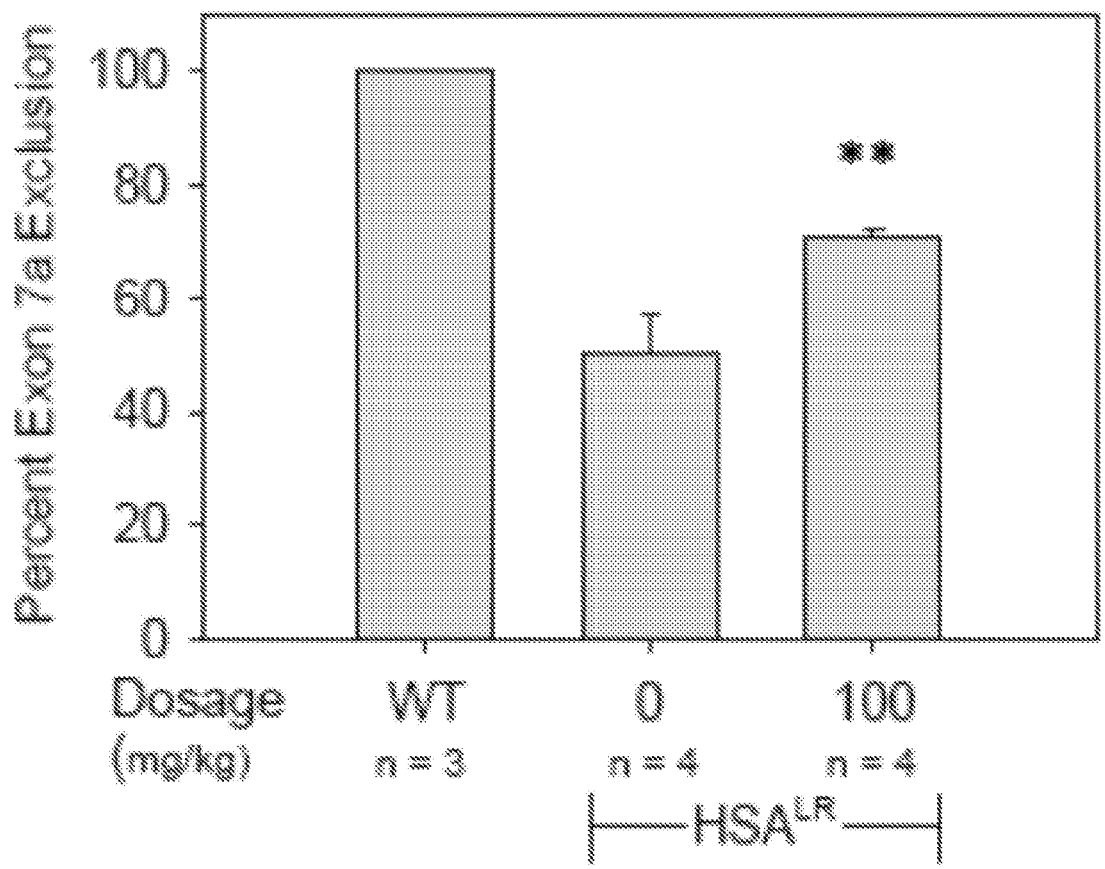
Figure 7B:
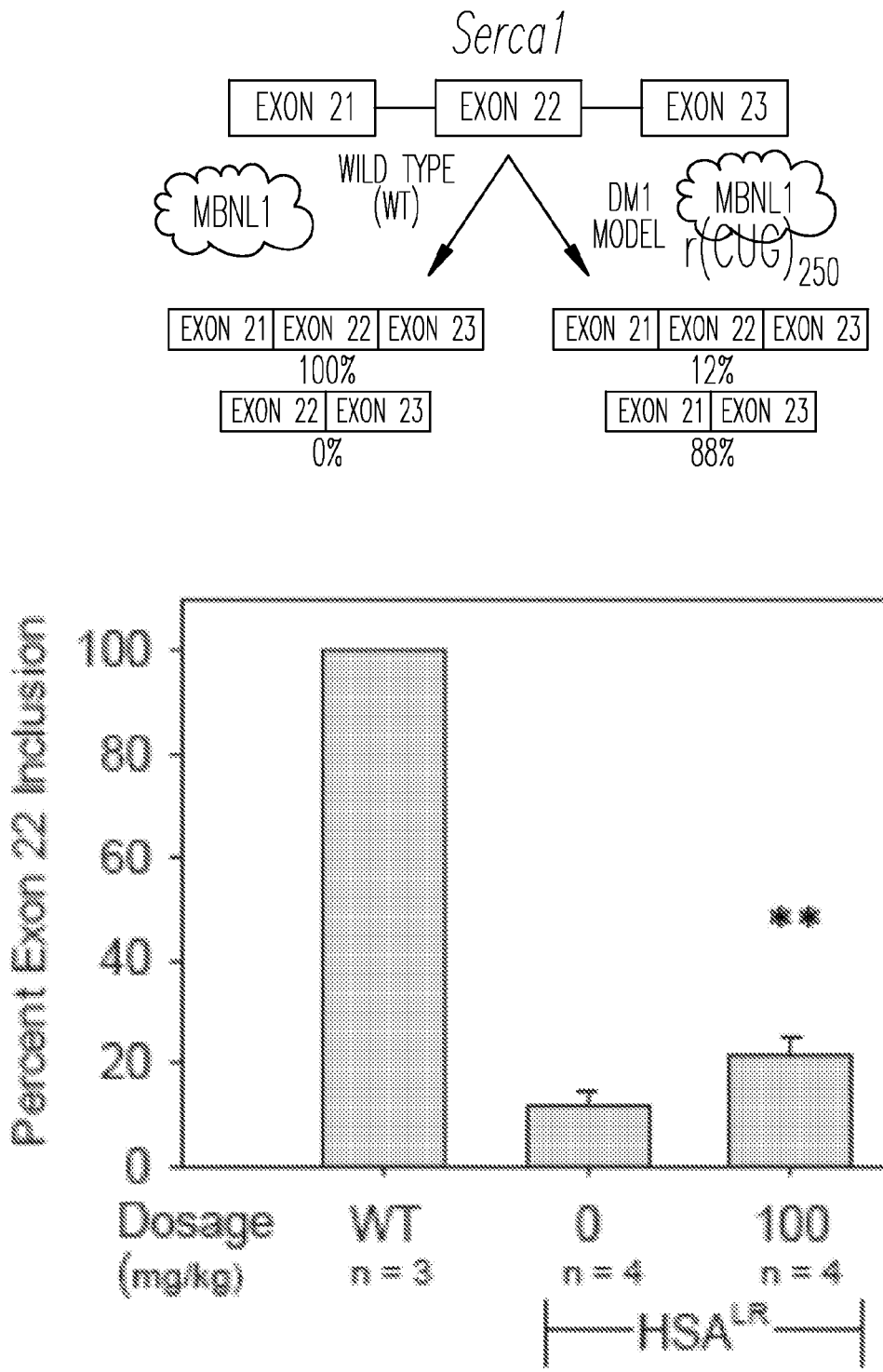
Figure 8:
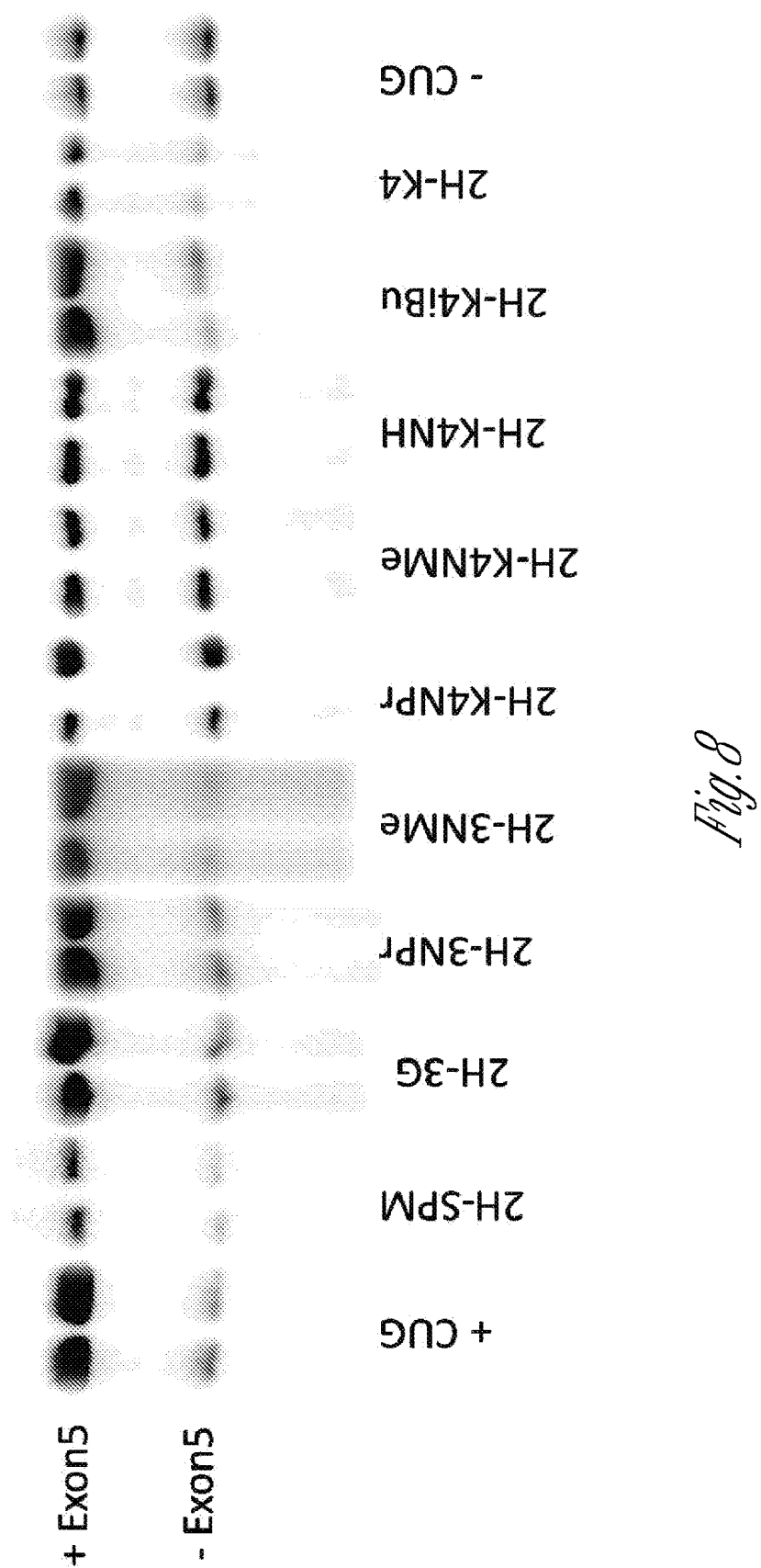
FIG. 8. Representative gel autoradiogram that shows the effect of modularly assembled small molecules on splicing defects in a cell culture model of DM1. HeLa cells were co-transfected with a mini-gene that encodes 960 interrupted CTG repeats and a cTNT alternative splicing mini-gene.[4]
Figure 11:
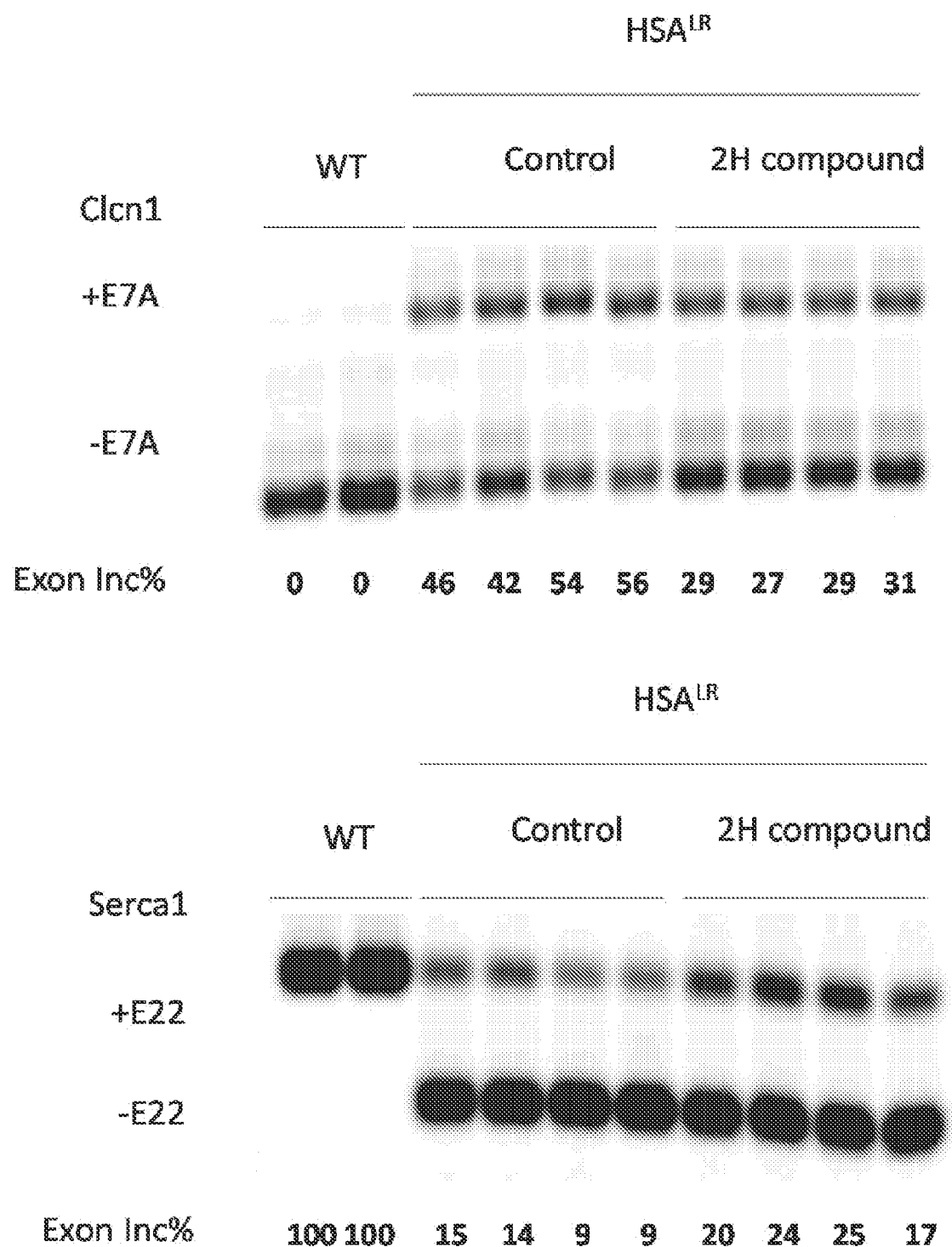
FIG. 11. Representative gel autoradiogram that shows the effect of 2H-K4NMe on splicing defects in a mouse model of DM1. Top: Results of Clcn1 analysis, Bottom: Results of Serca1 analysis.
Figure 12:
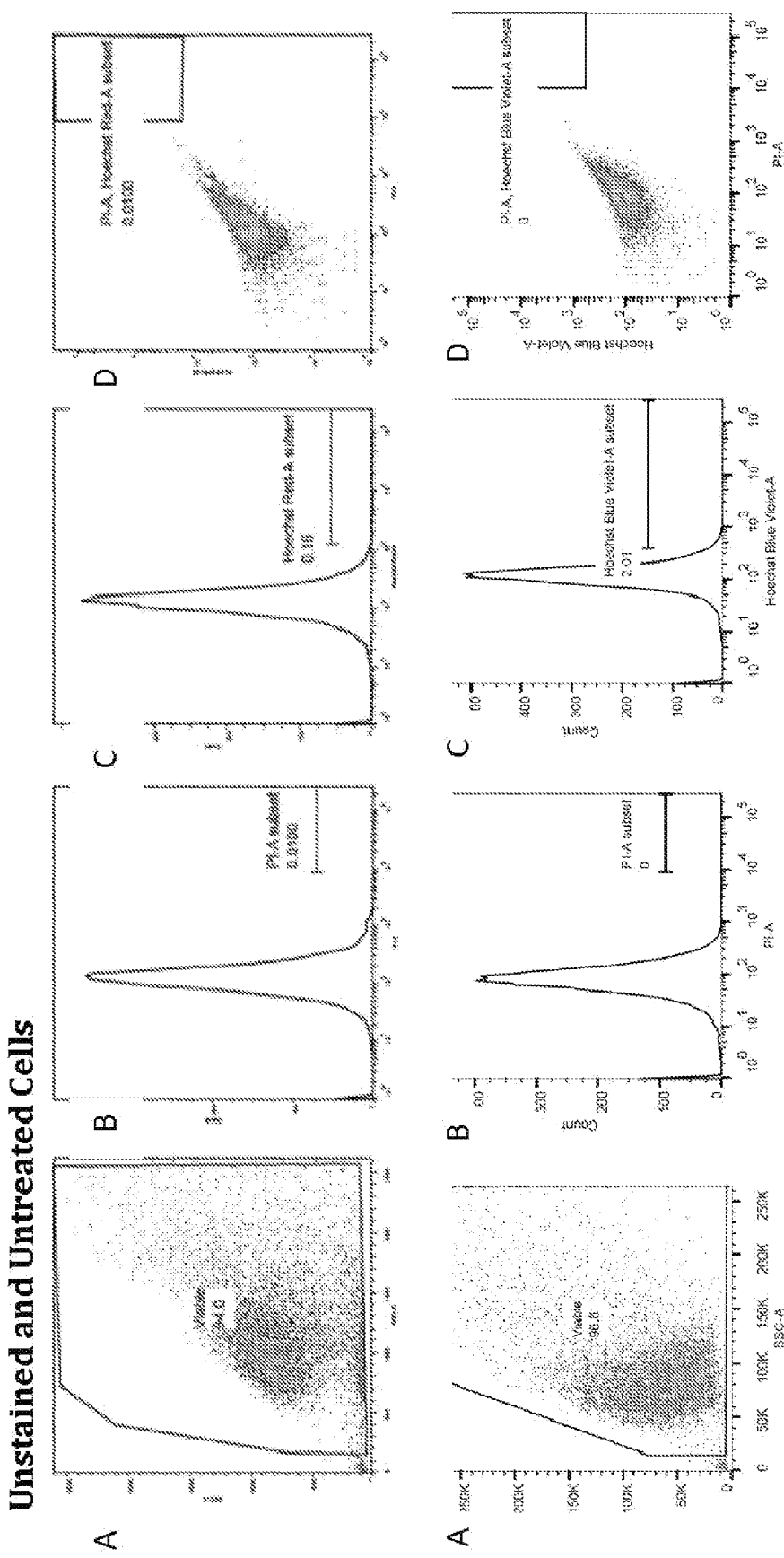
FIGS. 12-13 show the plots used to determine populations of (A) viable cells, (B) propidium iodide stained cells, (C) cells with Hoechst fluorescence, and (D) cells with Hoechst fluorescence and propidium iodide staining compound identities and controls as noted. First set (A)-(D) for each Figure relates to the Hoechst Red-A subset, and the second set (A)-(D) for each Figure relates to the Hoechst Blue Violet-A subset.
Figure 13:
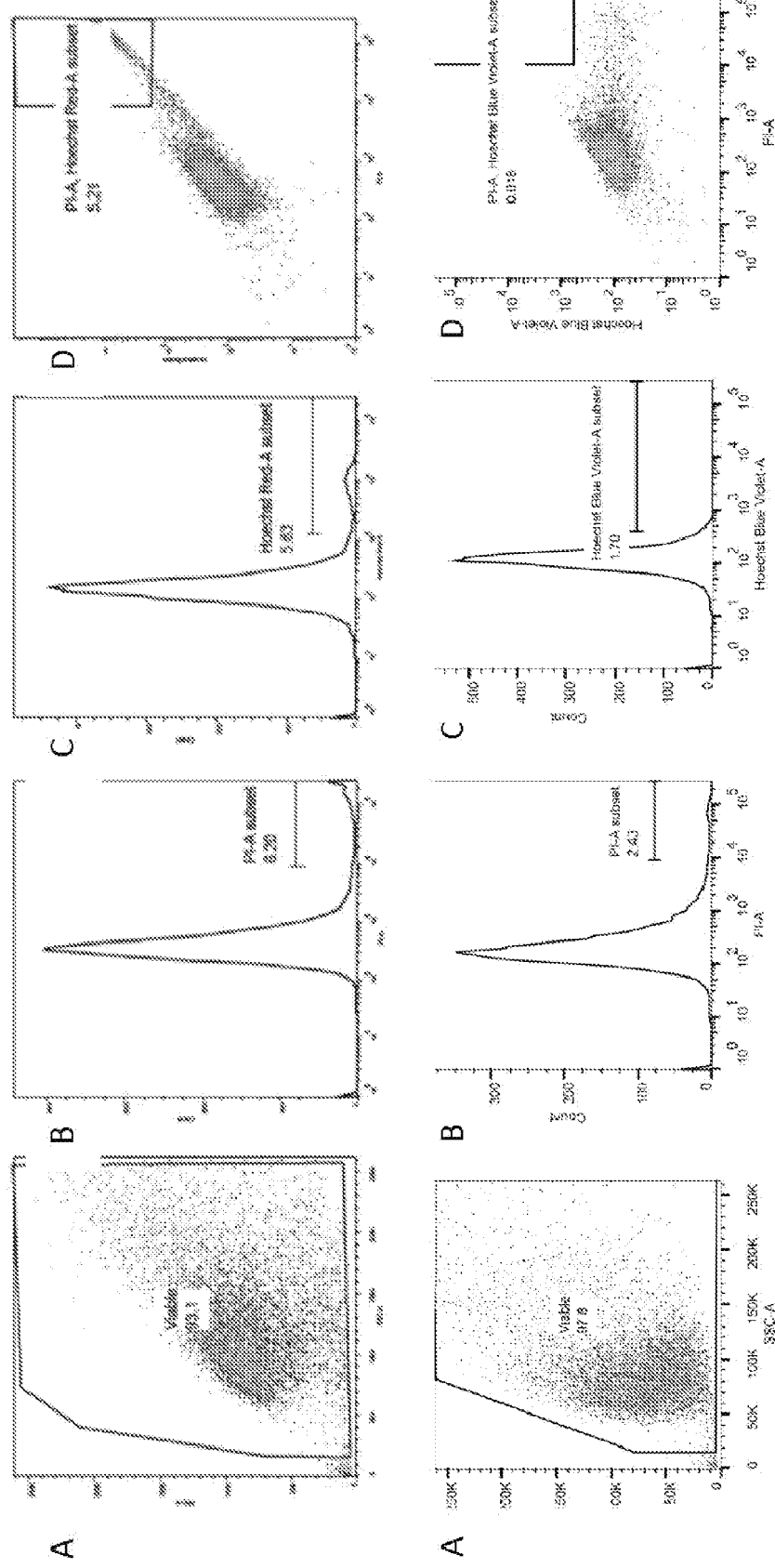
Figure 14:
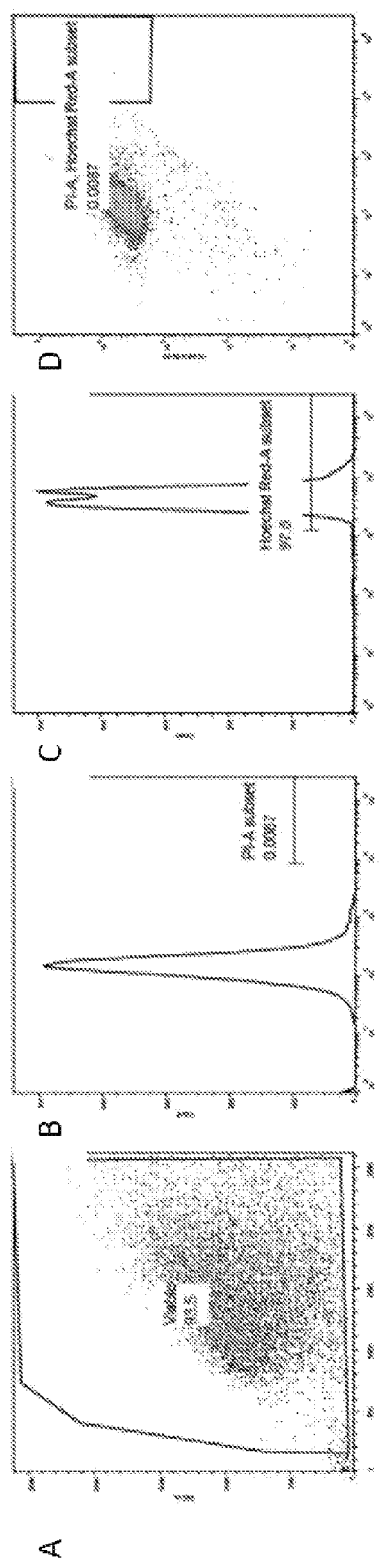
FIGS. 14-24 show the plots used to determine population of (A) viable cells, (B) propidium iodide stained cells, (C) cells with Hoechst fluorescence, and (D) cells with Hoechst fluorescence and propidium iodide staining, for Hoechst 33258 Controls cells, and the stated compounds 2H-4, 2H-SPM, 2H-3G, 2H-3NPr, 2H-3NMe, 2H-K4NPr, 2H-K4NMe, 2H-K4NH, 2H-K4NiBu, and 2H-K4, at 10 μM and 1 μM concentrations.
Figure 14:
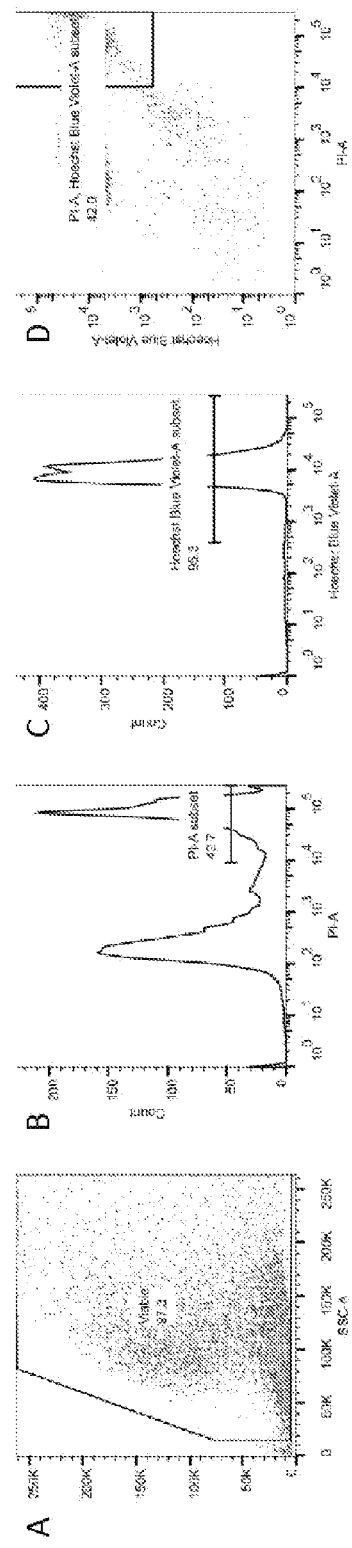
Figure 15:
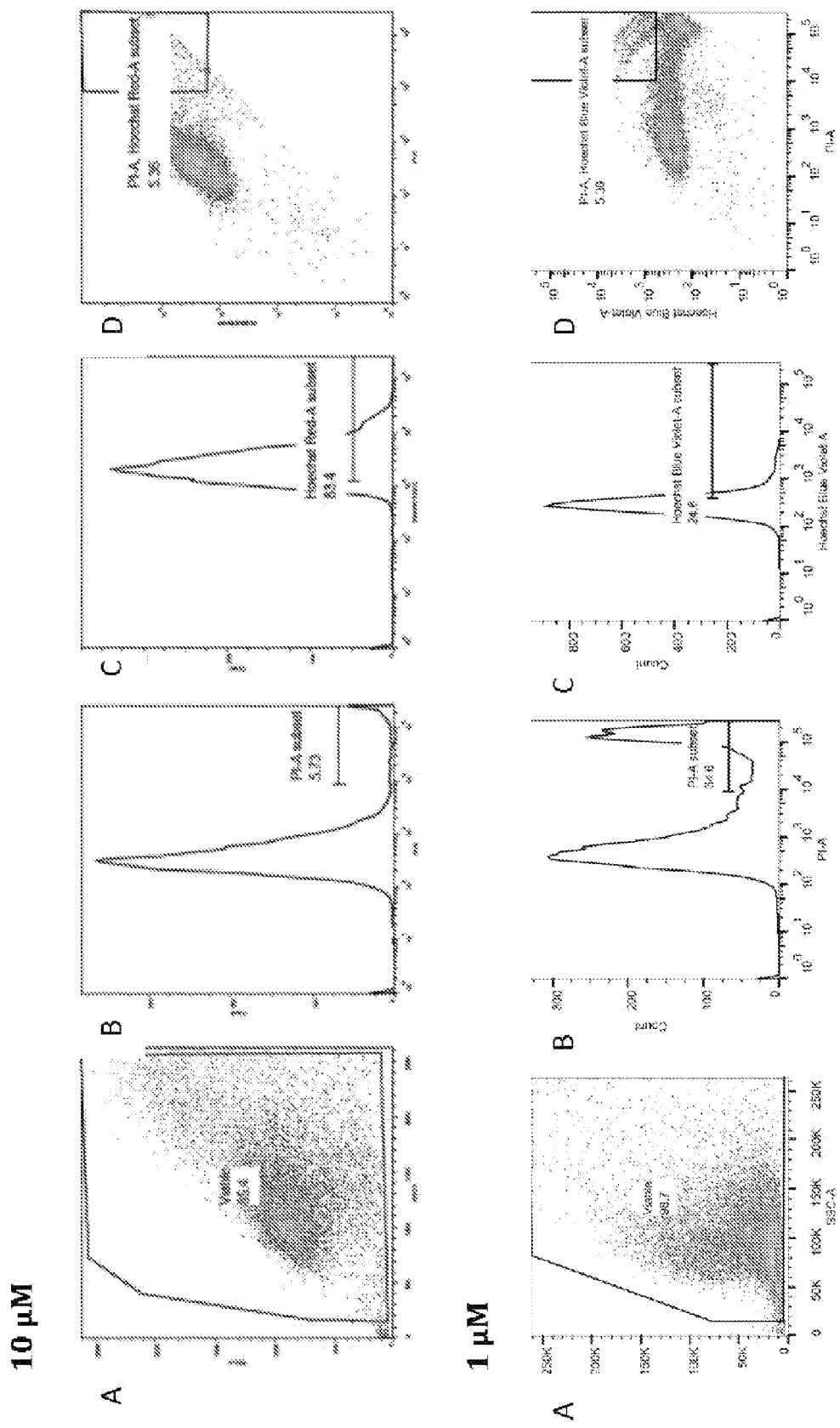
Figure 16:
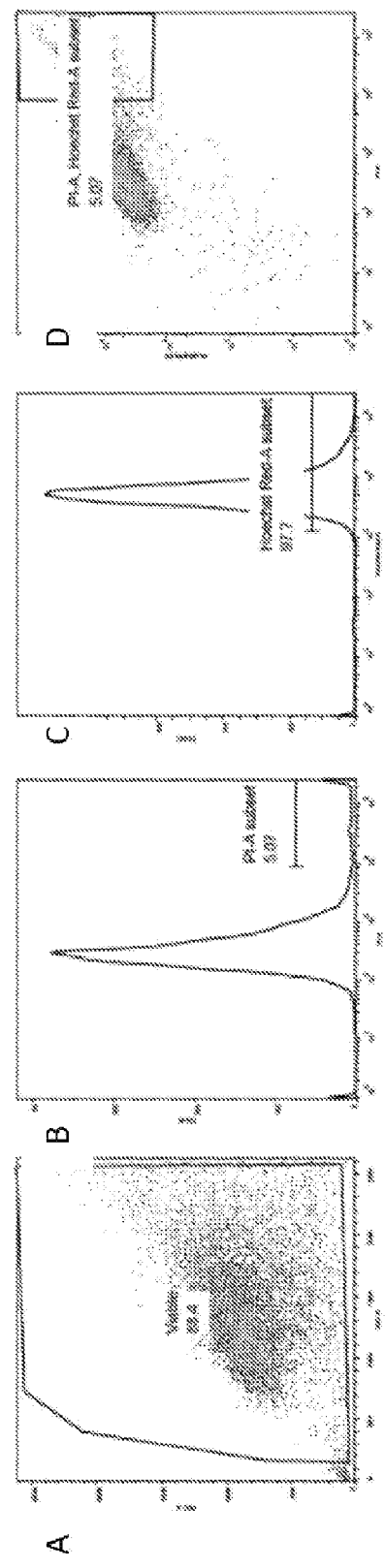
Figure 16:
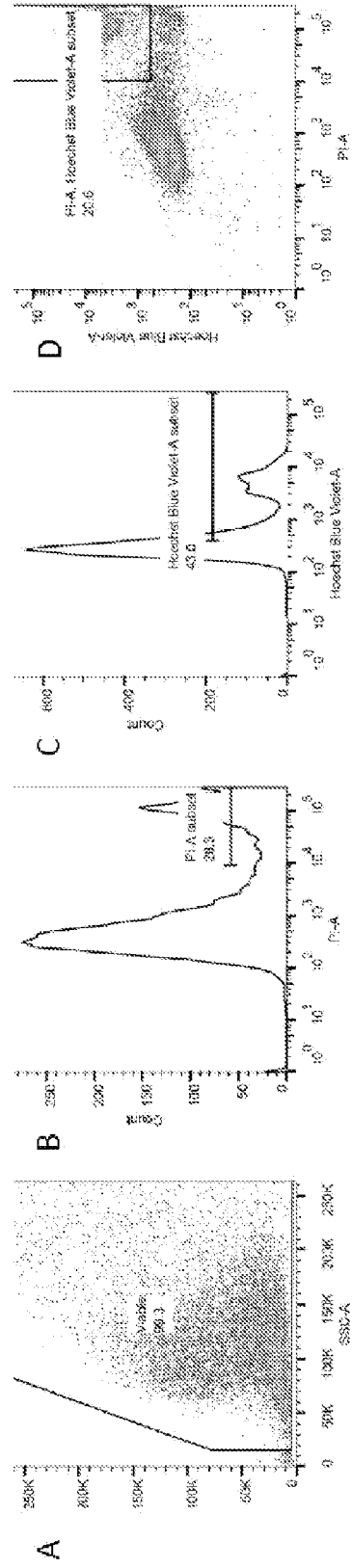
Figure 17:
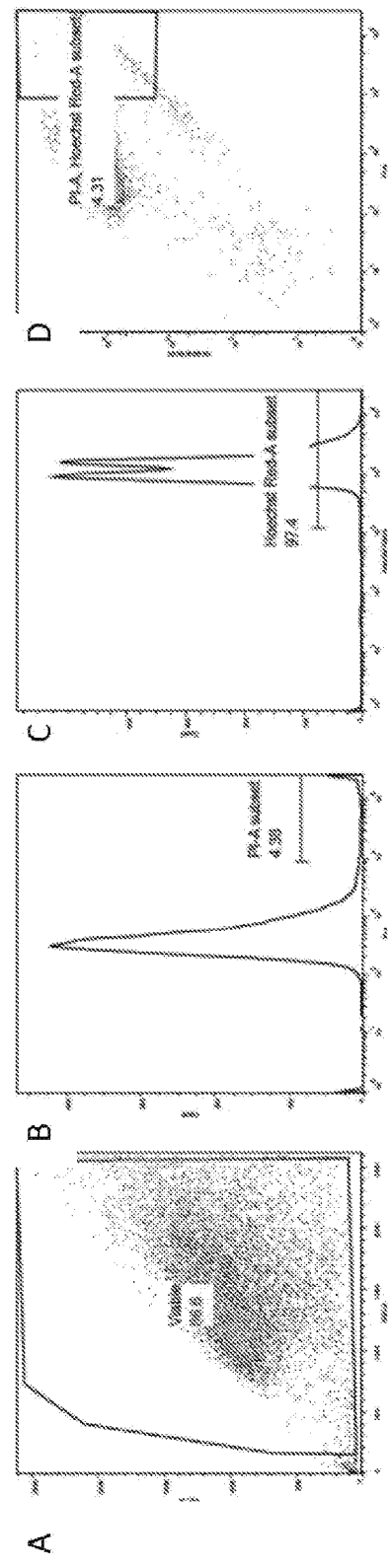
Figure 17:
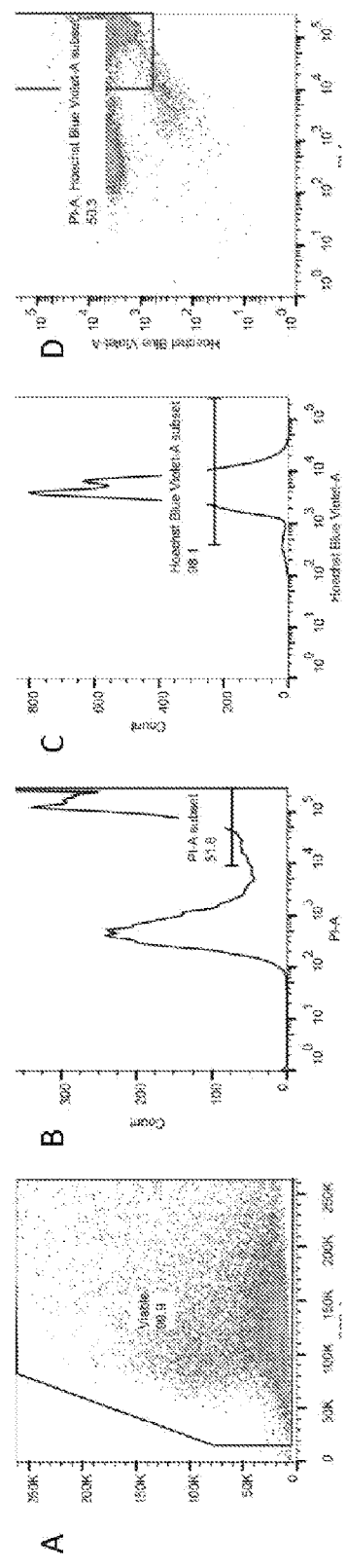
Figure 18:
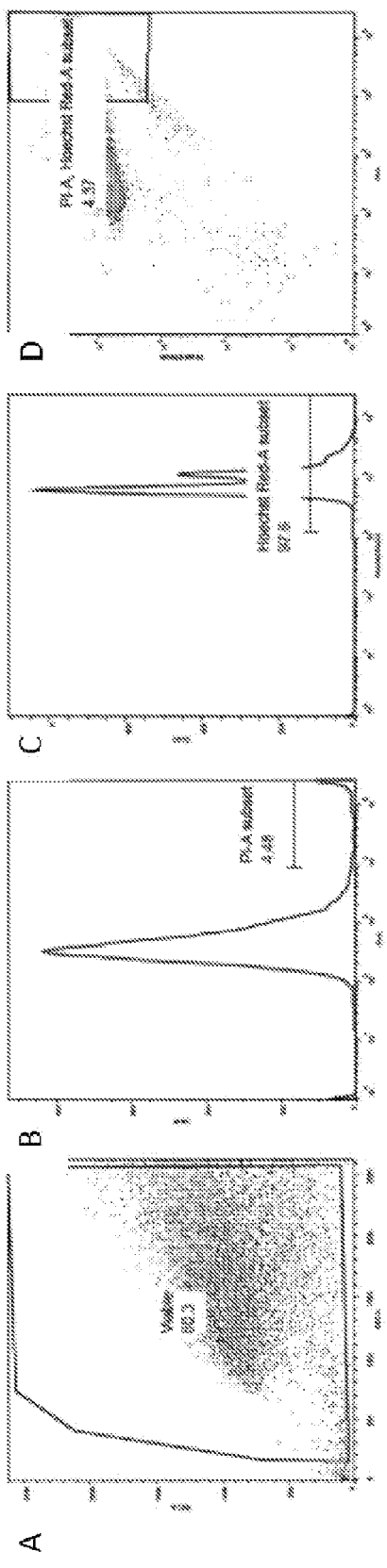
Figure 18:
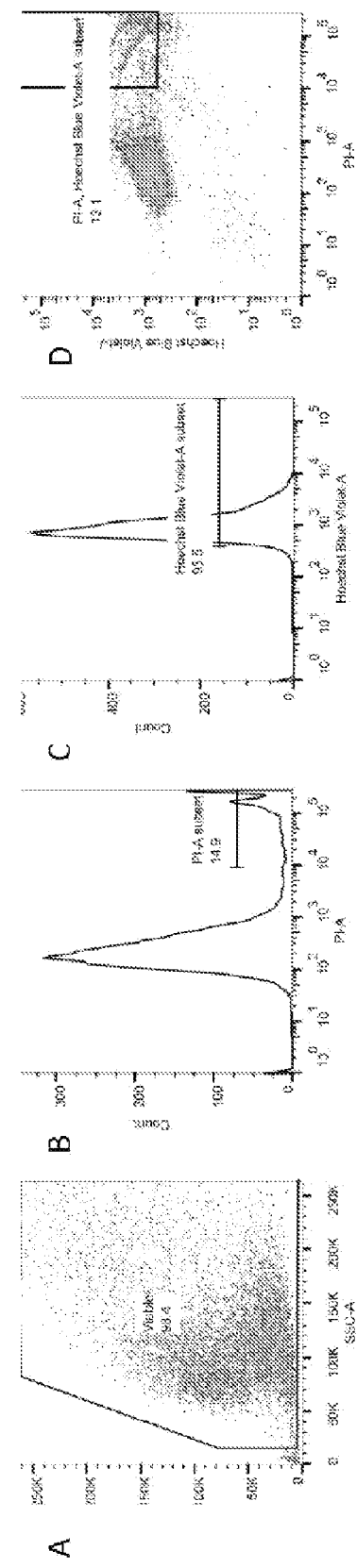
Figure 19:
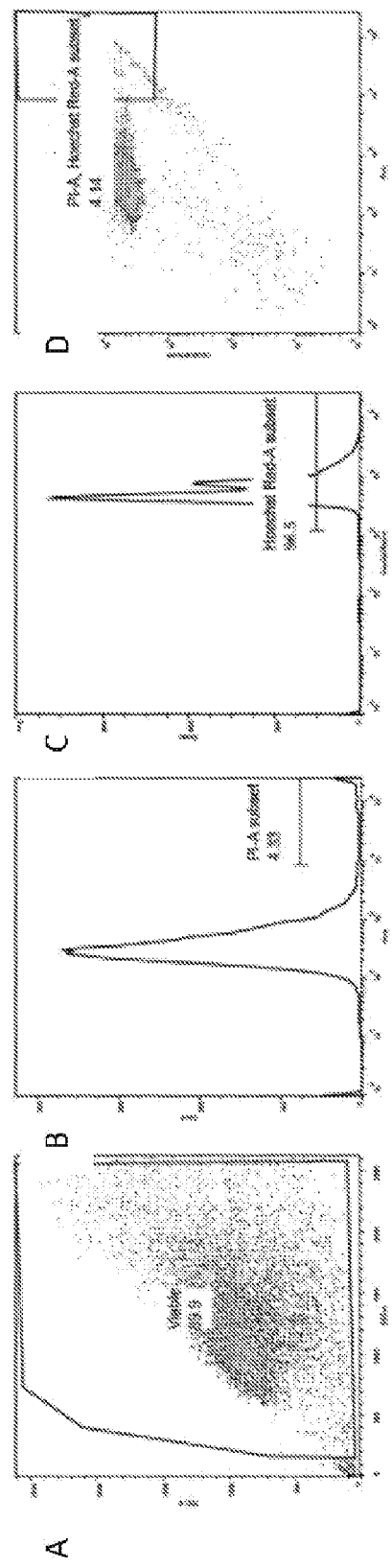
Figure 19:
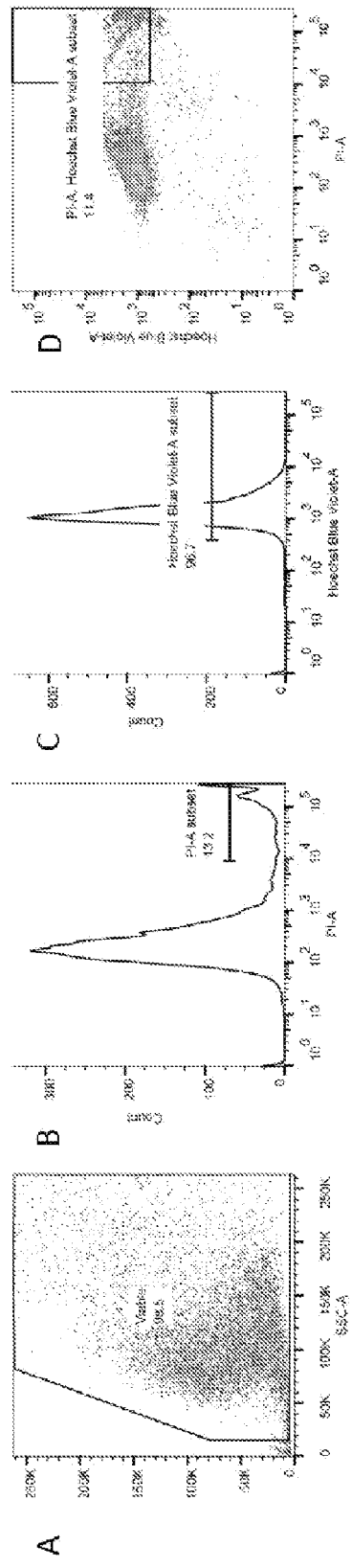
Figure 20:
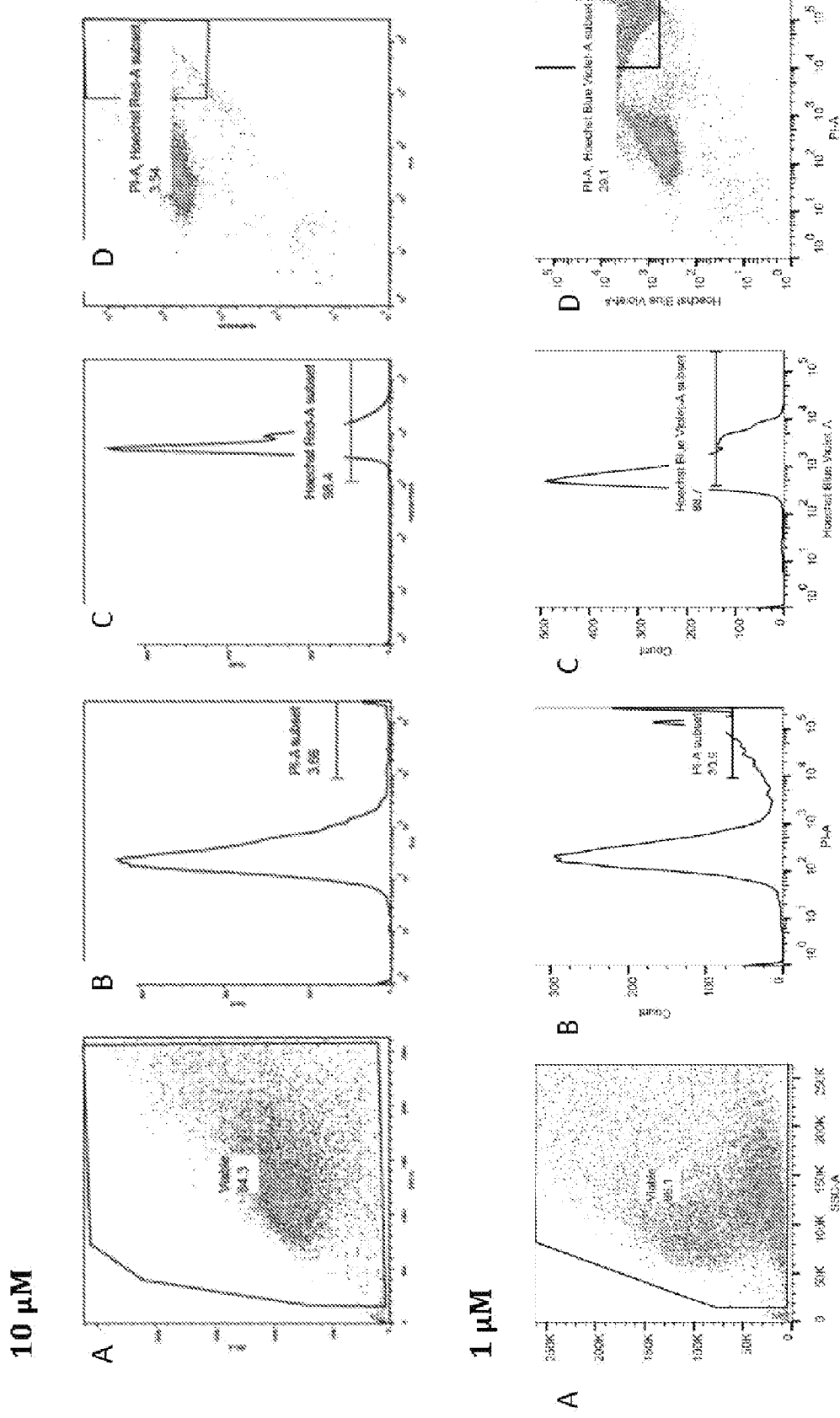
Figure 21:
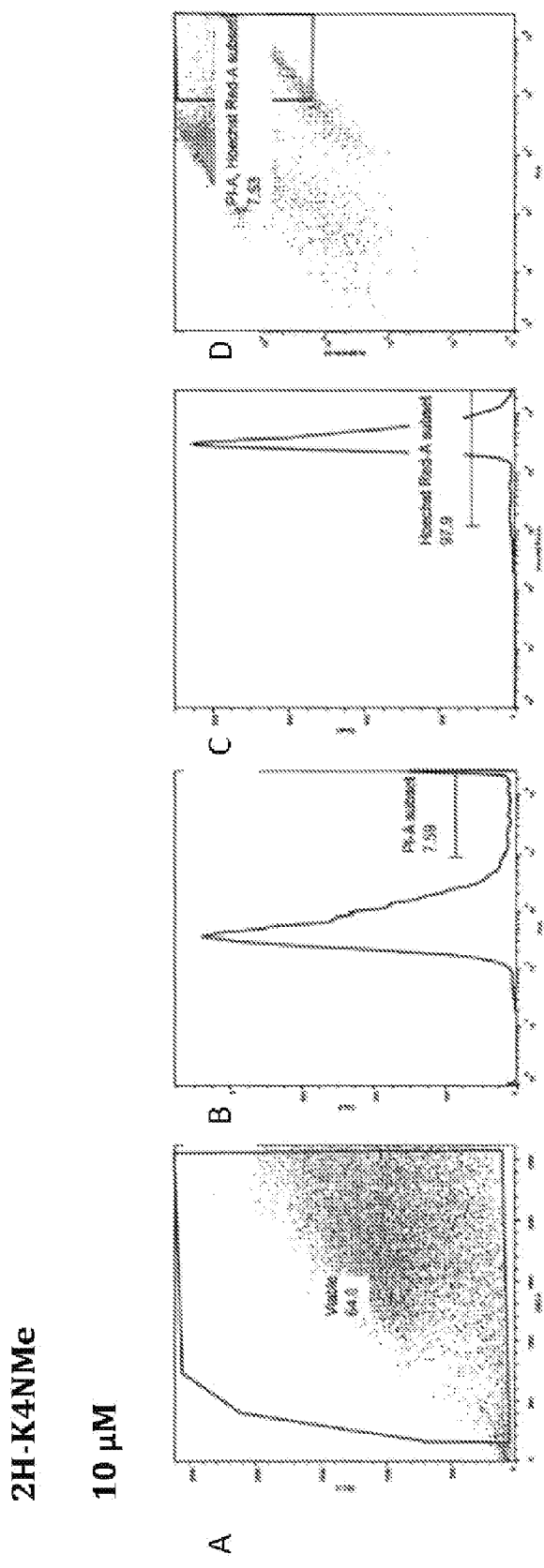
Figure 21:
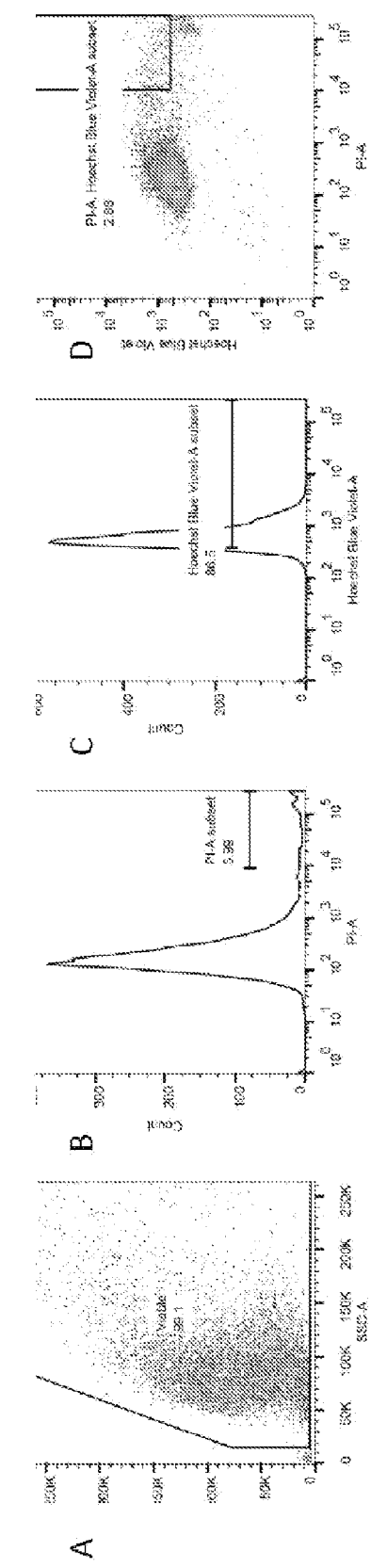
Figure 22:
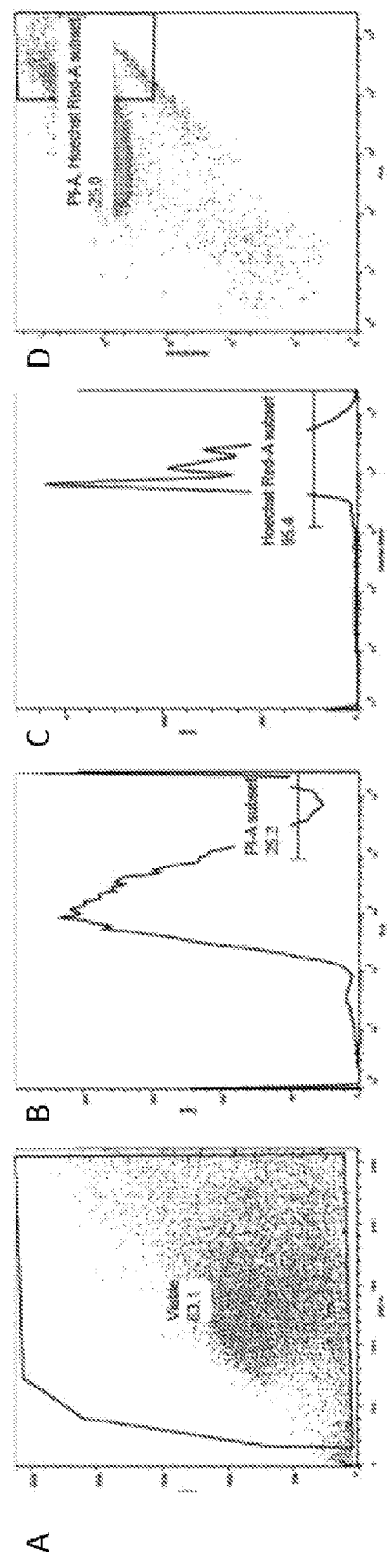
Figure 22:
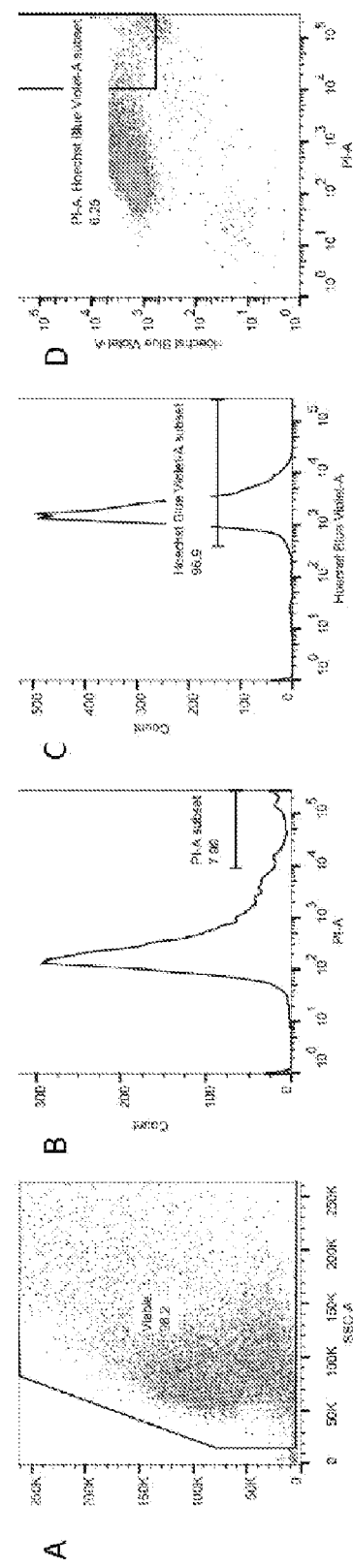
Figure 23:
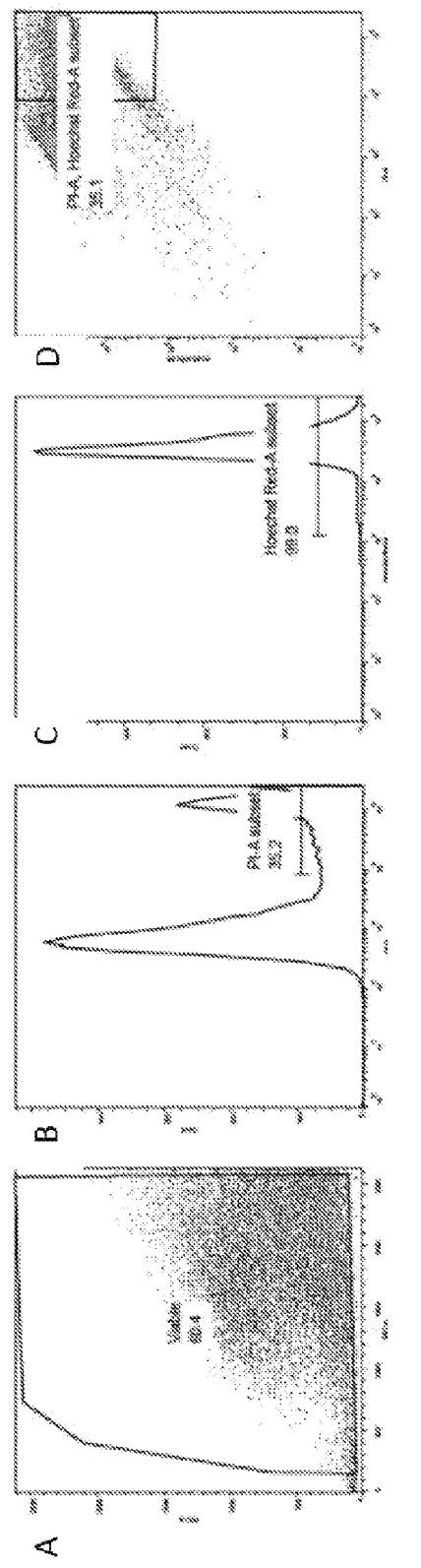
Figure 23:
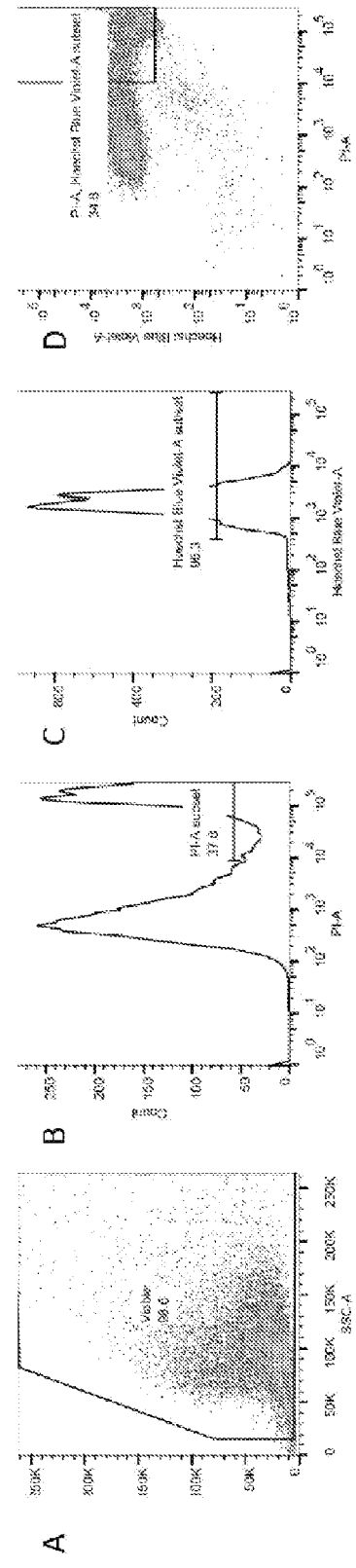
Figure 24:
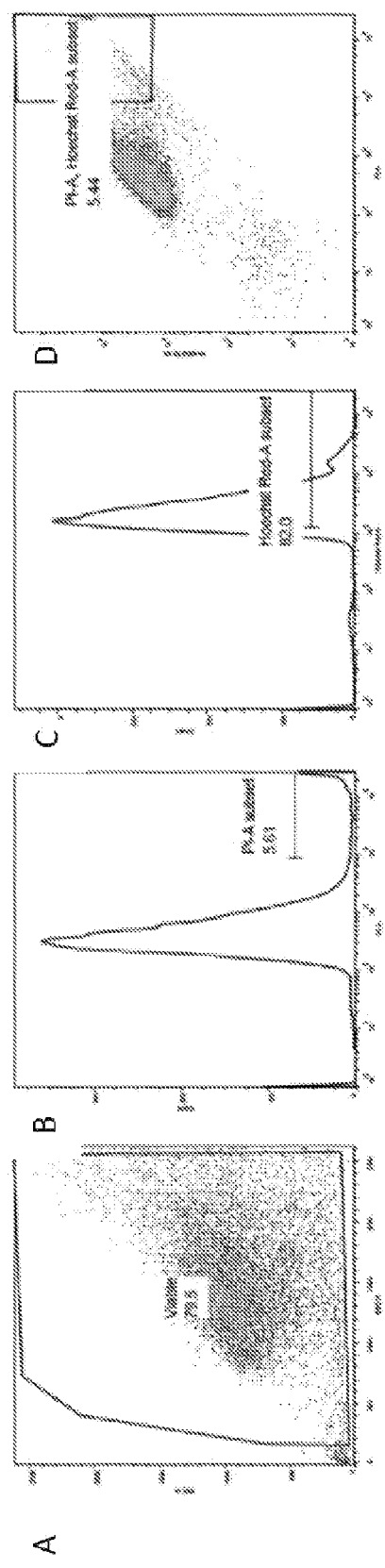
Figure 24:
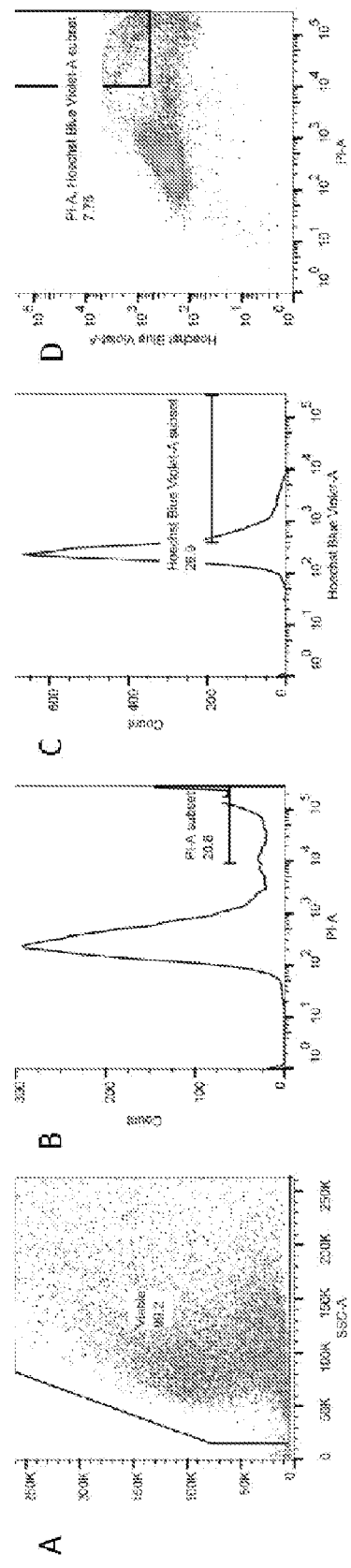

2H-K4NMe was selected for animal studies based on overall performance in cell-based assays, increased proteolytic stability as compared to 2H-KNH and decreased structural complexity compared to 2H-K4NPr. A mouse model of DM1 has been reported in which 250 rCUG repeats are expressed using an actin promoter (human skeletal actin long repeat, HSA$^{LR}$).[24] The presence of these repeats results in dysregulation of alternative splicing in the muscle-specific chloride ion channel (Clcn1) and the sarcoplasmic/endoplasmic reticulum calcium ATPase 1 (Serca1/Atp2$a$1) pre-mRNAs. Clcn1 exon 7$a$ is excluded ~100% in mRNA from normal adult mice; DM1 mice have an exclusion rate of ~50%. After DM1 mice were treated for 7 days with 100 mg/kg/d of 2H-K4NMe, the exclusion rate of exon 7A was restored to 71% (p-value=0.007) (FIGS. 7 and 11). Missplicing of Serca1 exon 21 was also partially rescued. The exon 22 inclusion rate is ~100% in normal adult mice and ~11.8% in DM1 mice. After treatment with 2H-K4NMe, the inclusion rate increases to 21.5% (p-value=0.008). Importantly, 2H-K4NMe did not affect the alternative splicing of Itgb1 and CapZB mRNAs, which are not regulated by MBNL1.

Summary and Outlook.

In this study we investigated the role of the modularly assembly scaffold on in vitro and in vivo activities of compounds designed to target the RNA that causes myotonic dystrophy type 1. Based on a variety of criteria, including in vitro and in vivo potency, proteolytic stability, cellular permeability, and toxicity, the optimal scaffold is a PTA. Importantly, a kinetics investigation showed that modularly assembled small molecules have faster on rates and slower off rates than monomeric small molecules or MBNL1 protein, perhaps owing to a hinge effect to difference in the nature of the binding of small molecule and protein to r(CUG)$^{exp}$. These kinetic advantages likely explain the potent biological effects of our divalent compounds, as the RNA-binding modules from which they are composed of by themselves are inactive. Such effects can be programmed into designer small molecules targeting other cellular RNAs.

In addition, we leveraged the chemistry allowed by a modular assembly approach to incorporate a biotin tag. This modification allowed the pull down of cellular targets of a small molecule using streptavidin beads and demonstrated that r(CUG)$^{exp}$ is indeed a target of our designed compounds. This is the first study that identified r(CUG)$^{exp}$ as a cellular target of small molecules that improve DM1-associated defects and further supports our design strategy. Other tags can be incorporated into modularly assembled compounds including warheads for targeted cleavage or covalent cross-linking.[63, 64] Importantly, our optimal compound improves DM1-associated alternative splicing defects in a mouse model and thus has therapeutic potential.

Documents Cited:

1. Poehlsgaard, J., and Douthwaite, S. (2005) The bacterial ribosome as a target for antibiotics. *Nat. Rev. Microbiol.* 3, 870-881.

2. Projan, S. J. (2002) New (and not so new) antibacterial targets—from where and when will the novel drugs come? *Curr. Opin. Pharmacol.* 2, 513-522.

3. Berg, J. M., Tymoczko, J. L., and Sttyer, L. (2007) *Biochemistry, Sixth Edition.* W. H. Freeman and Company, New York.

4. Johnson, L. F., Abelson, H. T., Penman, S., and Green, H. (1977) The relative amounts of the cytoplasmic RNA species in normal, transformed and senescent cultured cell lines. *J. Cell. Physiol.* 90, 465-470.

5. Johnson, L. F., Williams, J. G., Abelson, H. T., Green, H., and Penman, S. (1975) Changes in RNA in relation to growth of the fibroblast. III. Posttranscriptional regulation of mRNA formation in resting and growing cells. *Cell* 4, 69-75.

6. Blount, K. F., and Breaker, R. R. (2006) Riboswitches as antibacterial drug targets. *Nat. Biotechnol.* 24, 1558-1564.

7. Blount, K. F., Wang, J. X., Lim, J., Sudarsan, N., and Breaker, R. R. (2007) Antibacterial lysine analogs that target lysine riboswitches. *Nat. Chem. Biol.* 3, 44-49.

8. Kumar, A., Park, H., Fang, P., Parkesh, R., Guo, M., Nettles, K. W., and Disney, M. D. (2011) Myotonic dystrophy type 1 RNA crystal structures reveal heterogeneous 1×1 nucleotide UU internal loop conformations. Biochemistry 50, 9928-9935.

9. Guan, L., and Disney, M. D. (2012) Recent advances in developing small molecules targeting RNA. *ACS Chem. Biol.* 7, 73-86.

10. Childs-Disney, J. L., Wu, M., Pushechnikov, A., Aminova, O., and Disney, M. D. (2007) A small molecule microarray platform to select RNA internal loop-ligand interactions. *ACS Chem. Biol.* 2, 745-754.

11. Velagapudi, S. P., Seedhouse, S. J., and Disney, M. D. (2010) Structure-activity relationships through sequencing (StARTS) defines optimal and suboptimal RNA motif targets for small molecules. *Angew. Chem. int. Ed. Engl.* 49, 3816-3818.

12. Disney, M. D., Labuda, L. P., Paul, D. J., Poplawski, S. G., Pushechnikov, A., Tran, T., Velagapudi, S. P., Wu, M., and Childs-Disney, J. L. (2008) Two-dimensional combinatorial screening identifies specific aminoglycoside-RNA internal loop partners. *J. Am. Chem. Soc.* 130, 11185-11194.

13. Pushechnikov, A., Lee, M. M., Childs-Disney, J. L., Sobczak, K., French, J. M., Thornton, C. A., and Disney, M. D. (2009) Rational design of ligands targeting triplet repeating transcripts that cause RNA dominant-disease: application to myotonic muscular dystrophy type 1 and spinocerebellar ataxia type 3. *J. Am. Chem. Soc.* 131, 9767-9779.

14. Velagapudi, S. P., Seedhouse, S. J., French, J., and Disney, M. D. (2011) Defining the RNA internal loops preferred by benzimidazole derivatives via 2D combinatorial screening and computational analysis. *J. Am. Chem. Soc.* 133, 10111-10118.

15. Parkesh, R., Childs-Disney, J. L., Nakamori, M., Kumar, A., Wang, E., Wang, T., Hoskins, J., Tran, T., Housman, D. E., Thornton, C. A., and Disney, M. D. (2012) Design of a bioactive small molecule that targets the myotonic dystrophy type 1 RNA via an RNA motif-ligand database & chemical similarity searching. *J. Am. Chem. Soc.* 134, 4731-4742.

16. Kumar, A., Parkesh, R., Sznajder, L. J., Childs-Disney, J. L., Sobczak, K., and Disney, M. D. (2012) Chemical correction of pre-mRNA splicing defects associated with sequestration of muscleblind-like 1 protein by expanded r(CAG)-containing transcripts. *ACS Chem., Biol.* 7, 496-505.

17. Childs-Disney, J. L., Parkesh, R., Nakamori, M., Thornton, C. A., and Disney, M. D. (2012) Rational design of bioactive, modularly assembled aminoglycosides targeting the RNA that causes myotonic dystrophy type 1. *ACS Chem. Biol.* 7, 1984-1993.

18. Childs-Disney, J. L., Hoskins, J., Rzuczek, S. G., Thornton, C. A., and Disney, M. D. (2012) Rationally designed small molecules targeting the RNA that causes myotonic dystrophy type 1 are potently bioactive. *ACS Chem. Biol.* 7, 856-862.

19. Lee, M. M., Childs-Disney, J. L., Pushechnikov, A., French, J. M., Sobczak, K., Thornton, C. A., and Disney, M. D. (2009) Controlling the specificity of modularly assembled small molecules for RNA via ligand module spacing: targeting the RNAs that cause myotonic muscular dystrophy. *J. Am. Chem. Soc.* 131 17464-17472.

20. Lee, M. M., French, J. M., and Disney, M. D. (2011) Influencing uptake and localization of aminoglycoside-functionalized peptides. *Mol. Biosyst.* 7, 2441-2451.

21. Lee, M. M., Pushechnikov, A., and Disney, M. D. (2009) Rational and modular design of potent ligands targeting the RNA that causes myotonic dystrophy 2. *ACS Chem. Biol.* 4, 345-355.

22. Disney, M. D., Lee, M. M., Pushechnikov, A., and Childs-Disney, J. L. (2010) The role of flexibility in the rational design of modularly assembled ligands targeting the RNAs that cause the myotonic dystrophies. *Chembiochem* 11, 375-382.

23. Brook, J. D., McCurrach, M. E., Harley, H. G., Buckler, A. J.,-Church, D., Aburatani, H., Hunter, K., Stanton, V. P., Thirion, J. P., Hudson, T., Sohn, R., Zemelman, B., Snell, R. G., Rundle, S. A., Crow, S., Davies, J., Shelbourne, P., Buxton, J., Jones, C., Juvonen, V., Johnson, K., Harper, P. S., Shaw, D. J., and Housman, D. E. (1992) Molecular basis of myotonic dystrophy: expansion of a trinucleotide (CTG) repeat at the 3' end of a transcript encoding a protein kinase family member. *Cell* 68, 799-808.

24. Mankodi, A., Logigian, E., Callahan, L., McClain, C., White, R., Henderson, D., Krym, M., and Thornton, C. A. (2000) Myotonic dystrophy in transgenie mice expressing an expanded CUG repeat. *Science* 289, 1769-1773.

25. Tian, B., White, R. J., Xia, T., Welle, S., Turner, D. H., Mathews, M. B., and Thornton, C. A. (2000) Expanded CUG repeat RNAs form hairpins that activate the double-stranded RNA-dependent protein kinase PKR. *RNA* 6, 79-87.

26. Sobczak, K., Michiewski, G., de Mezer, M., Kierzek, E., Krol, J., Olejniczak, M., Kierzek, R., and Krzyzosiak, W. J. (2010) Structural diversity of triplet repeat RNAs. *J. Biol. Chem.* 285, 12755-12764.

27. Parkesh, R., Fountain, M., and Disney, M. D. (2011) NMR spectroscopy and molecular dynamics simulation of r(CCGCUGCGG)$_2$ reveal a dynamic UU internal loop found in myotonic dystrophy type 1. Biochemistry 50, 599-601.

28. Miller, J. W., Urbinati, C. R., Teng-Umnuay, P., Stenberg, M. G., Byrne, B. J., Thornton, C. A., and Swanson, M. S. (2000) Recruitment of human muscleblind proteins to (CUG)$_n$ expansions associated with myotonic dystrophy, *EMBO J.* 19, 4439-4448.

29. Paul, S., Dansithong, W., Kim, D., Rossi, J., Webster, N. J., Comai, L., and Reddy, S. (2006) Interaction of muscleblind, CUG-BP1 and hnRNP H proteins in DM1-associated aberrant IR splicing. *EMB0 J.* 25, 4271-4283.

30. Cardani, R., Mancinelli, E., Rotondo, G., Sansone, V., and Meola, G. (2006) Muscleblind-like protein 1 nuclear sequestration is a molecular pathology marker of DM1 and DM2. *Eur. J. Histochem.* 50, 177-182.

31. Jiang, H., Mankodi, A., Swanson, M. S., Moxley, R. T., and Thornton, C. A. (2004) Myotonic dystrophy type 1 is associated with nuclear foci of mutant RNA, sequestration of muscleblind proteins and deregulated alternative splicing in neurons. *Hum. Mol. Genet.* 13, 3079-3088.

32. Kanadia, R. N., Johnstone, K. A., Mankodi, A., Lungu, C., Thornton, C. A., Esson, D., Timmers, A. M., Hauswirth, W. W., and Swanson, M. S. (2003) A muscleblind knockout model for myotonic dystrophy. *Science* 302, 1978-1980.

33. Wheeler, T. M., Sobezak, K., Lueck, J. D., Osborne, R. J., Lin, X., Dirksen, R. T., and Thornton, C. A. (2009) Reversal of RNA dominance by displacement of protein sequestered on triplet repeat RNA. *Science* 325, 336-339.

34. Orengo, J. P., Ward, A. J., and Cooper, T. A. (2011) Alternative splicing dysregulation secondary to skeletal muscle regeneration. *Ann. Neurol.* 69, 681-690.

35. Taneja, K. L., McCurrach, M., Schalling, M., Housman, D., and Singer, R. H. (1995) Foci of trinucleotide repeat transcripts in nuclei of myotonic dystrophy cells and tissues. *J. Cell. Biol.* 128, 995-1002.

36. Mankodi, A., Urbinati, C. R., Yuan, Q. P., Moxley, R. T., Sansone, V., Krym, M., Henderson, D., Schalling, M., Swanson, M. S., and Thornton, C. A. (2001) Muscleblind localizes to nuclear foci of aberrant RNA in myotonic dystrophy types 1 and 2. *Hum. Mol. Genet.* 10, 2165-2170.

37. Wojciechowska, M., and Krzyzosiak, W. J. (2011) Cellular toxicity of expanded RNA repeats: focus on RNA foci. *Hum. Mol. Genet.* 39, 8938-8951.

38. Mastroyiannopoulos, N. P., Feldman, M. L., Utley, J. B., Mahadevan, M. S., and Phylactou, L. A. (2005) Wood- 38. chuck post-transcriptional element induces nuclear export of myotonic dystrophy 3' untranslated region transcripts. *EMBO Rep.* 6, 458-463.

39. Amack, J. D., and Mahadevan, M. S. (2001) The myotonic dystrophy expanded CUG repeat tract is necessary but not sufficient to disrupt C2C12 myoblast differentiation. *Hum. Mol. Genet.* 10, 1879-1887.

40. Amack, J. D., Paguio, A. P., and Mahadevan, M. S. (1999) Cis and trans effects of the myotonic dystrophy (DM) mutation in a cell culture model. *Hum. Mol. Genet.* 8, 1975-1984.

41. Lee, J. E., Bennett, C. F., and Cooper, T. A. (2012) RNase H-mediated degradation of toxic RNA in myotonic dystrophy type 1. *Proc. Natl. Acad. Sci. U.S.A.* 109, 4221-4226.

42. Kanadia, R. N., Shin, J., Yuan, Y., Beattie, S. G., Wheeler, T. M., Thornton, C. A., and Swanson, M. S. (2006) Reversal of RNA missplicing and myotonia after muscleblind overexpression in a mouse poly (CUG) model for myotonic dystrophy. *Proc. Natl. Acad. Sci. U.S.A* 103, 11748-11753.

43. Gareiss, P. C., Sobezak, K., McNaughton, B. R., Palde, P. B., Thornton, C. A., and Miller, B. L. (2008) Dynamic combinatorial selection of molecules capable of inhibiting the (CUG) repeat RNA-MBNL1 interaction in vitro: Discovery of lead compounds targeting myotonic dystrophy (DM1). *J. Am. Chem. Soc.* 130, 16254-16261.

44. Arambula, J. F., Ramisetty, S. R., Baranger, A. M., and Zimmerman, S. C. (2009) A simple ligand that selectively targets CUG trinucleotide repeats and inhibits MBNL protein binding. *Proc. Natl. Acad. Sci. U.S.A.* 106, 16068-16073.

45. Warf, M. B., Nakamori, M., Matthys, C. M., Thornton, C. A., and Berglund, J. A. (2009) Pentamidine reverses the splicing defects associated with myotonic dystrophy. *Proc. Natl. Acad. Sci. U.S.A.* 106, 18551-18556.

46. Garcia-Lopez, A., Llamusi, B., Orzaez, M., Perez-Paya, E., and Artero, R. D. (2011) In vivo discovery of a peptide that prevents CUG-RNA hairpin formation and reverses RNA toxicity in myotonic dystrophy models. *Proc. Natl. Acad. Sci. U.S.A.* 108, 11866-11871.

47. Chen, C. Z., Sobczak, K., Hoskins, J., Southall, N., Marugan, J. J., Zheng, W., Thornton, C. A., and Austin, C. P. (2012) Two high-throughput screening assays for aberrant RNA-protein interactions in myotonic dystrophy type 1. *Anal. Bioanal. Chem.* 402, 1889-1898.

48. Hook, D. F., Gessier, F., Noti, C., Kast, P., and Seebach, D. (2004) Probing the proteolytic stability of beta-peptides containing alpha-fluoro- and alpha-hydroxy-beta-amino acids. *Chembiochcm* 5, 691-706.

49. Orengo, J. P., Bundman, D., and Cooper, T. A. (2006) A bichromatic fluorescent reporter for cell-based screens of alternative splicing. *Nucleic Acids Res.* 34, e148.

50. Faustino, N. A., and Cooper, T. A. (2003) Pre-mRNA splicing and human disease. *Genes Dev.* 17, 419-437.

51. Philips, A. V., Timchenko, L. T., and Cooper, T. A. (1998) Disruption of splicing regulated by a CUG-binding protein in myotonic dystrophy. *Science* 280, 737-741.

52. Yu, P., Liu, B., and Kodadek, T. (2005) A high-throughput assay for assessing the cell permeability of combinatorial libraries. *Nat. Biotechnol.* 23, 746-751.

53. Kwon, Y. U., and Kodadek, T. (2007) Quantitative evaluation of the relative cell permeability of peptoids and peptides. *J. Am. Chem. Soc.* 129, 1508-1509.

54. Verdine, G. L., and Hilinski, G. J. (2012) Stapled peptides for intracellular drug targets. *Methods Enzymol.* 503, 3-33.

55. Moellering, R. E., Cornejo, M., Davis, T. N., Del Bianco, C., Aster, J. C., Blacklow, S. C., Kung, A. L., Gilliland, D. G., Verdine, G. L., and Bradner, J. E. (2009) Direct inhibition of the NOTCH transcription factor complex. *Nature* 462, 182-188.

56. Bautista, A. D., Appelbaum, J. S., Craig, C. J., Michel, J., and Schepartz, A. (2010) Bridged beta(3)-peptide inhibitors of p53-hDM2 complexation: correlation between affinity and cell permeability. *J. Am. Chem. Soc.* 132, 2904-2906.

57. Daniels, D. S., and Schepartz, A. (2007) Intrinsically cell-permeable miniature proteins based on a minimal cationic PPII motif. *J. A.m. Chem. Soc.* 129, 14578-14579.

58. Jog, S. P., Paul, S., Dansithong, W., Tring, S., Comai, L., and Reddy, S. (2012) RNA splicing is responsive to MBNL1 dose. *PLoS One* 7, e48825.

59. Teplova, M., and Patel, D. J. (2008) Structural insights into RNA recognition by the alternative-splicing regulator museleblind-like MBNL1. *Nat. Struct. Mol. Biol.* 15, 1343-1351.

60. Warf, M. B., and Berglund, J. A. (2007) MBNL binds similar RNA structures in the CUG repeats of myotonic dystrophy and its pre-mRNA substrate cardiac troponin T. *RNA* 13, 2238-2251.

61. Mooers, B. H., Logue, J. S., and Berglund, J. A. (2005) The structural basis of myotonic dystrophy from the crystal structure of CUG repeats. *Proc. Natl. Acad. Sci. U.S.A* 102, 16626-16631.

62. Sobezak, K., de Mezer, M., Michlewski, G., Krol, J., and Krzyzosiak, W. J. (2003) RNA structure of trinucleotide repeats associated with human neurological diseases. *Nucleic Acids Res.* 31, 5469-5482.

63. Guan, L., and Disney, M. D. (2013) Small molecule-mediated cleavage of RNA in living cells. *Angew. Chem. Int. Ed. Engl.* 52, 1462-1465.

64. Guam, L., and Disney, M. D. (2013) Covalent small molecule-RNA complex formation in living cells enables cellular profiling of small molecule-RNA interactions. *Angew. Chem. Int. Ed. Engl.*, in press.

65. Lin, X., J. W. Miller, J. W., Mankodi, A., Kanadia, R. N., Yuan, Y., Moxley, R. T., Swanson, M. S., and Thornton, C. A. (2006) Failure of MBNL1-dependent post-natal splicing transitions in myotonic dystrophy. *Hum. Mol. Genet.* 15, 2087-2097.

EXAMPLES

Contents:
  1. General Methods
  2. Synthetic Schemes for Modularly Assembled Scaffolds
  3. Synthesis of Modularly Assembled Small Molecules
  4. Characterization of Modularly Assembled Small Molecules
  5. Assessment of Proteolytic Stability
  6. RT-PCR Amplification to Assess Improvement of Splicing Defects in a Cellular Model
  7. Representative Autoradiograms for Improvement of Splicing Defects in a Cellular Model
  8. Comparison of the Bioactivity of 2H-K4NMe and 2H-K4NPr
  9. Description of Cellular Permeability and Toxicity Studies
  10. Representative Flow Cytometry Plots for Modularly Assembled Small Molecules 11. Description of Surface Plasmon Resonance Experiments 12. Binding Isotherms from Surface Plasmon Resonance Experiments 13. Target Pull Down and Northern Blotting 14. RT-PCR Amplification to Assess Improvement of Splicing Defects in a DM1 Mouse Model 15. Representative Autoradiograms for Improvement of Splicing Defects in a DM1 Mouse Model 16. References

1. General Methods

Detailed experimental descriptions for compound synthesis and characterization, RT-PCR analysis, flow cytometry, SPR experiments, target pull down and Northern blotting can be found below.

Time-Resolved Fluorescence Resonance Energy Transfer (TR-FRET) Assay.

Initial in vitro activity of modularly assembled compounds was assessed by disruption of the $r(CUG)^{exp}$-MBNL1 complex using a previously reported TR-FRET assay.[15,47] The ratio of fluorescence intensity of 545 and 665 nm in the presence and absence of compound were used to calculate percent inhibition.

The resulting curves were fit to the following equation to determine $IC_{50}$ values:

$$y = B + \frac{A-B}{1+\left(\frac{IC50}{x}\right)^{hillslope}}$$

where y is the ratio of fluorescence intensities at 545 nm and 665 nm (F545/F665), x is the concentration of small molecule, B is the F545/F665 ratio reflective of the maximum amount of FRET observed (absence of small molecule); A is the F545/F665 ratio reflective of the minimum amount of FRET observed (absence of RNA, protein, and small molecule; only antibodies are present); and the $IC_{50}$ is the concentration of small molecule where half of the protein is displaced by small molecule.

Improvement of DM1-Associated Splicing Defects in a DM1 Cell Culture Model Using RT-PCR.

DM1-associated alternative pre-mRNA splicing defects were assessed using a previously reported model System.[45] Briefly, HeLa cells were grown as monolayers in 96-well plates in growth medium (1X DMEM, 10% FBS, and 1X Glutamax (Invitrogen)). Cells were transfected at 90-95% confluency with 200 ng of total plasmid using Lipofectamine 2000 (Invitrogen) according to the manufacturer's standard protocol. Equal amounts of plasmid expressing a DM1 mini-gene with 960 interrupted CTG repeat[51] and a mini-gene of interest (cTNT[51] or PLEKHH2[43]) were used. After 5 h, the transfection cocktail was removed and replaced with growth medium containing the compound of interest. After 20-24 h, the cells were lysed, and total RNA was harvested using a Sigma-Aldrich GeneElute total mammalian RNA miniprep kit. An on-column DNA digestion was completed per the manufacturer's recommended protocol. A sample of RNA was subjected to RT-PCR as previously described.[15]

Improvement of DM1-Associated Translational Defects Using a Luciferase Model System.

C2C12 cell lines expressing 800 or 0 CTG repeats in the 3' UTR of luciferase were grown as monolayers in 96-well plates in growth medium (1X DMEM, 10% FBS, 1X Glutamax, (Invitrogen) and 1X penicillin/streptomycin (MP Biomedicals LLC)). After 24 h, the compound of interest was added in 50 µL of growth medium. Cells were treated with compound for 24 h. Luciferase activity was determined as previously described.[18]

Treatment in Mice.

All experimental procedures, mouse handling, and husbandry were completed in accordance with the Association for Assessment and Accreditation of Laboratory Animal Care. A mouse model for DM1, $HSA^{LR}$ in line 20b, was used.[24] $HSA^{LR}$ mice express human skeletal actin RNA with 250 CUG repeats in the 3' UTR. Age- and gender-matched $HSA^{LR}$ mice were injected intraperitoncally with 100 mg/kg 2H-K4NMe in water for treatment or 0.9% NaCl for control once per day for 7 days. Mice were sacrificed one day after the last injection, and the vastus muscle was obtained. RNA was extracted from the vastus tissue, and cDNA was synthesized as previously described.[65]

Synthesis.

Fmoc-Rink amide resin (0.59 mmol/g) was purchased from Advanced ChemTech. Wang resin (0.93 mmol/g), 2-chlorotrityl chloride resin (1.2 mmol/g), and Fmoc-L-glycine were purchased from Novabiochem. N,N-dimethylformamide (DMF, anhydrous) was purchased from EMD and used without further purification. Polyamines, 1-propylamine, piperidine, trifluoroacetic acid (TFA), N,N-diisopropylethyl amine (DIEA), 1-ethyl-3-(dimethylaminopropyl) carbodiimide (EDC), and 2-bromoacetic acid were purchased from Sigma Aldrich. N,N'-diisopropylcarbodiimide (DIC), 1-hydroxybenzotriazole (HOBt), 1-hydroxy-7-azabenzotriazole (HOAt), Fmoc-L-alanine alanine, and Fmoc-β-Alanine were purchased from Advanced ChemTech. O-(Benzotriazol-1-yl)-N,N,N',N'-tetramethyluronium hexafluorophosphate (HBTU) and triphosgene were purchased from Oakwood Chemicals. (S) 2-Chloropropionic acid and 2,4,6-collidine were purchased from Alfa Aesar. N-Fmoc ethylene diamine, $N^6$-Boc-$N^2$-Fmoc-L-lysine and Fmoc-N-methyl-L-alanine were purchased from Combi-Blocks. Hoechst carboxylate was synthesized as reported previously.[1] N-methyl peptides were synthesized using a Biotage Initiator+ SP Wave microwave.

Compound Purification and Analysis.

Preparative HPLC was performed using a Waters 1525 Binary HPLC pump equipped with a Waters 2487 dual absorbance detector system and a Waters Sunfire C18 OBD 5 µm 19×150 mm column. Absorbance was monitored at 345 and 220 nm. A gradient of 20-100% methanol (MeOH) in $H_2O$ with 0.1% (v/v) TFA over 60 min was used for compound purification. Analytical HPLC was performed using a Waters Symmetry C18 5 µm 4.6×150 mm column. Polyamines, PTAs and peptoids were analyzed using a gradient of 0-100% MeOH in $H_2O$ with 0.1% (v/v) TFA over 60 min. Peptides were analyzed using a gradient of 0-100% acetonitrile in $H_2O$ with 0.1% (v/v) TFA over 60 min. All compounds evaluated had ≥95% purity by analytical HPLC. Mass spectrometry was performed with an Applied Biosystems MALDI ToF/ToF Analyzer 4800 Plus using an α-hydroxycinnamic acid matrix.

Synthetic Schemes for Modularly Assembled Scaffolds

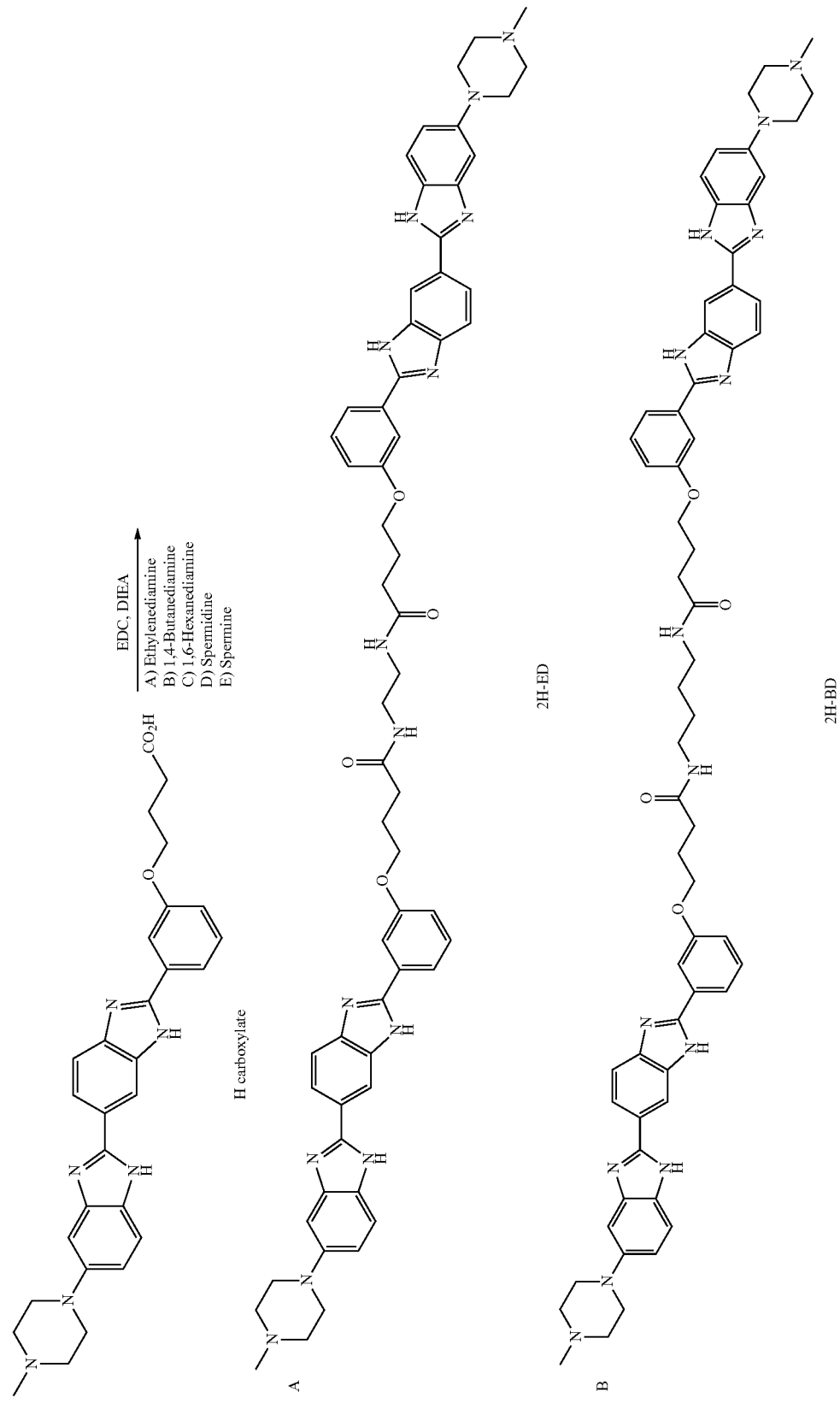

-continued
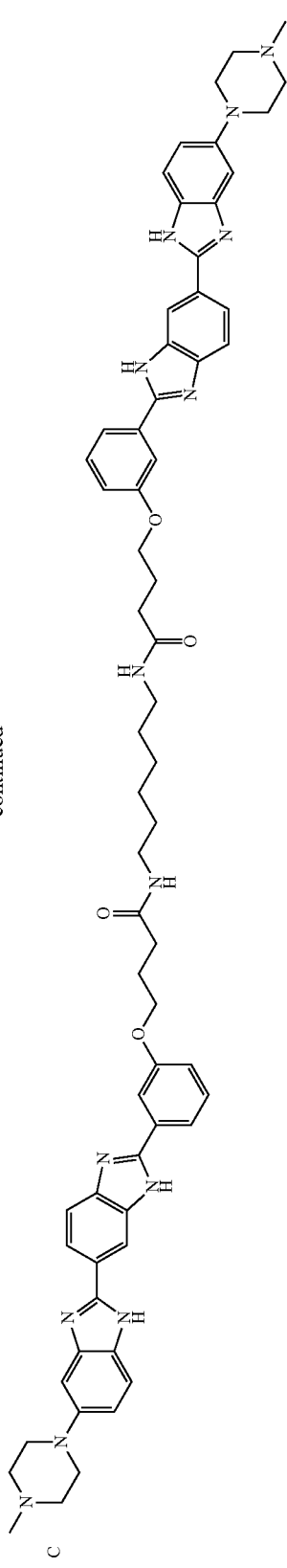
2H-HD
C
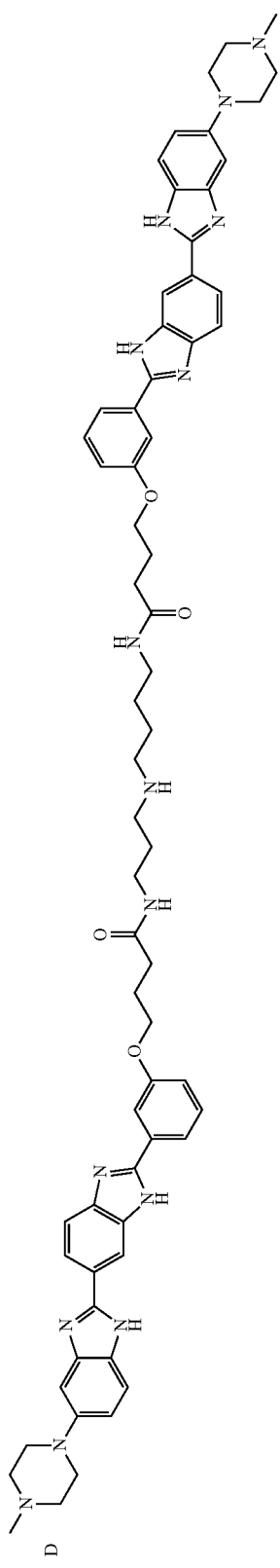
2H-SPD
D
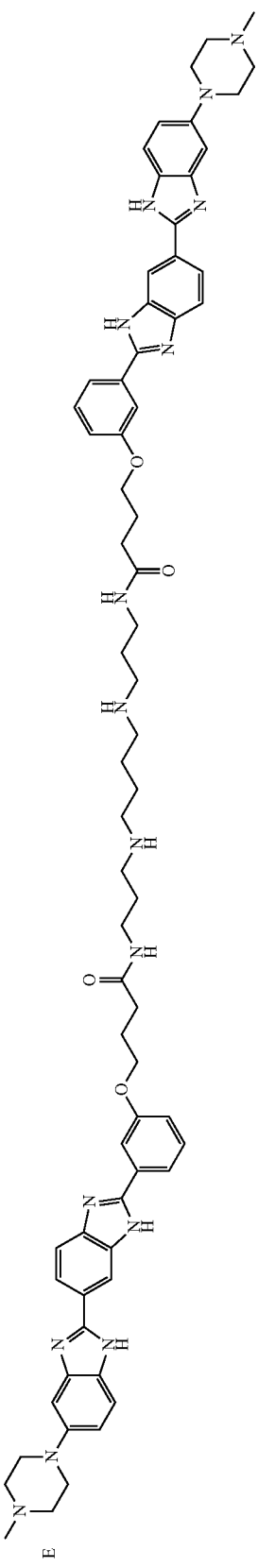
2H-SPM
E

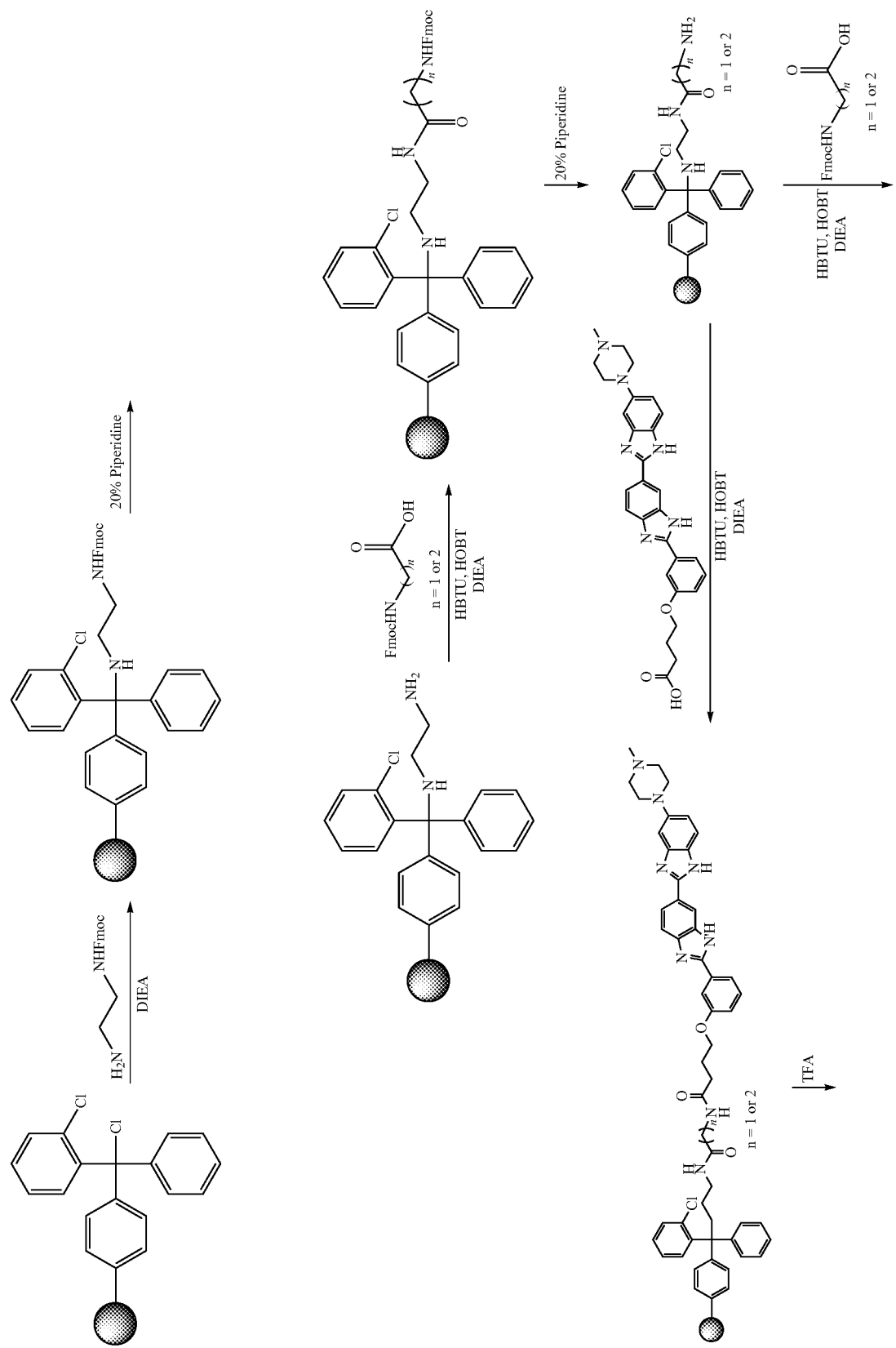
Scheme 2. Synthesis of a and b Peptides.

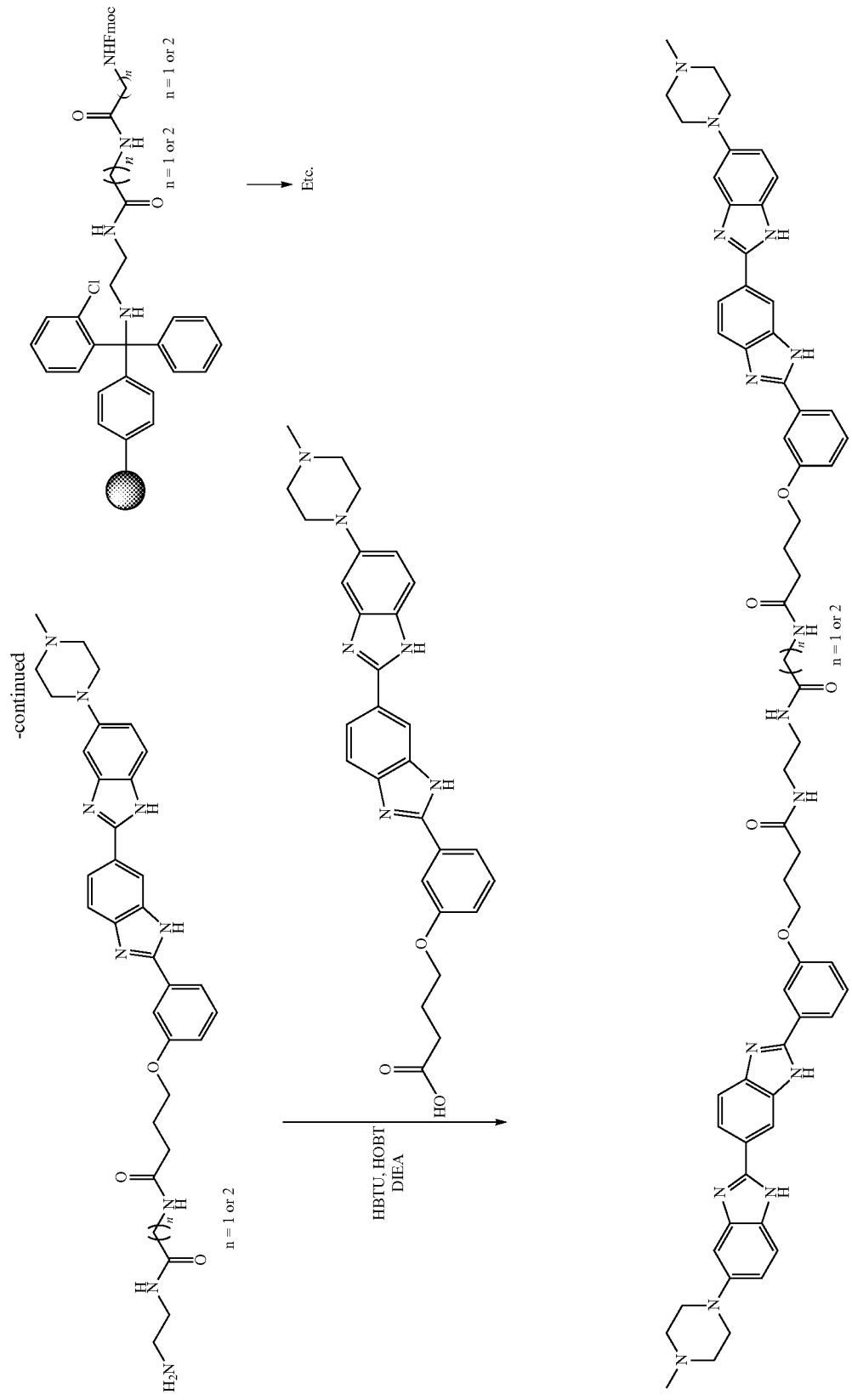

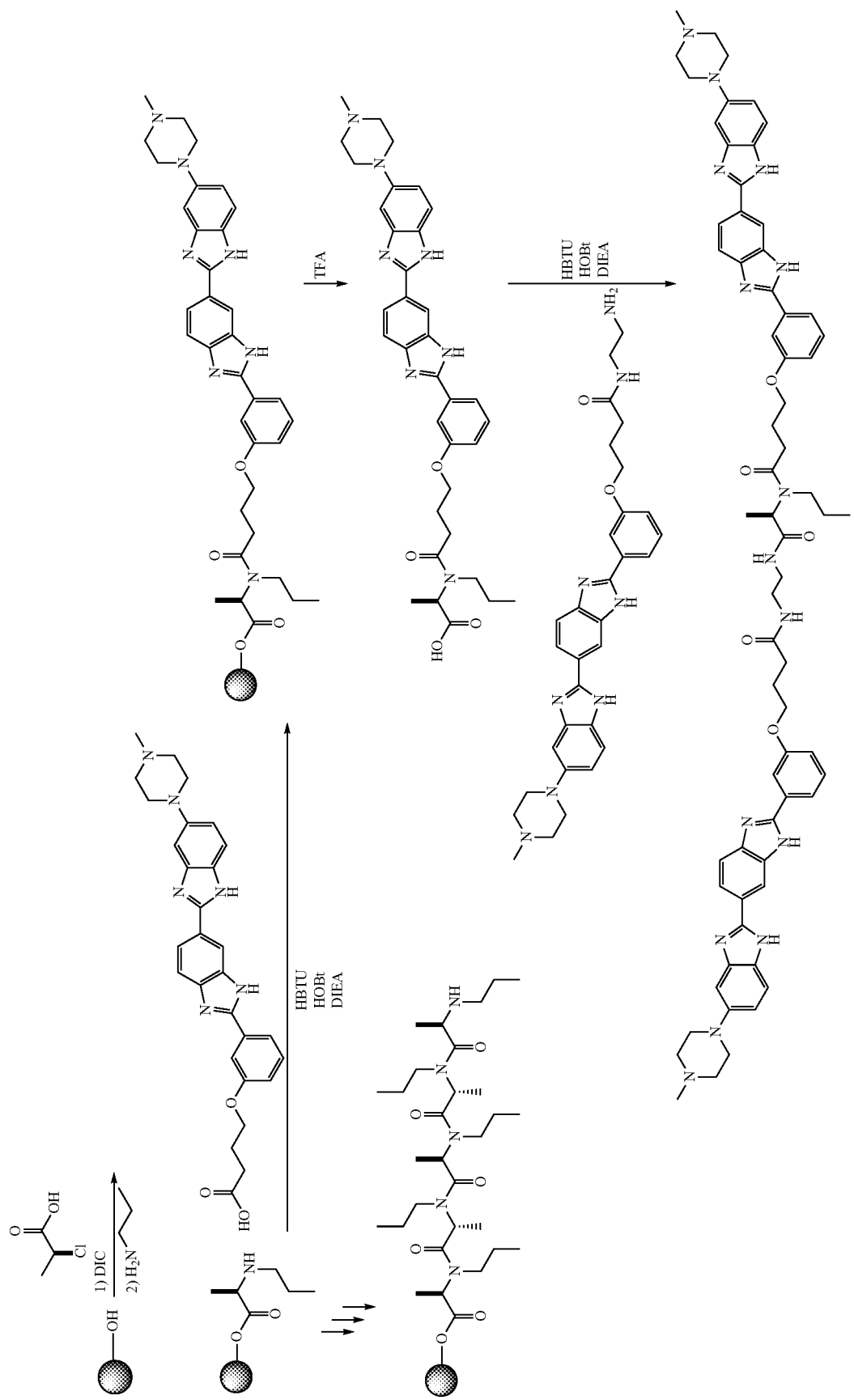
Scheme 3. Synthesis of Peptide Tertiary Amides.

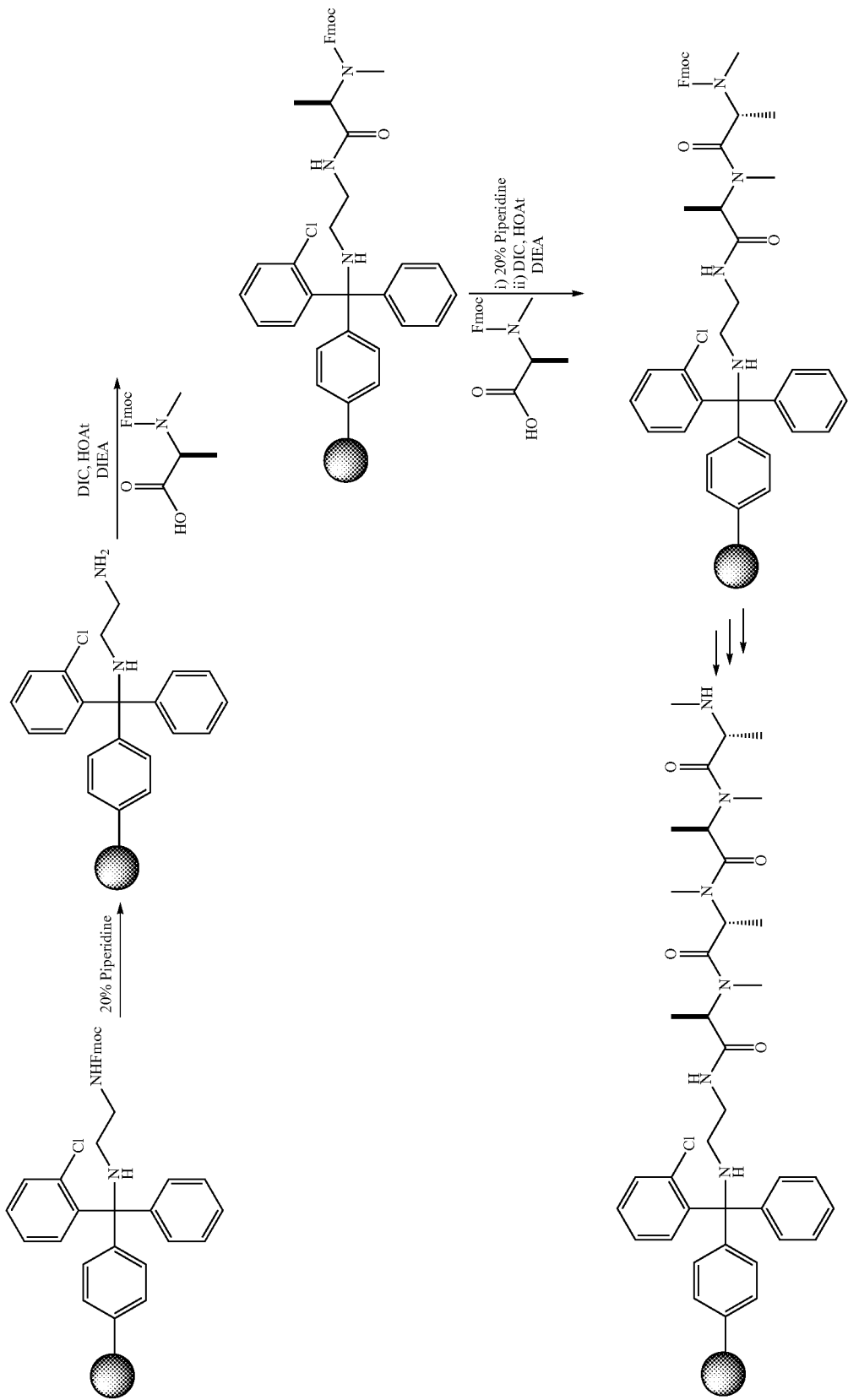

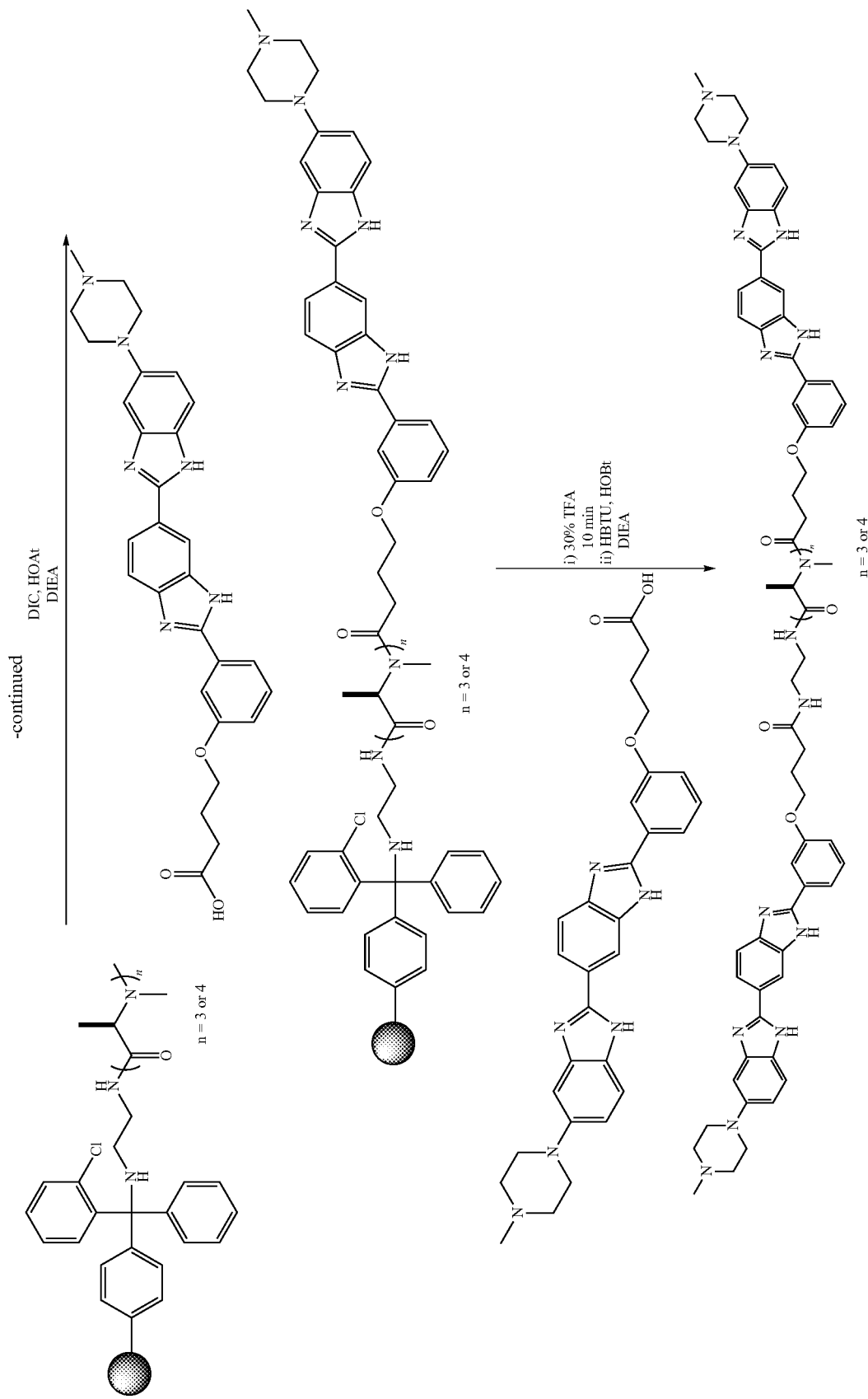

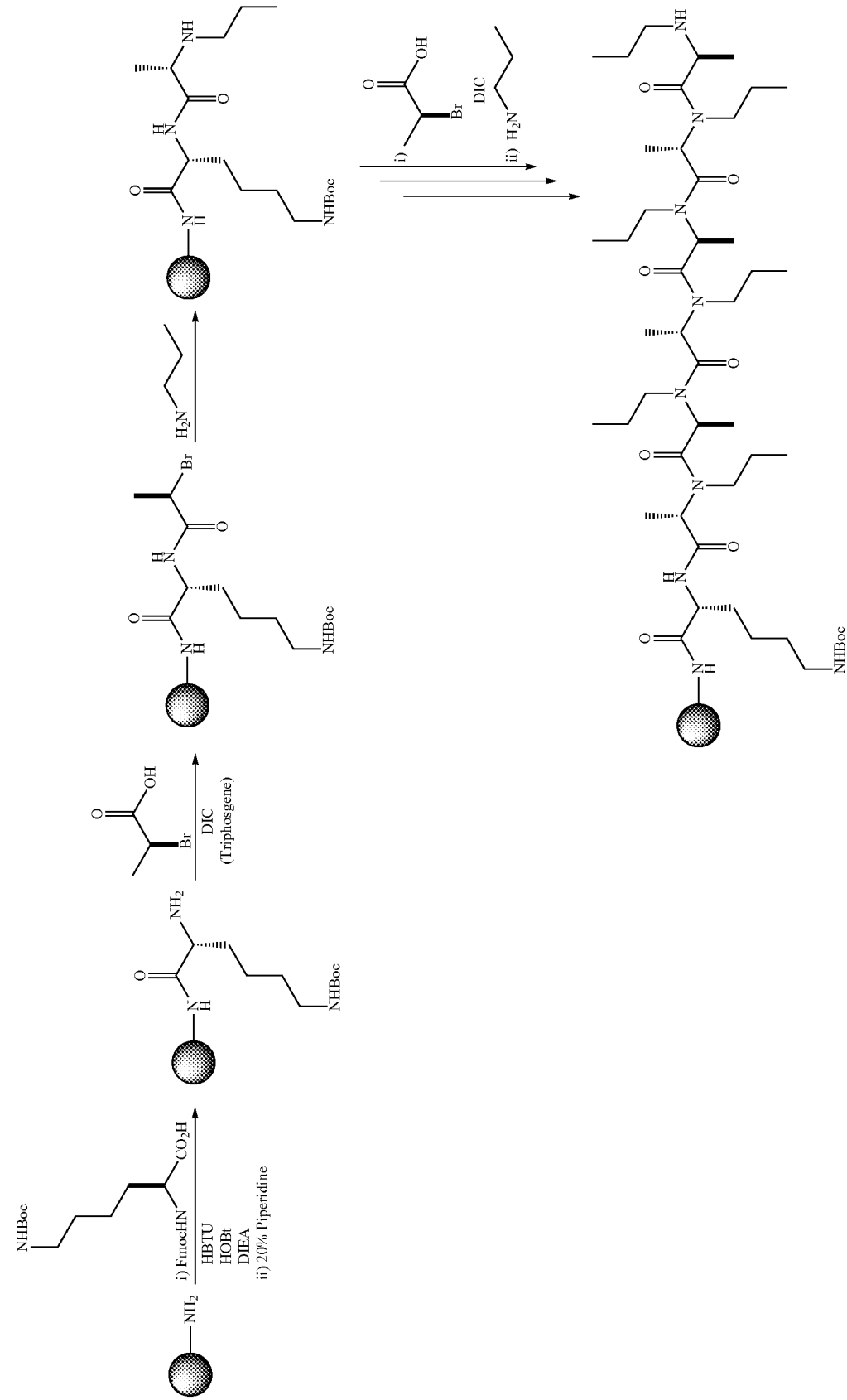
Scheme 5. Synthesis of Lysine Peptide Tertiary Amides

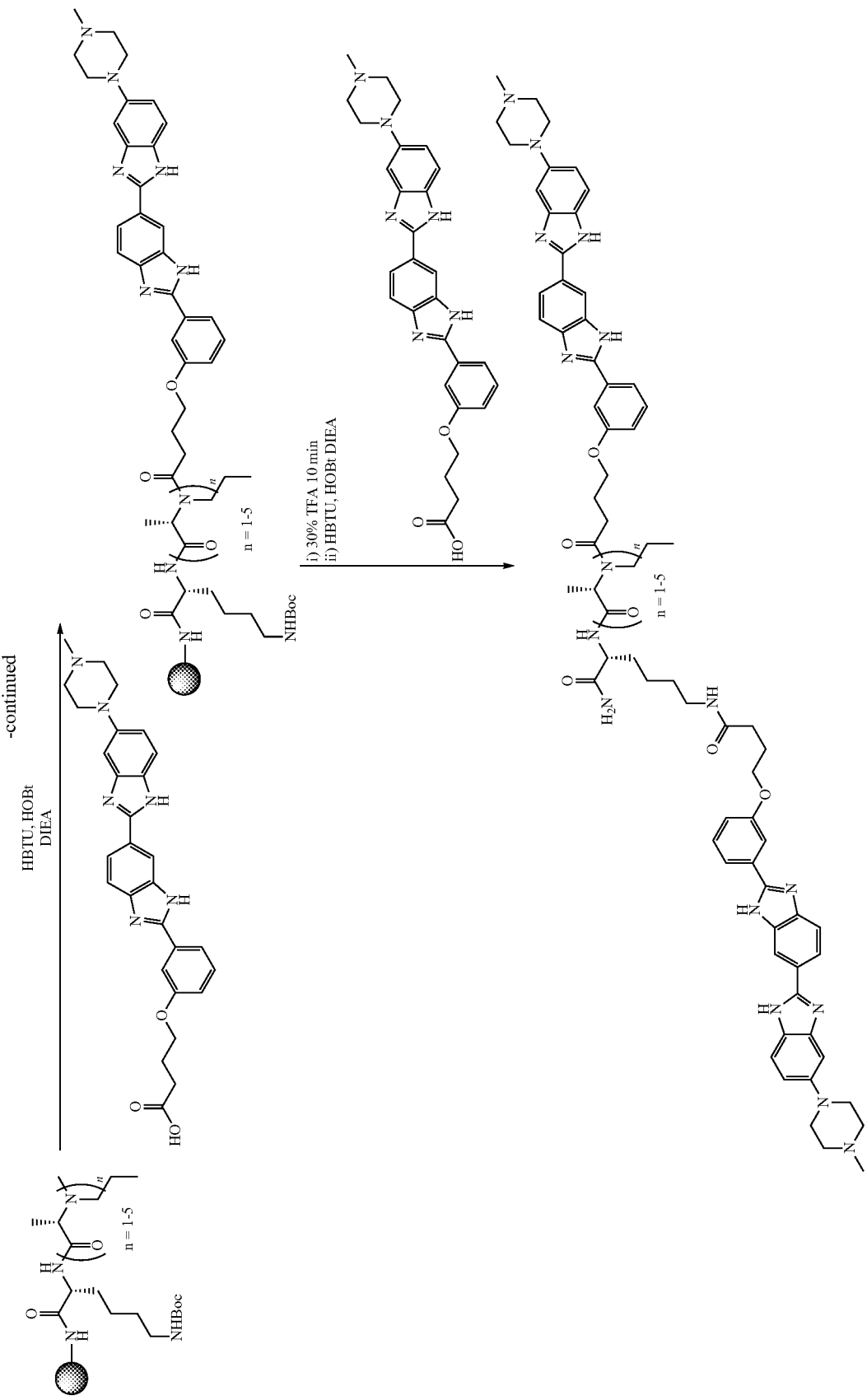

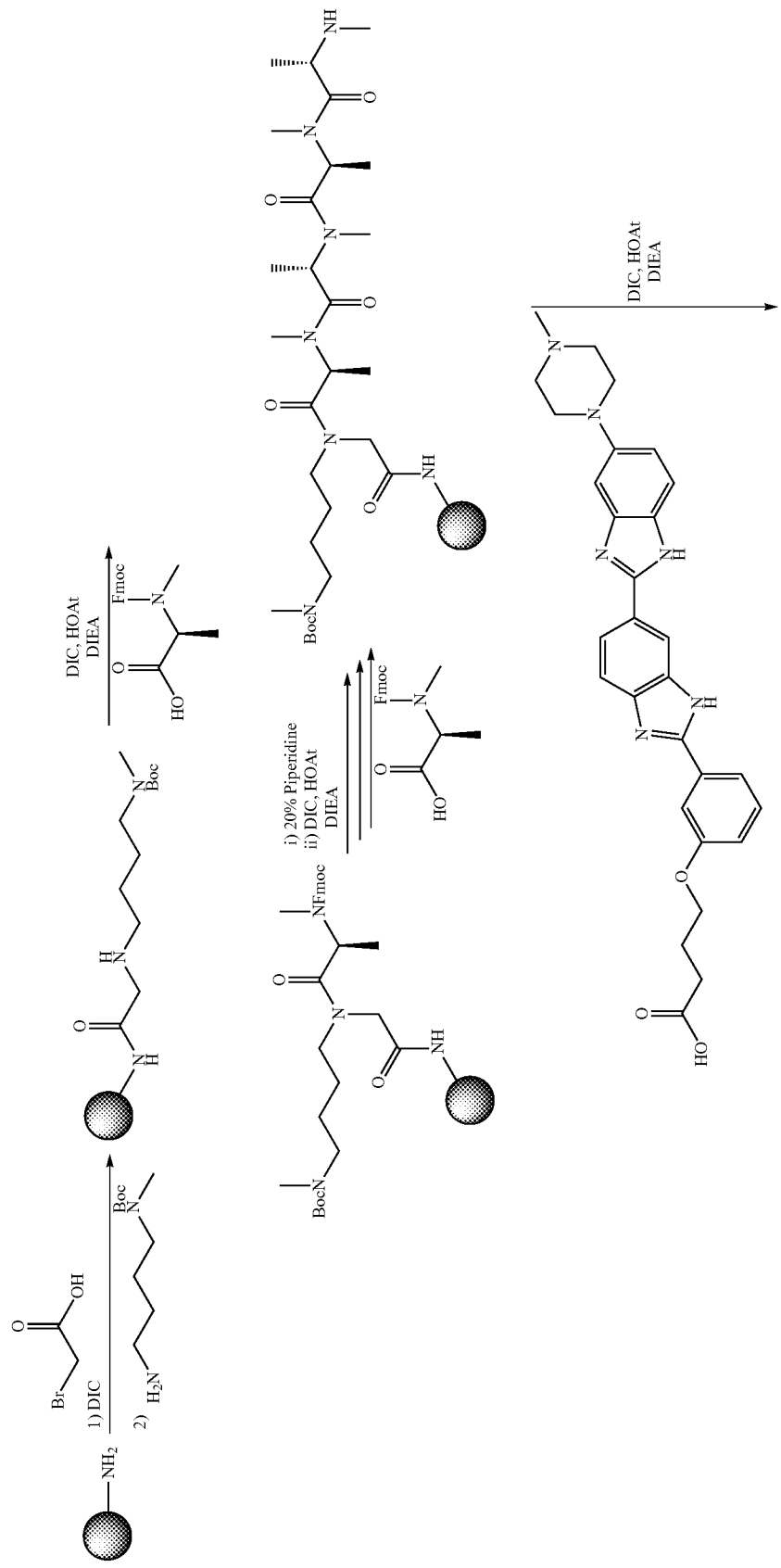

-continued
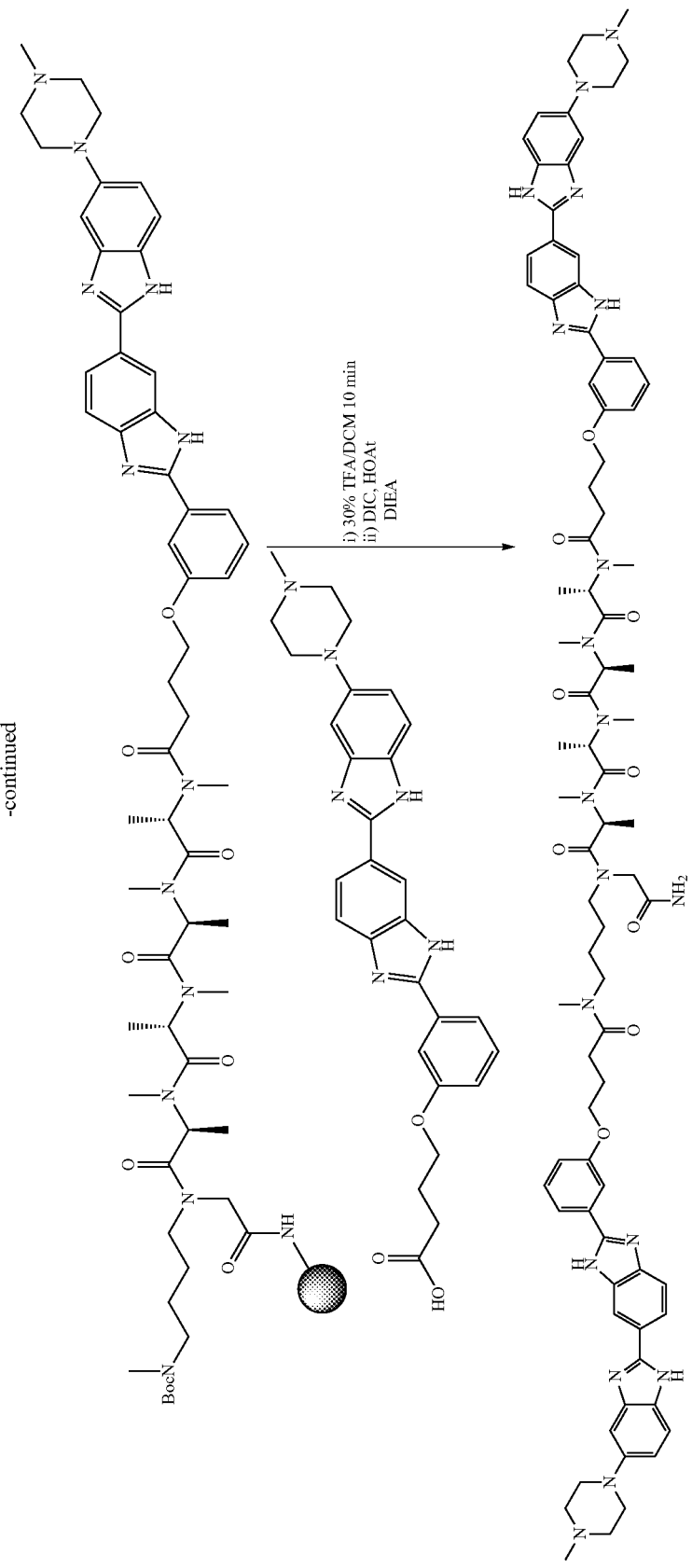

Synthesis of Modularly Assembled Small Molecules

Synthesis of Polyamines.

A solution of diamine (0.02 mmol) in DMF (200 μL) was treated with a solution of H carboxylate (20 mg, 0.04 mmol), EDC (12 mg, 0.06 mmol) and DEA (10 μL, 0.06 mmol) in DMF (200 μL). The reaction was stirred at room temperature overnight and then the solvent was removed in vacuo. The reaction mixture was purified using reverse phase HPLC. 2H-ED ($C_{60}H_{64}N_{14}O_4$): MS calculated: 1045.5; MS found: 1045.6; $t_R$=31 mm; yield=5%; 2H-BD ($C_{62}H_{68}N_{14}O_4$): MS calculated: 1073.6; MS found: 1073.8; $t_R$=31 min; yield=2%; 2H-HD ($C_{64}H_{72}N_{14}O_4$): MS calculated: 1101.6; MS found: 1101.9; $t_R$=32 min; yield=1%; 2H-SPD ($C_{65}H_{75}N_{15}O_4$): MS calculated: 1131.4; MS found: 1131.0; $t_R$=44 min ($CH_3CN/H_2O$); yield=0.2%; 2H-SPM ($C_{68}H_{82}N_{16}O_4$): MS calculated: 1188.5; MS found: 1188.1; $t_R$=31 min; yield=3%.

Synthesis of Ethylene Diamine Resin.

2-Chlorotrityl chloride resin (3 g, 3.66 mmol, 1.22 mmol/g) was treated with a solution of N-Fmoc ethylene diamine (1.5 g, 5.32 mmol,) and DIEA (3.2 mL, 18.3 mmol, 5 eq) in DMF (10 mL). The mixture was shaken at room temperature overnight, and then the resin was washed with DMF. The resin was treated with MeOH for 10 min and then deprotected with 20% piperidine/DMF (2×20 min).

Synthesis of α- and β-peptides.

Ethylene diamine resin (1.25 g, 1.5 mmol) was treated with a solution of HBTU (2.28 g, 6 mmol,), HOBt (811 mg, 6 mmol), DIEA (2.1 mL, 12 mmol), and either Fmoc-glycine or Fmoc β-alanine (6 mmol) in DMF (15 mL) and shaken at room temperature overnight. Then resin was washed with DMF and deprotected with 20% piperidine/DMF (5 mL, 2×20 min). This cycle was repeated five times, and a portion of the resin (100 mg) was removed after each cycle. 2H-1G ($C_{62}H_{67}N_{15}O_5$): MS calculated: 1102.5; MS found: 1102.5; $t_R$=42 min; 2H-2G ($C_{64}H_{70}N_{16}O_6$): MS calculated: 1159.6; MS found: 1159.5; $t_R$=42 min; 2H-3G ($C_{66}H_{73}N_{17}O_7$): MS calculated: 1216.6; MS found: 1216.2; $t_R$=42 min; 2H-4G ($C_{68}H_{76}N_{18}O_8$): MS calculated: 1273.6; MS found: 1273.7; $t_R$=41 min; 2H-5G ($C_{70}H_{79}N_{19}O_9$): MS calculated: 1330.6; MS found: 1330.4; $t_R$=41 min; 2H-6G ($C_{72}H_{82}N_{20}O_{10}$): MS calculated: 1387.7; MS found: 1387:7; $t_R$=45 min; 2H-1βA ($C_{63}H_{69}N_{15}O_5$): MS calculated: 1116.6; MS found: 1116.2; $t_R$=43 min; 2H-2βA ($C_{66}H_{74}N_{16}O_6$): MS calculated: 1187.6; MS found: 1187.7; $t_R$=43 min; 2H-3βA ($C_{69}H_{79}N_{17}O_7$): MS calculated: 1258.6; MS found: 1258.7; $t_R$=43 min; 2H-4βA ($C_{72}H_{84}N_{18}O_8$) MS calculated: 1329.7; MS found: 1329.5; $t_R$=44 min; 2H-5βA ($C_{75}H_{89}N_{19}O_9$): MS calculated: 1400.7; MS found: 1400.4; $t_R$=43 min; 2H-6βA ($C_{78}H_{94}N_{20}O_{10}$): MS calculated: 1471.8; MS found: 1471.3: $t_R$=43 min.

Synthesis of Peptide Tertiary Amides.

Wang resin (1 g, 0.93 mmol) was shaken with (S)-2-chloropropionic acid (500 μL, 5.4 mmol) and DIC (845 μL, 5.4 mmol) in DMF at room temperature for 3 h. The resin was then washed with DMF, treated with a solution of 1-propylamine (500 μL, 6 mmol) in DMF (5 mL), and shaken at room temperature for 3 h. The resin was washed with DMF, and a portion of the resin (200 mg) was removed after each cycle. The remaining resin was carried through four additional cycles of coupling and displacement. 2H-1NPr ($C_{66}H_{75}N_{15}O_5$): MS calculated: 1158.6; MS found: 1158.6; $t_R$=33 min; 2H-2NPr ($C_{72}H_{86}N_{16}O_6$): MS calculated: 1270.7; MS found: 1270.9; $t_R$=35 min; 2H-3NPr ($C_{73}H_{97}N_{17}O_7$): MS calculated: 1385.7; MS found: 1385.8; $t_R$=31 min; 2H-4NPr- ($C_{84}H_{108}N_{18}O_8$): MS calculated: 1496.9; MS found: 1496.8; $t_R$=35 min.

Synthesis of N-methyl Peptide Tertiary Amides.

Ethylene diamine resin (250 mg, 0.31 mmol) was treated with a solution of DIC (143 μL, 0.92 mmol), HOAt (125 mg, 0.92 mmol), DIEA (313 μL, 1.8 mmol), and Fmoc-N-methyl-L-alanine (300 mg, 0.92 mmol) in anhydrous DMF (2 mL). The reaction mixture was heated to 75° C. via microwave for 20 min. The resin was then washed with DMF and deprotected with 20% piperidine/DMF (2.5 mL, 2×10 min). This cycle was repeated three times, and then half of the resin was removed. The remaining resin was subjected to one additional cycle. 2H-3NMe ($C_{72}H_{85}N_{17}O_7$): MS calculated: 1300.7; MS found: 1300.8; $t_R$=32 min; 2H-4NMe ($C_{76}H_{92}N_{18}O_8$): MS calculated: 1386.7; MS found: 1386.0; $t_R$=31 min.

Synthesis of Lysine Peptide Tertiary Amides: DIC Method.

Deprotected Rink amide resin (1 g, 0.59 mmol) was treated with a solution of $N^6$-Boc-$N^2$-Fmoc-L-lysine (829 mg, 1.8 mmol, 3 eq), HBTU (880 mg, 2.4 mmol, 4 eq), HOBt (320 mg, 2.4 mmol, 4 eq), and DIEA (820 μL, 4.7 mmol, 8 eq) in DMF (10 mL). The mixture was shaken at room temperature for 4 h. The resin was washed with DMF and treated with 20% piperidine/DMF (5 mL, 2×20 min). The resin was treated with DIC (1 mL, 6.4 mmol,) and (S)-2-chloropropionic acid (500 μL, 0.6 mmol) and shaken at room temperature for 3 h. The resin was then washed with DMF and resuspended in 5 mL of DMF. Next, 1-propylamine (500 μl, 12 mmol) was added, and the resin was shaken at room temperature for 4 h followed by washing with DMF. A portion of the resin (200 mg) was removed, and this cycle was repeated four more times. 2H-K1NPr ($C_{70}H_{82}N_{16}O_6$): MS calculated: 1243.7; MS found: 1243.5; $t_R$=33 min; 2H-K2NPr ($C_{76}H_{93}N_{17}O_7$): MS calculated: 1356.7; MS found: 1356.1; $t_R$=34 Min; 2H-K3NPr ($C_{82}H_{104}N_{18}O_8$): MS calculated: 1469.8; MS found: 1469.6; $t_R$=35 min; 2H-K4NPr ($C_{88}H_{115}N_{19}O_9$): MS calculated: 1582.9; MS found: 1582.7; $t_R$=35 min; 2H-K5NPr ($C_{94}H_{126}N_{20}O_{10}$): MS calculated: 1696.0; MS found: 1696.4; $t_R$=35 min.

Synthesis of Lysine Peptide Tertiary Amides: Triphosgene Method.

Deprotected Rink amide resin (250 mg, 0.05 mmol, 0.2 mmol/g) was treated with a solution of $N^6$-Boc-$N^2$-Fmoc-L-lysine (65 mg, 0.14 mmol), HBTU (69 mg, 0.19 mmol), HOBt (25 mg, 0.19 mmol), and DIEA (65 μL, 0.37 mmol) in DMF (1 mL) and shaken at room temperature for 4 h. The resin was washed with DMF, followed by removal of the Fmoc by treatment with 20% piperidine/DMF (2 mL, 2×20 min) and washing with DCM and THF. (The THF wash step was completed with shaking for 5 min.) Most of the solvent was then drained from the resin, and DIEA (87 μL, 0.5 mmol) was added. Triphosgene (75 mg, 0.25 mmol) was dissolved in anhydrous THF (3.65 mL) and (S)-2-chloropropionic acid (23 μL, 0.25 mmol) was added. This solution was incubated at −80° C. for 15 min. Then 2, 4, 6-collidine (66 μL, 0.5 mmol) was added, affording precipitation of a white solid. This cold solution was added to the resin and shaken at room temperature for 3 h. After, the resin was washed with DCM and DMF, and then a solution of 1-propylamine (250 μL, 6 mmol) in DMF (3 mL) was added. The resin was shaken at room temperature for 4 h and then washed with DMF and DCM. This cycle was repeated a total of four times.

2H-K4NiBu ($C_{92}H_{123}N_{19}O_9$): MS calculated: 1639.0; MS found: 1639.2; $t_R$=31 min.

Synthesis of Lysine N-methyl Peptide Tertiary Amide.

Deprotected Rink amide resin (200 mg, 0.12 mmol) was shaken with a solution of $N^6$-Boc-$N^2$-Fmoc-L-lysine (262 mg, 0.56 mmol), HBTU (203 mg, 0.56 mmol), HOBt (75 mg, 0.56 mmol) and DIEA (98 μL, 0.56 mmol) in DMF (2 mL) for 4 h and then the Fmoc was removed with 20% piperidine/DMF (3 mL, 2×20 min). A solution of Fmoc-N- methyl-L-alanine (100 mg, 0.3 mmol), DIC (48 µL, 0.9 mmol). HOAt (41 mg, 0.9 mmol), and DIEA (104 µL, 0.9 mmol) in DMF (2 mL) was added, and the reaction was heated via microwave to 75° C. for 10 min. The resin was washed with DMF, and the Fmoc was removed with 20% piperidine/DMF (2×10 min). This cycle was repeated a total of four times. K4NMe ($C_{22}H_{43}N_7O_5$): MS calculated: 486.3; MS found: 486.4; $t_R$=10 min; 2H-K4NMe ($C_{80}H_{99}N_{19}O_9$): MS calculated: 1470.8; MS found: 1470.6; $t_R$=32 min.

Synthesis of Lysine Alanine Peptide.

Deprotected Rink amide resin (250 mg, 0.15 mmol) was shaken with a solution of $N^6$-Boc-$N^2$-Fmoc-L-lysine (275 mg, 0.6 mmol), HBTU (247 mg, 0.6 mmol), HOBt (88 mg, 0.6 mmol), and DIEA (226 µL, 0.6 mmol) in DMF (2 mL) for 4 h, and then the Fmoc was removed with 20% piperidine/DMF (3 mL, 2×20 min). Next, the resin was treated with a solution of Fmoc-L-alanine (200 mg, 0.6 mmol), HBTU (247 mg, 0.6 mmol), HOBt (88 mg, 0.6 mmol), and DIEA (226 µL, 0.6 mmol) in DMF (2 mL) for 4 h followed by deprotection of the Fmoc with 20% piperidine/DMF (3 mL, 2×20 min). This cycle was repeated three more times. 2H-K4NH ($C_{76}H_{91}N_{19}O_9$): MS calculated: 1414.7; MS found: 1414.6; $t_R$=31 min.

Synthesis of Lysine Peptoid.

Deprotected Rink amide resin (250 mg, 0.15 mmol) was shaken with a solution of $N^6$-Boc-$N^2$-Fmoc-L-lysine (275 mg, 0.6 mmol), HBTU (247 mg, 0.6 mmol), HOBt (88 mg, 0.6 mmol), and DIEA (226 µL, 0.6 mmol) in DMF (2 mL) for 4 h, and then the Fmoc was removed with 20% piperidine/DMF (3 mL, 2×20 min). The resin was washed with DMF (3×5 mL) and reacted twice with a solution of 1M bromoacetic acid (2 mL) and DIC (250 µL, 1.5 mmol) in DMF (2 mL) via microwave irradiation (3×15 s) using a 700 W microwave set to 10% power. The resin was washed with DMF (3×15 mL) and reacted twice with a solution of 1-propylamine (250 µL, 0.6 mmol) in DMF (2 mL) via microwave irradiation (3×15 s) using a 700 W microwave set to 10% power. The resin was washed with DMF (3×5 mL), and the coupling and displacement steps were repeated for three more cycles. 2H-K4 ($C_{84}H_{127}N_{19}O_9$): MS calculated: 1526.9; MS found: 1526.7; $t_R$=35 min.

Synthesis of Biotinylated 2H-K4NMe.

Deprotected Rink amide resin (200 mg, 0.12 mmol) was reacted with a 1M solution of 2-bromoacetic acid (2 mL) and DIC (60 µL, 0.4 mmol) by heating via microwave to 75° C. for 5 min. The resin was washed with DMF, treated with a solution of 3-azidopropylamine (40 mg, 0.4 mmol) in DMF, and heated in the microwave reactor to 75° C. for 5 min. The resin was washed with DMF and then a solution of $N^6$Boc-$N^2$-Fmoc-L-lysine (164 mg, 0.35 mmol), DIC (60 µL, 0.4 mmol), HOAt (50 mg, 0.4 mmol) and DIEA (60 µL, 0.4 mmol) in DMF (2 mL) was added. The reaction was heated via microwave to 75° C. for 10 min, followed by washing the resin with DMF. Next, the Fmoc was removed with 20% piperidine/DMF (2×10 min), a solution of Fmoc-N-methyl-L-alanine (100 mg, 0.3 mmol), DIC (60 µL, 0.4 mmol), HOAt (50 mg, 0.4 mmol), and DIEA (60 µL, 0.4 mmol) in DMF (2 mL) was added, and the reaction was heated via microwave to 75° C. for 10 min. The resin was washed with DMF and the Fmoc was removed with 20% piperidine/DMF (2×10 Min). This cycle was repeated a total of four times. Biotin was then attached to the peptide via click reaction using a previously described method.[2] Briefly, the beads were then microwaved with a solution of biotin alkyne (166 mg, 0.6 mmol), copper (1) catalyst (20 mg, 0.08 mmol), and triethylamine (200 µL) in a 1:1 mixture of DMF and water (2 mL) at 110° C. for 2 h. K4NMe Biotin ($C_{40}H_{70}N_{14}O_8S$): MS calculated: 907.52; MS found: 907.44; to $t_R$=17 min. The 2H-K4NMe Biotin ($C_{98}H_{126}N_{26}O_{12}S$) compound was obtained after H-carboxylate coupling as described for 2H-K4NMe. 2H-K4NMe Biotin ($C_{98}H_{126}N_{26}O_{12}S$): MS calculated: 1891.98; MS found: 1891.85; $t_R$=33 min.

Synthesis of 2H-K4NMeS (Stable Lysine Peptide Tertiary Amide).

Deprotected Rink amide resin (1 g, 0.59 mmol) was reacted with a solution of 2-bromoacetic acid (500 mg, 3.6 mmol) and DIC (554 µL, 3.6 mmol) in dry DMF (5 mL). This was reacted in a conventional microwave 3×15 s at 10% power. This was repeated one time. Then the resin was washed with dry DMF and then treated with a solution of N-(4-aminobutyl)-N-methyl carbamic acid tert-butyl ester (200 mg, 1 mmol) in dry DMF (5 mL). This was reacted in a conventional microwave 3×15 s at 10% power and then shaken at room temperature for 15 min. Then treated with a solution of Fmoc-N-methylalanine (290 mg, 0.89 mmol), DIC (277 µL, 1.77 mmol), HOAt (241 mg, 1.77 mmol) and DIEA (308 µL, 1.77 mmol) in dry DMF (5 mL) and reacted at 75° C. for 10 minutes using the Biotage SP-Wave microwave synthesizer. The resin was then transferred to a peptide synthesis vessel and washed with DMF. Then the Fmoc was deprotected by shaking at room temperature with 20% piperidine/DMF (5 mL) for 2×10 min. This cycle was repeated 3 more times. After a total of 4 couplings and deprotections the resin was reacted with a solution of Hoechst carboxylate (300 mg, 0.59 mmol), DIC (277 µL, 1.77 mmol), HOAt (241 mg, 1.77 mmol) and DIEA (308 µL, 1.77 mmol) in dry DMF (5 mL) by microwaving at 75° C. for 10 min using the Biotage SP-Wave microwave synthesizer. Then the resin was washed with DMF and DCM and cleaved with 30% TFA/DCM at rt for 10 min. Immediately concentrated and azeotroped with toluene 3×. UV indicated about 20 µmoles of product. The yellow oil was dissolved in dry DMF (1.5 mL) and added Hoechst carboxylate (10 mg, 20.3 µmoles), HOAt (3 mg, 22.3 µmoles), DIC (6 µL, 44.6 µmoles) and DIEA (250 µL). This was microwaved at 75° C. for 10 min using the Biotage SP-Wave microwave synthesize and then the solution was concentrated in vacuo. Purified by reverse phase HPLC as described above. Isolated 2.52 µmoles of product, 3.7 mg. 2H-K4NMeS ($C_{81}H_{102}N_{19}O_9$): MS calculated: 1484.80; MS found: 1484.55; $t_R$=31 min.

General Procedure for H Carboxylate Conjugation to Peptides and Peptide Tertiary Amides. Free amine resin (100 mg, 0.12 mmol) was treated with a solution of Hoechst carboxylate (81 mg, 0.16 mmol, 1.3 eq), HBTU (185 mg, 0.5 mmol, 4 eq), HOBt (68 mg, 0.5 mmol, 4 eq) and DIEA (0.2 mL, 1.2 mmol, 10 eq) in DMF (5 mL) at room temperature overnight. The solution was removed, the resin was washed with DMF and DCM, and then treated with 30% TFA/DCM (2 mL) for 10 min. The solution was concentrated in vacuo and azeotroped with toluene three times. The quantity of product was approximated by UV absorbance. The resin was treated with a solution of Hoechst carboxylate (5.5 mg, 0.01 mmol, 2 eq), HBTU (8 mg, 0.01 mmol, 2 eq), HOBt (2 mg, 0.01 mmol, 2 eq) and DIEA (70 µL, 0.4 mmol, 80 eq) in DMF (1 mL) overnight at room temperature. The solvent was removed in vacuo, and the product was purified using reverse phase HPLC as described above.

Analytical Data.

HPLC purity and mass spectrometry data were obtained for all of compounds 2H-ED, 2H-BD, 2H-HD, 2H-SPD, 2H-SPM, 2H-1G, 2H-2G, 2H-3G, 2H-4G, 2H-5G, 2H-6G, 2H-1βA, 2H-2βA, 2H-3βA, 2H-4βA, 2H-5βA, 2H-6βA, 2H-1NPr, 2H-2NPr, 2H-3NPr, 2H-4NPr, 2H-3NMe, 2H-4NMe, 2H-K1NPr, 2H-K2NPr, 2H-K3NPr, 2H-K4NPr, 2H-K5NPr, K4NMe, 2H-K4NMe, 2H-K4NH, 2H-K4NiBu, 2H-K4, K4NMe Biotin, and 2-K4NMe Biotin.

RT-PCR Amplification to Assess Improvement of Splicing Defects in a Cellular Model Approximately 300 ng of total RNA was reverse transcribed at 42° C. using 5 units of AMV reverse transcriptase (Life Sciences). Half of the RT reaction was subjected to PCR using a radioactively labeled forward primer. RT-PCR products were observed after 30-35 cycles of 95° C. for 1 min, 55° C. for 1 min, 72° C. for 2 min and a final extension at 72° C. for 10 min. The products were separated on a 5% denaturing polyacrylamide gel and imaged using a Molecular Dynamics Typhoon 9410 variable mode imager. The RT-PCR primers for the cTNT mini-gene were 5'GTTCACAACCATCTAAAGCAAGATG (forward; SEQ ID NO:1) and 5' GTTGCATGGCTGGTGCAGG (reverse; SEQ ID NO:2). The RT-PCR primers for the PLEKKH2 mini-gene were 5' CGGGGTACCAAATGCTGCAGTTGACTCTCC (forward; SEQ ID NO:3) and 5'CCGCTCGAGCCATTCATGAAGTGCACAGG (reverse; SEQ ID NO:4).

Description of Cellular Permeability and Toxicity Studies

HeLa cells were grown in 12-well plates in growth medium (1X DMEM, 10% FBS, and 1X Glutamax (Invitrogen)) for 24 h until they reached 90-95% confluency. The growth medium was removed and replaced with 750 μL of fresh medium containing the compound of interest. Cells were treated for 24 h and then washed with 1X DPBS. The cells were trypsinized, pelleted, and washed twice with ice-cold 1X DPBS. Cells were resuspended in 1X DPBS containing 1 propidium iodide (Sigma Aldrich) and incubated on ice for 30 min. Analysis of 10,000 events was completed using a BD LSRII flow cytometer using standard forward and side scatter metrics. Cells were compared to controls treated with medium alone. Propidium iodide staining was used to detect cells that are grossly intact but are permeabilized. PI was detected using a 561 nm laser. Hoechst 33258 was used as a positive control for gating 2H-X compounds. H was detected using a UV laser (355 nm). Gates for positive staining were created in relation to untreated, unstained cells; untreated, PI stained cells; and Hoechst 33258 treated cells.

Kinetic Studies Using Surface Plasmon Resonance

Figure 25C:
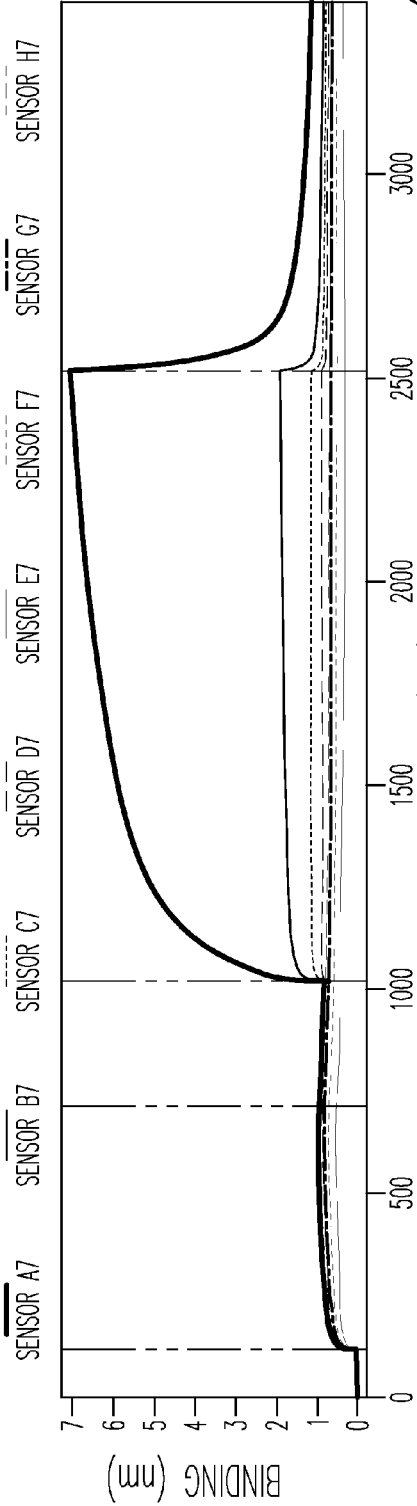
Figure 25D:
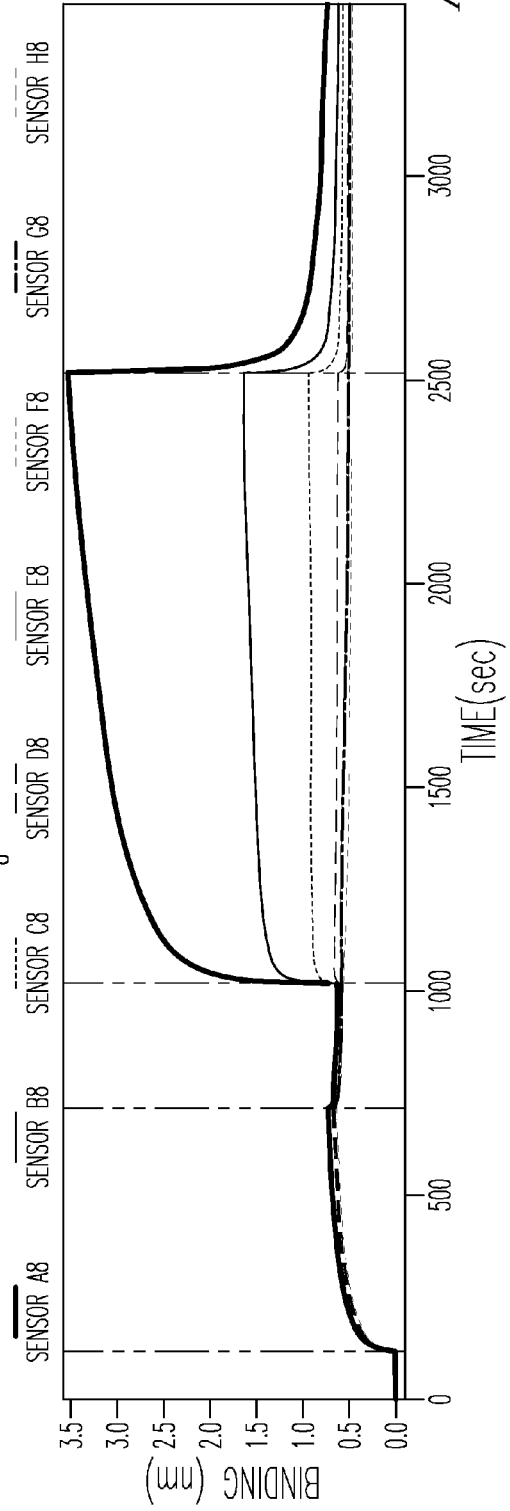

On rates, off rates and $K_{obs}$ values were measured using a ForteBio OctetRed spectrophotometer and Streptavidin SA dip-and-read biosensors (ForteBio). Sensors were pre-equilibrated in 1X Kinetics Buffer (ForteBio) prior to beginning measurements. 5'-Biotinylated r(CUG)$_{12}$ was folded by heating in 1X Kinetics Buffer at 60° C. for 5 min followed by slow cooling to room temperature on the bench top. Measurements were completed by incubating sensors sequentially in 200 μL of: 1X Kinetics Buffer, 540 nM 5'-biotinylated RNA, 1X Kinetics Buffer, compound of interest or MBNL1 (varying concentrations; seven 1:2 dilutions in 1X Kinetics Buffer), and finally 1X Kinetics Buffer. Data were fit using ForteBio's Data Analysis 7.0 software. MBNL1 and II (monomer) data were fit using a 1:1 model. This model fits one analyte in solution binding to one binding site on the surface. 2H-K4NMe and 2H-4 data were fit using a 2:1 heterogeneous ligand model. This model fits the binding of one analyte in solution to two different binding sites on the surface. Kinetic parameters are calculated for both interactions. The secondary structures of the RNAs used in those studies are given in FIG. 10. The graphs of the binding isotherms from surface plasmon resonance experiments are shown in FIG. 25 (A)-(D).

2. Target Pull Down and Northern Blotting

HeLa cells were grown as monolayers in a 75 cm² flask in growth medium to approximately 95% confluency. The cells were transfected with a plasmid expressing a DM1 mini-gene with 960 CTG repeats[4] using Lipofectamine 2000 (Invitrogen) per the manufacturer's protocol. Approximately 24 h post transfection, total RNA was isolated using Trizol reagent (Ambion) according to the manufacturer's protocol.

2H-K4NMe-Biotin and 5'-biotin-d(CAG)$_{12}$ (purchased from Integrated DNA Technologies (IDT) and used without further purification) were conjugated to streptavidin-agarose beads (Sigma, 15 μg/mL biotin loading) by treating 2 nmoles of beads with 50 nmoles of compound or oligonucleotide in water for 1 h at room temperature. Bead saturation with compound was determined by absorbance at 345 nm in the supernatant indicating it contained 2H-K4NMe-Biotin Biotin. The beads were washed with water until no more compound eluted from the resin by monitoring absorbance at 345 nm. Beads treated with 5'-biotin-d(CAG)$_{12}$ were washed with water until the presence of DNA was no longer detected as determined by absorbance at 260 and 280 nm (using a nanodrop spectrophotometer).

Approximately 30 μg of total RNA was folded in 1X PBS for 5 min at 95° C. for 5 min and then cooled to room temperature on the benchtop. The folded RNA was incubated with the beads for 1 h at room temperature with shaking at 500 rpm. The solution was removed and the beads were washed with 300 μL aliquots of 1X PBST until the presence of RNA was no longer detected as determined by absorbance at 260 and 280 mn (using a nanodrop spectrophotometer). The beads were then washed with water to remove all salt and detergents. Bound RNA was released from the beads by heating the beads at 95° C. for 5 min in 100 μL of 95% formamide, 10 mM EDTA. 8.2.

Approximately 2 μg of RNA per sample was separated on a 1.25% (w/v) agarose gel containing 6.66% (v/v) formaldehyde and 1X MESA buffer (20 mM MOPS, 8 mM sodium acetate, 1 mM EDTA, pH 8.0). The gel was electrophoresed at 50 V for 2 h. Following electrophoresis, the gel was submerged in 50 mM NaOH for 20 min and then post stained using 10 μg/mL SYBR gold in 0.5X TBE buffer for 30 min. After staining, the gel was destained in 0.5X TBE buffer for 30 min and then imaged with a Bio-Rad molecular imager gel doe XR+ imaging system.

The RNA was transferred to a nylon membrane (Hybond N+, Amersham) according to the manufacturer's capillary blotting protocol using 20X SSC (3M NaCl, 300 mM sodium citrate, pH 7.0). The transferred RNA was then crosslinked to the membrane by placing the membrane in a Stratagene UV Stratalinker 2400 (120,000 μjoules to 0 μjoules in 30 s). The membrane was washed with boiling 0.1% SDS for 10 min at 37° C. The blot was then hybridized with a ³²P labeled d(CAG)$_{10}$ probe (10 million counts) in 1X Hybridization Buffer (7.5X Denhart's solution, 5X SSPE, and 0.1% SDS) for 18 h at 37° C. Excess probe was removed by washing with Wash Solution 1 (5X SSPE, 0.1% SDS) followed by washing at 37° C. with Wash Solution 2 (0.5X SSPE, 0.1% SDS) 2×10 min. Additional washing with Wash Solution 1 was continued until radioactivity of the wash solution reached background levels. The membrane was air dried and imaged using a Molecular Dynamics Typhoon 9410 variable mode imager.

RT-PCR Amplification to Assess Splicing Defect in a Mouse Model of DM-1

PCR amplification was carried out for 26-30 cycles with the following primer pairs: Clcn1 forward 5'-TGAAGGAATACCTCACACTCAAGG (SEQ ID NO:5) and reverse 5'-(6FAM)CACGGAACACAAAGGCACTG (SEQ ID NO:6); Secral forward 5'-(6FAM)CTCATGGTCCTCAAGATCTCAC (SEQ ID NO:7) and reverse 5'-GGGTCAGTGCCTCAGCTTTG (SEQ ID NO:8). The PCR products were separated by agarose gel electrophoresis. The gel was scanned with a laser fluorimager (Typhoon, GE Healthcare), and the products were quantified using ImageQuant.

Examples Documents Cited

1. Pushechnikov, A., Lee, M. M., Childs-Disney, J. Sobczak, K., French, J. M., Thornton, C. A., and Disney, M. D. (2009) Rational design of ligands targeting triplet repeating transcripts that cause RNA dominant disease: application to myotonic muscular dystrophy type 1 and spinocerebellar ataxia type 3. *J. Am. Chem. Soc.* 131, 9767-9779.

2. Childs-Disney, J. L., Hoskins, J., Rzuczek, S. G., Thornton, C. A., and Disney, M. D. (2012) Rationally designed small molecules targeting the RNA that causes myotonic dystrophy type 1 are potently bioactive, *ACS Chem. Biol.* 7, 856-862.

3. Hook, D. F., Bindschadler, P., Mahajan, Y. R., Sebesta, R., Kast, P., and Scebach, D. (2005) The proteolytic stability of 'designe' beta-peptides containing alpha-peptide-bond mimics and of mixed alpha,beta-peptides: application to the construction of MHC-binding peptides. *Chem. Biodivers.* 2, 591-632.

4. Philips, A. V., Timchenko, L. T., and Cooper, T. A. (1998) Disruption of splicing regulated by a CUG-binding protein in myotonic dystrophy. *Science* 280, 737-741.

5. Warf, M. B., Nakamori, M,. Matthys, C. M., Thornton, C. A., and Berglund, J. A. (2009) Pentamidine reverses the splicing defects associated with myotonic dystrophy. *Proc. Natl. Acad. Sci. U.S.A.* 106, 18551-18556.

What is claimed is:

1. A compound of formula

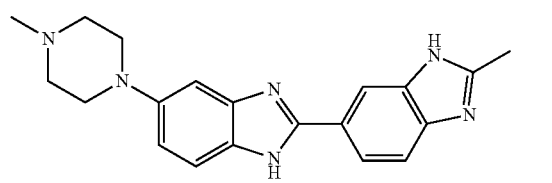

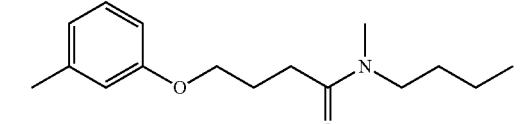

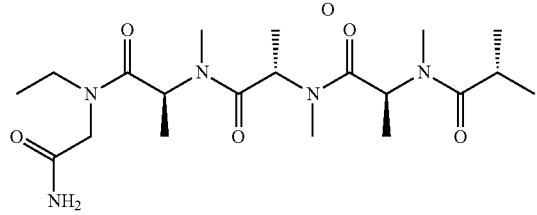

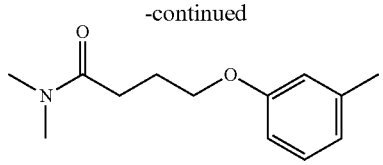

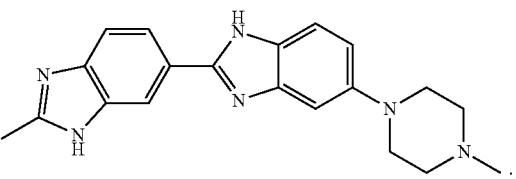

\* \* \* \* \*

UNITED STATES PATENT AND TRADEMARK OFFICE
CERTIFICATE OF CORRECTION

| | | |
|---|---|---|
| PATENT NO. | : 9,795,687 B2 | Page 1 of 1 |
| APPLICATION NO. | : 14/915439 | |
| DATED | : October 24, 2017 | |
| INVENTOR(S) | : Disney et al. | |

It is certified that error appears in the above-identified patent and that said Letters Patent is hereby corrected as shown below:

In the Specification

Column 1, at Line 17, enter the following paragraph:
-- STATEMENT OF GOVERNMENT LICENSE RIGHTS
This invention was made with government support under grant number GM079235 awarded by the National Institutes of Health. The government has certain rights in the invention. --

Signed and Sealed this
Fifth Day of May, 2020

Andrei Iancu
*Director of the United States Patent and Trademark Office*